US012478750B2

(12) United States Patent
Dantanarayana et al.

(10) Patent No.: US 12,478,750 B2
(45) Date of Patent: Nov. 25, 2025

(54) VENTS FOR PATIENT INTERFACES

(71) Applicant: ResMed Pty Ltd, Bella Vista (AU)

(72) Inventors: Muditha Pradeep Dantanarayana, Sydney (AU); Michael Christopher Hogg, Sydney (AU); Stewart Joseph Wagner, Sydney (AU)

(73) Assignee: ResMed Pty Ltd, Bella Vista (AU)

(*) Notice: Subject to any disclaimer, the term of this patent is extended or adjusted under 35 U.S.C. 154(b) by 817 days.

(21) Appl. No.: 17/828,690

(22) Filed: May 31, 2022

(65) Prior Publication Data

US 2022/0401681 A1 Dec. 22, 2022

(30) Foreign Application Priority Data

May 31, 2021 (AU) ................................ 2021901623
Aug. 9, 2021 (AU) ................................ 2021902448

(51) Int. Cl.
*A61M 16/06* (2006.01)
*A61M 16/08* (2006.01)

(52) U.S. Cl.
CPC .... *A61M 16/0616* (2014.02); *A61M 16/0666* (2013.01); *A61M 16/0816* (2013.01)

(58) Field of Classification Search
CPC .............. A61M 16/06; A61M 16/0611; A61M 16/0616; A61M 16/0622; A61M 16/0666; A61M 16/0816; A61M 16/0866; A61M 16/208
See application file for complete search history.

(56) References Cited

U.S. PATENT DOCUMENTS 4,782,832 A 11/1988 Trimble et al.
4,944,310 A 7/1990 Sullivan
5,687,715 A 11/1997 Landis
(Continued)

FOREIGN PATENT DOCUMENTS

EP 2 027 880 A1 2/2009
WO WO 98/004310 A1 2/1998
(Continued)

OTHER PUBLICATIONS

"*Respiratory Physiology*", by John B. West, Lippincott Williams & Wilkins, 9th edition published 2012 (8 pages).
(Continued)

*Primary Examiner* — Joseph D. Boecker
(74) *Attorney, Agent, or Firm* — Nixon & Vanderhye P.C.

(57) ABSTRACT

The technology relates to a vent for a respiratory therapy system. The vent comprises a vent body having formed therein a plurality of slots allowing a vent flow of exhaled gases to ambient. The slots have a length, a width and a height. In examples the width of each slot is significantly greater than the height and the slots are arranged such that the widths of the slots extend in mutually parallel directions. The vent body may also be configured so that the length of each slot is significantly greater than the height and/or the outlet area is greater than the inlet area. In examples the vent is provided with a cover and an actuator to move the cover between a first position in which the cover at least partially occludes flow through the vent and a second position in which the degree of occlusion is reduced.

18 Claims, 40 Drawing Sheets

(56) References Cited

U.S. PATENT DOCUMENTS

| | | | |
|---|---|---|---|
| 6,532,959 | B1 | 3/2003 | Berthon-Jones |
| 6,581,594 | B1 | 6/2003 | Drew et al. |
| 6,951,218 | B2 | 10/2005 | Gradon et al. |
| 7,302,950 | B2 | 12/2007 | Berthon-Jones et al. |
| 7,866,944 | B2 | 1/2011 | Kenyon et al. |
| 8,439,035 | B2 | 5/2013 | Dantanarayana et al. |
| 8,636,479 | B2 | 1/2014 | Kenyon et al. |
| 8,638,014 | B2 | 1/2014 | Sears et al. |
| 8,733,349 | B2 | 5/2014 | Bath et al. |
| 9,038,635 | B2 | 5/2015 | Brambilla |
| 9,415,183 | B2 | 8/2016 | Allum et al. |
| 9,878,121 | B2 | 1/2018 | Brambilla et al. |
| 2009/0044808 | A1 | 2/2009 | Guney et al. |
| 2009/0050156 | A1* | 2/2009 | Ng .................... A61M 16/0816 128/205.24 |
| 2010/0000534 | A1 | 1/2010 | Kooij et al. |
| 2016/0175552 | A1 | 6/2016 | Harrington |
| 2017/0035978 | A1 | 2/2017 | Holley et al. |
| 2018/0207309 | A1 | 7/2018 | Salowitz et al. |
| 2018/0264222 | A1 | 9/2018 | Dantanarayana et al. |
| 2019/0209804 | A1 | 7/2019 | Dantanarayana et al. |
| 2019/0262571 | A1 | 8/2019 | Fong et al. |
| 2019/0351173 | A1 | 11/2019 | Dantanarayana et al. |
| 2022/0096768 | A1* | 3/2022 | Grashow ........... A61M 16/0866 |

FOREIGN PATENT DOCUMENTS

| | | | | |
|---|---|---|---|---|
| WO | WO 98/034665 | A1 | 8/1998 | |
| WO | WO 2000/078381 | A1 | 12/2000 | |
| WO | WO 2004/073778 | A1 | 9/2004 | |
| WO | WO 2005/063328 | A1 | 7/2005 | |
| WO | 2006/074516 | A1 | 7/2006 | |
| WO | WO 2006/074513 | A1 | 7/2006 | |
| WO | WO 2006/130903 | A1 | 12/2006 | |
| WO | WO 2009/052560 | A1 | 4/2009 | |
| WO | 2010/139014 | A1 | 12/2010 | |
| WO | WO 2010/135785 | A1 | 12/2010 | |
| WO | WO 2012/171072 | A1 | 12/2012 | |
| WO | WO 2013/020167 | A1 | 2/2013 | |
| WO | 2013/040198 | A2 | 3/2013 | |
| WO | 2016/041019 | A1 | 3/2016 | |
| WO | WO-2020170207 | A1 * | 8/2020 | ........ A61M 16/0003 |
| WO | 2020/172708 | A1 | 9/2020 | |
| WO | 2020/240495 | A1 | 12/2020 | |
| WO | 2021/087570 | A1 | 5/2021 | |

OTHER PUBLICATIONS

Extended European Search Report dated Oct. 27, 2022 issued in European Application No. 22176548.0 (8 pages).

* cited by examiner

Copyright 2015 ResMed Limited

VENTS FOR PATIENT INTERFACES

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

1 CROSS-REFERENCE TO RELATED APPLICATIONS

This application claims priority to Australian Provisional Application Nos. 2021901623, filed May 31, 2021, and 2021902448, filed Aug. 9, 2021, the entire contents of each is incorporated herein by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient CO2 to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube or endotracheal tube. In some forms, the comfort and effectiveness of these therapies may be improved.

2.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that may be held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired CO2 from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched air at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$. For flow therapies such as nasal HFT, the patient interface is configured to insufflate the nares but specifically to avoid a complete seal. One example of such a patient interface is a nasal cannula.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design is able to fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.1.3 Pressurised Air Conduit

In one type of treatment system, a flow of pressurised air is provided to a patient interface through a conduit in an air circuit that fluidly connects to the patient interface so that, when the patient interface is positioned on the patient's face during use, the conduit extends out of the patient interface forwards away from the patient's face. This may sometimes be referred to as a "tube down" configuration.

Some patients find such interfaces to be unsightly or to create a feeling of claustrophobia and are consequently deterred from wearing them, reducing patient compliance. Additionally, conduits connecting to an interface at the front of a patient's face may sometimes be vulnerable to becoming tangled up in bed clothes.

2.2.3.1.4 Pressurised Air Conduit Used for Positioning/Stabilising the Seal-Forming Structure An alternative type of treatment system which seeks to address these problems comprises a patient interface in which a tube that delivers pressurised air to the patient's airways also functions as part of the headgear to position and stabilise the seal-forming portion of the patient interface at the appropriate part of the patient's face. This type of patient interface may be referred to as having "conduit headgear" or "headgear tubing". Such patient interfaces allow the conduit in the air circuit providing the flow of pressurised air from a respiratory pressure therapy device to connect to the patient interface in a position other than in front of the patient's face. One example of such a treatment system is disclosed in US Patent Publication No. US 2007/0246043, the contents of which are incorporated herein by reference, in which the conduit connects to a tube in the patient interface through a port positioned in use on top of the patient's head.

Patient interfaces incorporating headgear tubing may provide some advantages, for example avoiding a conduit connecting to the patient interface at the front of a patient's face, which may be unsightly and obtrusive.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

2.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition, in cooler climates, warm air applied generally to the face area in and about the patient interface is more comfortable than cold air.

2.2.3.5 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2: 2007, 10 cmH2O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed MirageTM (*) | nasal | 29.5 | 21.5 | 1998 |
| ResMed UltraMirageTM | nasal | 36 (3) | 28 (3) | 2000 |
| ResMed Mirage ActivaTM | nasal | 32 (3) | 24 (3) | 2002 |
| ResMed Mirage MicroTM | nasal | 30 (3) | 22 (3) | 2008 |
| ResMed MirageTM SoftGel | nasal | 29 (3) | 22 (3) | 2008 |
| ResMed MirageTM FX | nasal | 26 (3) | 18 (3) | 2010 |
| ResMed Mirage SwiftTM (*) | nasal pillows | 37 | 29 | 2004 |
| ResMed Mirage SwiftTM II | nasal pillows | 28 (3) | 20 (3) | 2005 |
| ResMed Mirage SwiftTM LT | nasal pillows | 25 (3) | 17 (3) | 2008 |
| ResMed AirFit P10 | nasal pillows | 21 (3) | 13 (3) | 2014 |

((*) one specimen only, measured using test method specified in ISO 3744 in CPAP mode at 10 cmH2O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |

-continued

| Object | A-weighted sound pressure dB(A) | Notes |
|---|---|---|
| Quiet bedroom at night | 30 | |
| Background in TV studio | 20 | |

The velocity of gas exiting a vent is an important consideration for the comfort of a patient 1000 and/or a bed partner 1100. More noise is typically produced if the magnitude of the velocity of the vented gas flow is higher and, as explained above, noisy vents are generally undesirable. Furthermore, vented gas with a high velocity that blows onto the patient 1000 or the bed partner 1100 may be felt by that person and cause discomfort. High velocity air may also generate noise if it impacts against a surface such as pillows or other bedding.

Some patient interfaces use diffusers to reduce the velocity of vented gases. This can be effective, but it requires an additional component which increases the material cost of the product and the manufacturing cost and complexity. Furthermore, some diffusers wear or become dirty through use and consequently need to be replaced at cost to the patient. Alternatively, patients may not replace the diffuser and the performance of the patient interface is adversely affected as a result.

Some respiratory therapy patients may dislike the experience of breathing pressurised air and may have difficulty falling asleep while wearing a patient interface which is being supplied with air at full treatment pressure. Difficulty in falling asleep may be a factor in reduced compliance in some patients.

In an attempt to mitigate this problem, some RPT devices of the prior art may supply air at a pressure lower than treatment pressure for a period of time before increasing the supplied pressure to the treatment pressure. In some prior art examples, the pressure may be increased after a predetermined length of time has passed. However, in some other prior art examples the RPT device may increase the supplied pressure after the RPT device has determined that the patient has fallen asleep.

Although such RPT devices do go some way towards addressing the problem of patients having difficulty falling asleep while wearing a patient interface which is being supplied with air at full treatment pressure, the need for adequate $CO_2$ washout of the patient interface puts an effective lower limit on the pressure which can be supplied to the patient interface. The pressure at this lower limit may still be sufficiently high to cause discomfort and/or difficulty in falling asleep for some patients.

One proposed way of addressing this problem is to provide the patient interface with a vent which has a variable impedance to flow. PCT publication WO 2013040198 describes a vent with a cover which can be opened by an electromagnetic solenoid to decrease the impedance of the vent, for example when the patient is falling asleep, and which can then be adjusted to increase the impedance of the vent (and hence the pressure within the plenum chamber) when the patient is asleep. One problem with such an adjustable vent may be that the movement of the cover to increase the impedance of the vent may cause a noise and/or a vibration through the patient interface 3000 which is sufficient to rouse the patient.

3 BRIEF SUMMARY OF THE TECHNOLOGY

The present technology is directed towards providing medical devices used in the amelioration, treatment, or prevention of respiratory disorders having one or more of improved comfort, cost, efficacy, ease of use and manufacturability.

A first aspect of the present technology relates to apparatus used in the amelioration, treatment or prevention of a respiratory disorder.

An aspect of certain forms of the present technology is to provide apparatus that improve the compliance of patients with respiratory therapy.

One form of the present technology comprises a vent for a respiratory therapy system. The vent may address one or more of the aforementioned problems of prior art vents relating to noise, discomfort and efficacy.

Another aspect of one form of the present technology is a vent for a respiratory therapy system, the vent allowing for a vent flow of gases exhaled by a patient receiving a flow of breathable gas from a volume interior to the respiratory therapy system to ambient. The vent may comprise a vent body having formed therein a plurality of slots, the plurality of slots together allowing the vent flow of exhaled gases from the volume to ambient. Each of the plurality of slots may have an inlet and an outlet, a length extending perpendicularly between the inlet and the outlet, a width and a height, each of the width and the height extending in a direction perpendicular to the length. The vent body may be configured such that, for each of the plurality of slots, the width is significantly greater than the height, and the length is significantly greater than the height. The vent body may be configured such that the plurality of slots are arranged such that the widths of the plurality of slots extend in mutually parallel directions.

In certain forms, for each of the plurality of slots, a ratio of the length to the height is at least 10. The ratio of the length to the height may be at most 40.

In certain forms, for each of the plurality of slots, a ratio of the width to the height is at least 15.

In certain forms, for each of the plurality of slots, the inlet has an inlet area and the outlet has an outlet area, and the outlet area is greater than the inlet area. For example, for each of the plurality of slots, a width of the slot at the outlet may be greater than a width of the slot at the inlet. In another example, for each of the plurality of slots, a height of the slot at the outlet may be greater than a height of the slot at the inlet.

In certain forms, the vent body may be configured such that, for each of the plurality of slots, the slot is formed between a first side wall and a second side wall, each of the first side wall and the second side wall being surfaces of the vent body, the first side wall and the second side wall being separated in a direction parallel to the height of the slot, and wherein the vent body is configured such that the first side wall and the second side wall are substantially planar.

In certain forms, in a direction along the width of the slot, the slot may have a middle region proximate the middle of the slot and end regions proximate the ends of the slot, and wherein a length of the slot in the middle region is greater than a length of the slot in the end regions. Alternatively, the length of the slot may be substantially the same across the width of the slot.

In certain forms, in use, the vent body may be mounted between at least one wall of the respiratory therapy system, wherein the vent body projects inwardly from the at least one wall into the volume. Additionally, or alternatively, in use, the vent body may be mounted between at least one wall of the respiratory therapy system, wherein the vent body projects outwardly from the at least one wall into ambient.

Another aspect of one form of the present technology is a vent for a respiratory therapy system, the vent allowing for a vent flow of gases exhaled by a patient receiving a flow of breathable gas from a volume interior to the respiratory therapy system to ambient. The vent may comprise a vent body having formed therein a plurality of slots, the plurality of slots together allowing the vent flow of exhaled gases from the volume to ambient. Each of the plurality of slots may have an inlet having an inlet area and an outlet having an outlet area, a length extending perpendicularly between the inlet and the outlet, a width and a height, each of the width and the height extending in a direction perpendicular to the length. The vent body may be configured such that, for each of the plurality of slots, the width is significantly greater than the height, and the outlet area is greater than the inlet area. The vent body may be configured such that the plurality of slots are arranged such that the widths of the plurality of slots extend in mutually parallel directions.

In certain forms, for each of the plurality of slots, a width of the slot at the outlet may be greater than a width of the slot at the inlet.

In certain forms, the vent body may be configured such that, for each of the plurality of slots, the slot is formed between a first end wall and a second end wall, each of the first end wall and the second end wall being surfaces of the vent body, the first end wall and the second end wall being separated in a direction parallel to the width of the slot, and wherein a projection of the first end wall inwardly towards the volume would intersect with a projection of the second end wall inwardly towards the volume.

In certain forms, the angle at which the first end wall is oriented to the second end wall may be at least 60°.

In certain forms, for each of the plurality of slots, a height of the slot at the outlet may be greater than a height of the slot at the inlet.

In certain forms, the vent body may be configured such that, for each of the plurality of slots, the slot is formed between a first side wall and a second side wall, each of the first side wall and the second side wall being surfaces of the vent body, the first side wall and the second side wall being separated in a direction parallel to the height of the slot, and wherein the vent body is configured such that the first side wall and the second side wall are substantially planar.

In certain forms, for each of the plurality of slots, the first side wall may be oriented at an angle of at least 1° relative to the second side wall.

In certain forms, the vent body may be configured such that, for each of the plurality of slots, the inlet is concave across the width of the slot. Additionally, or alternatively, the vent body may be configured such that, for each of the plurality of slots, the outlet is convex across the width of the slot.

In certain forms, for each of the plurality of slots, a ratio of the width to the height may be at least 15.

In certain forms, for each of the plurality of slots, the length may be significantly greater than the height. For example, for each of the plurality of slots, a ratio of the length to the height may be at least 10. The ratio of the length to the height may be at most 40.

Another aspect of the technology provides a vent module for a respiratory therapy system. The vent module in use allows for a vent flow of gases exhaled by a patient receiving a flow of breathable gas from a volume interior to the respiratory therapy system to ambient. The vent module may comprise a vent body having formed therein a plurality of slots, the plurality of slots together allowing the vent flow of exhaled gases from the volume to ambient. Each of the plurality of slots may have an inlet and an outlet, a length extending perpendicularly between the inlet and the outlet, a width and a height, each of the width and the height extending in a direction perpendicular to the length. The vent body may be configured such that, for each of the plurality of slots, the width is significantly greater than the height. The vent body may be configured such that the plurality of slots are arranged such that the widths of the plurality of slots extend in mutually parallel directions.

In certain forms, the vent module may comprise a vent according to one of the other aspects of the technology.

Another aspect of one form of the present technology is a patient interface for a respiratory therapy system. In one form the patient interface comprises a vent that addresses one or more of the aforementioned problems of prior art vents relating to noise, discomfort and efficacy.

In certain forms, the patient interface may comprise a plenum chamber pressurisable to a therapeutic pressure of at least 6 $cmH_2O$ above ambient air pressure, said plenum chamber including a plenum chamber inlet port sized and structured to receive a flow of air at the therapeutic pressure for breathing by a patient. The patient interface may further comprise a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use. The patient interface may further comprise a vent according to one of the other aspects of the technology, wherein the vent allows a continuous flow of gases exhaled by the patient from an interior of the plenum chamber to ambient, said vent being configured to maintain the therapeutic pressure in the plenum chamber in use. The patient interface may be configured to allow the patient to breath from ambient through their mouth in the absence of a flow of pressurised air through the plenum chamber inlet port, or the patient interface is configured to leave the patient's mouth uncovered.

In certain forms, the vent is provided to the plenum chamber.

In certain forms, the patient interface may comprise a tube portion having a first end fluidly connected to the plenum chamber inlet port and a second end configured to directly or indirectly fluidly connect to an air circuit to receive the flow of air, wherein the vent is provided in the tube portion. The tube portion may comprise a bend between the first end and the second end such that the tube portion is in the form of an elbow.

Another aspect of one form of the present technology is a tube portion for use with a patient interface in a respiratory system. The tube portion may comprise a first end fluidly connected to a plenum chamber inlet port of the patient interface and a second end configured to directly or indirectly fluidly connect to an air circuit to receive a flow of air at a therapeutic pressure of at least 6 $cmH_2O$ above ambient air pressure. A vent according to one of the other aspects of the technology may be provided in the tube portion.

In certain forms, the tube portion may comprise a bend between the first end and the second end such that the tube portion is in the form of an elbow.

Another aspect of one form of the present technology comprises a vent for a patent interface for delivering respiratory therapy to a patient, the vent comprising an aperture, a cover, and an actuator configured to move the cover between a first position or configuration in which the cover at least partially occludes the aperture and a second position or configuration in which the degree of occlusion is reduced, the vent comprising a controller configured to operate the actuator to move the cover between the first and second positions or configurations, wherein the rate of the movement of the cover from the second position or configuration to the first position or configuration is controlled to reduce or avoid noise and/or vibration.

In examples: a) the vent comprises a plurality of apertures; b) the cover occludes a plurality of the apertures when in the first position; c) a plurality of the apertures are not occluded by the cover when the cover is in the first position; d) the actuator comprises a stepper motor provided with a leadscrew; e) the actuator comprises an electromagnet; f) the cover is biased towards the second position or configuration; g) the cover comprises a resilient portion configured to bias the cover toward the second position or configuration; and/or h) the vent comprises a housing and the actuator is housed within the housing.

Another aspect of one form of the present technology comprises a vent for a patent interface for delivering respiratory therapy to a patient, the vent comprising a body, the body defining a housing having an opening, the body further defining at least one flow path from a first side of the body to an opposite second side of the body, the vent further comprising a cover having a base portion configured to engage the body and seal the opening, thereby sealing the housing, and a head portion configured to move between a first position or configuration in which the head portion at least partially occludes the flow path and a second position or configuration in which the degree of occlusion is reduced, the vent further comprising an actuator provided within the housing, the actuator configured to move the head portion between the first and second positions or configurations.

In examples: a) the flow path comprises at least one annular opening; b) the flow path comprises a plurality of concentric annular openings; c) at least a portion of the head portion extends laterally beyond the base portion; d) the cover is substantially mushroom or umbrella shaped; e) the actuator comprises a stepper motor provided with a leadscrew; f) the actuator comprises an electromagnet; g) the head portion of the cover is biased towards the second position or configuration; h) the cover comprises a resilient portion configured to bias the head portion toward the second position or configuration; i) the vent arrangement comprises a battery provided within the housing; j) the vent arrangement comprises means for inductively charging the battery; and/or k) the vent arrangement comprises means for wirelessly controlling the actuator.

One form of the present technology comprises a vent for a patent interface for delivering respiratory therapy to a patient, the vent comprising a plurality of concentric annular flow paths, wherein a cross-sectional area of each flow path increases from an upstream end of the flow path to the downstream end.

In examples: a) the cross-sectional area increases continuously from the upstream end to the downstream end of each flow path; b) the cross-sectional area increases substantially linearly from the upstream end to the downstream end; c) the ratio of the width the inlet to each flow path to the length of each flow path is less than 1:30, for example around 1:40; d) the vent comprises a cover, and an actuator configured to move the cover between a first position or configuration in which the cover at least partially occludes at least one of the flow paths and a second position or configuration in which the degree of occlusion is reduced, the vent comprising a controller configured to operate the actuator to move the cover between the first and second positions or configurations; e) movement of the cover from the second position to the first position is controlled to reduce or avoid noise and/or vibration; f) the vent comprises a body, the body defining a housing having an opening, the body further defining the plurality of flow paths, wherein the cover has a base portion configured to engage the body and seal the opening, thereby sealing the housing, and a head portion configured to move between a first position or configuration in which the head portion at least partially occludes at least one of the flow paths and a second position or configuration in which the degree of occlusion is reduced; g) the actuator is provided within the housing; and/or h) the vent is configured such that it can be injection moulded without any undercut.

An aspect of one form of the present technology is a method of manufacturing apparatus.

An aspect of one form of the present technology is a patient interface that may be washed in a home of a patient, e.g., in soapy water, without requiring specialised cleaning equipment.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1 shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

4.2 Patient Interface

FIG. 2A shows a patient interface in the form of a nasal mask in accordance with one form of the present technology.

FIG. 2B shows a schematic of a cross-section through a structure at a point. An outward normal at the point is indicated. The curvature at the point has a positive sign, and a relatively large magnitude when compared to the magnitude of the curvature shown in FIG. 2C.

FIG. 2C shows a schematic of a cross-section through a structure at a point. An outward normal at the point is indicated. The curvature at the point has a positive sign, and a relatively small magnitude when compared to the magnitude of the curvature shown in FIG. 2B.

FIG. 2D shows a schematic of a cross-section through a structure at a point. An outward normal at the point is indicated. The curvature at the point has a value of zero.

FIG. 2E shows a schematic of a cross-section through a structure at a point. An outward normal at the point is indicated. The curvature at the point has a negative sign, and a relatively small magnitude when compared to the magnitude of the curvature shown in FIG. 2F.

FIG. 2F shows a schematic of a cross-section through a structure at a point. An outward normal at the point is indicated. The curvature at the point has a negative sign, and a relatively large magnitude when compared to the magnitude of the curvature shown in FIG. 2E.

FIG. 2G shows a patient interface in the form of a mask having conduit headgear in accordance with one form of the present technology.

4.3 Humidifier

4.4 Vent

Figure 4A:
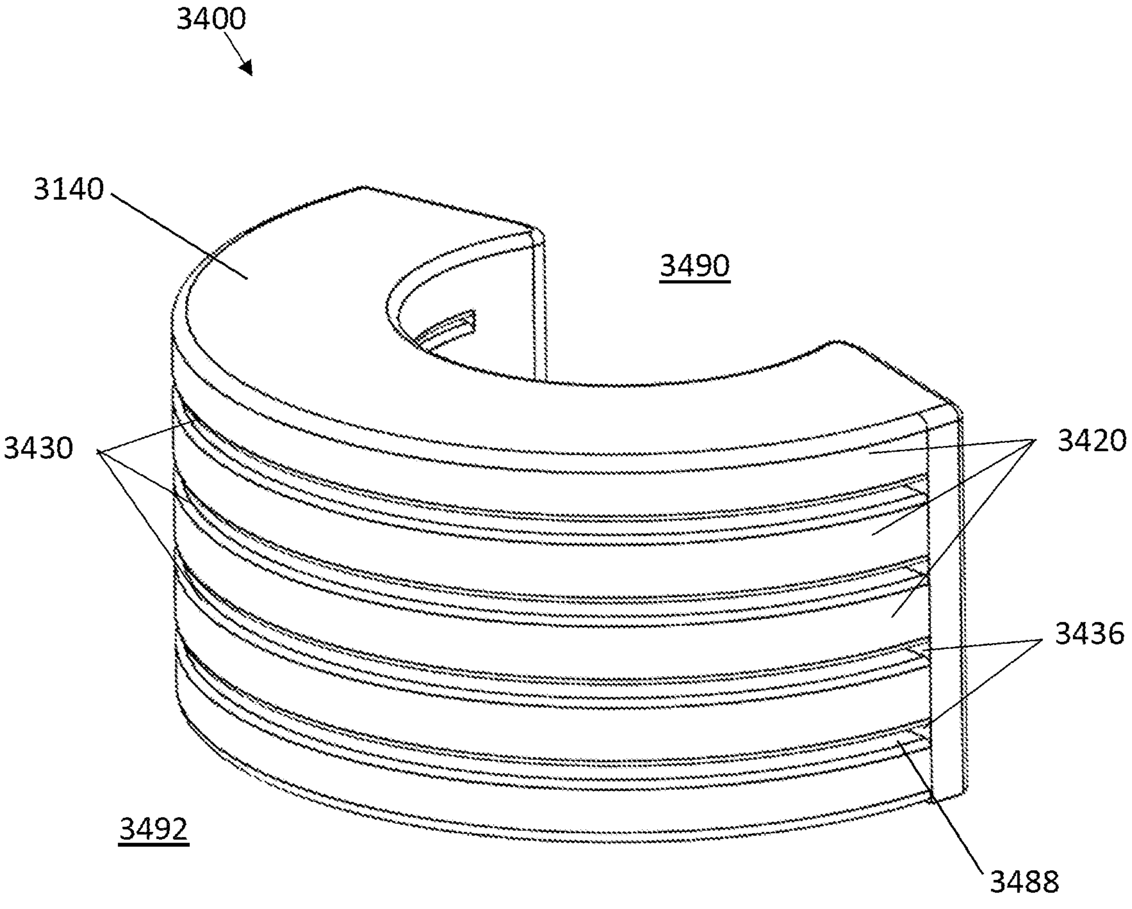

FIG. 4A shows an isometric view of a vent 3400 in accordance with one form of the present technology.

Figure 4B:
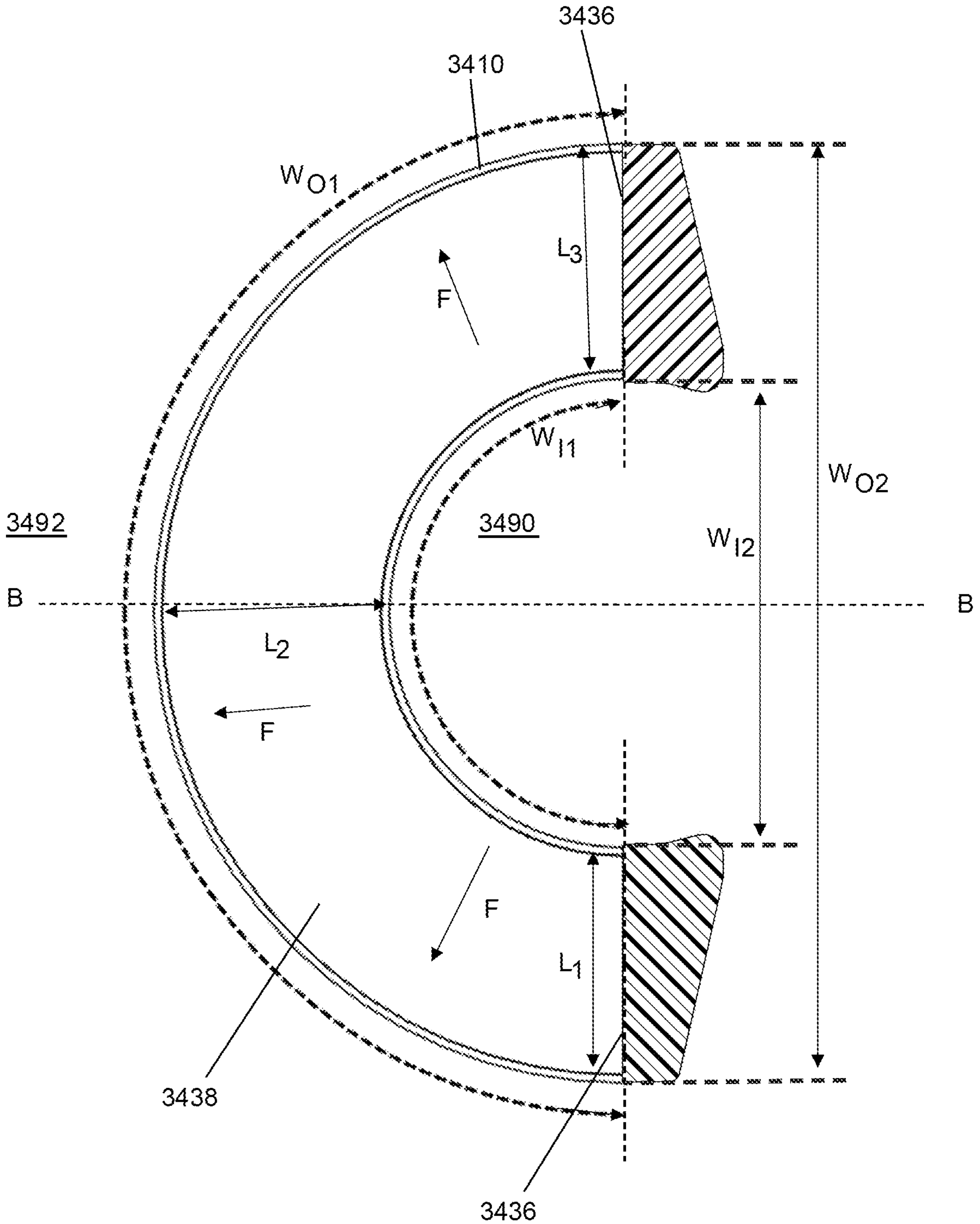

FIG. 4B shows a top cross-sectional view of the vent 3400 shown in FIG. 4A.

Figure 4C:
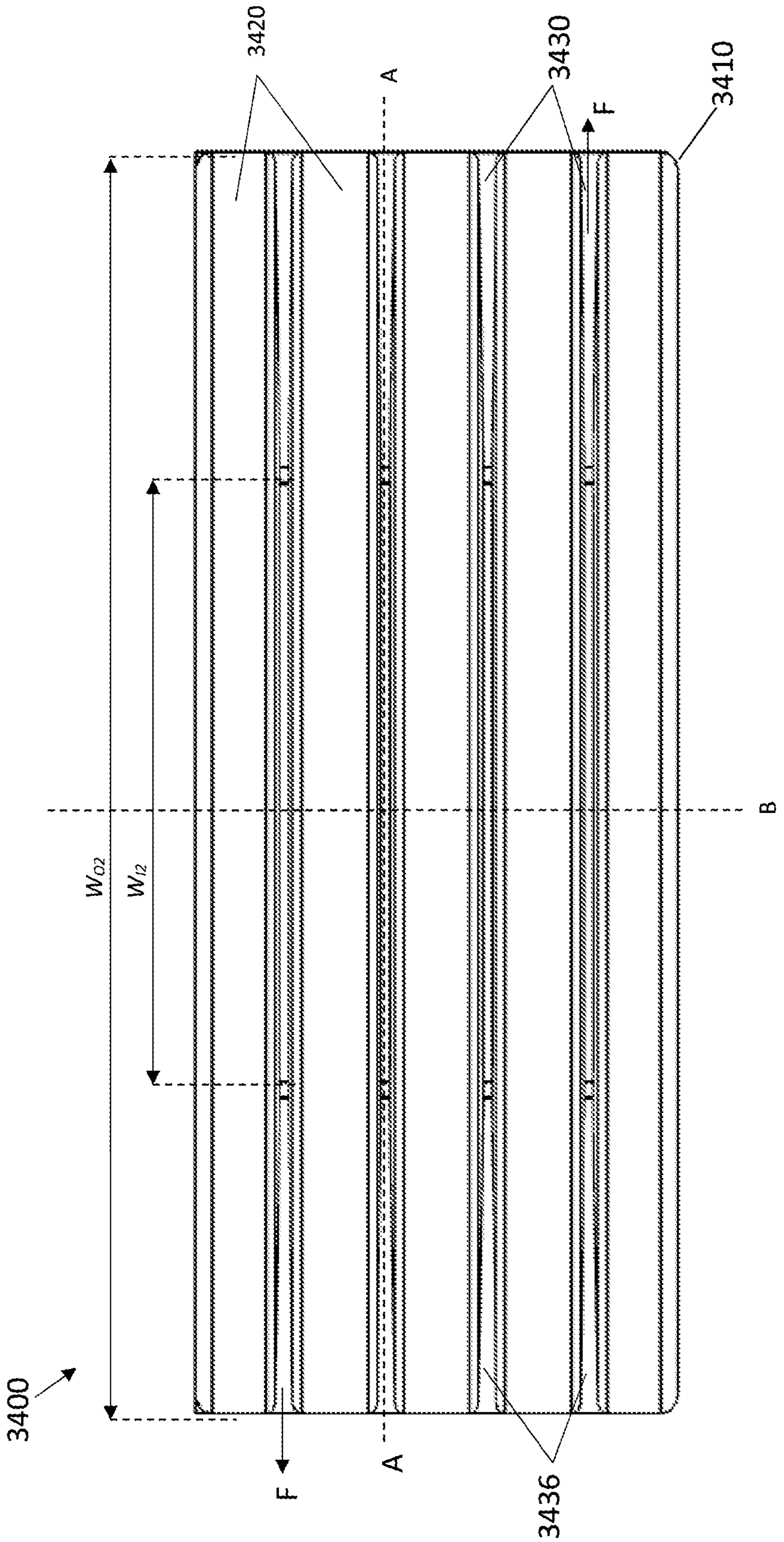

FIG. 4C shows a front view of the vent 3400 shown in FIG. 4A.

Figure 4D:
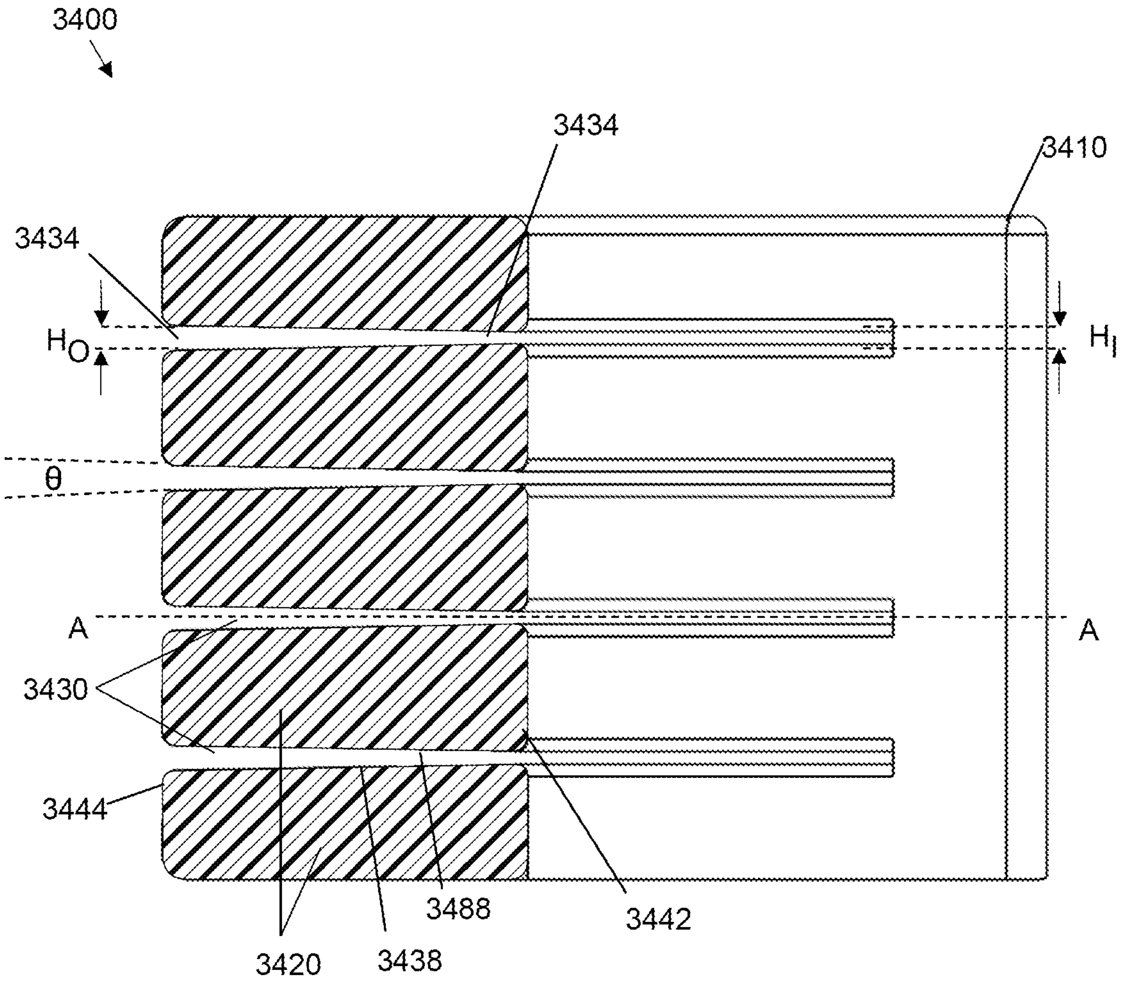

FIG. 4D shows a side cross-sectional view of the vent 3400 shown in FIG. 4A.

Figure 5A:
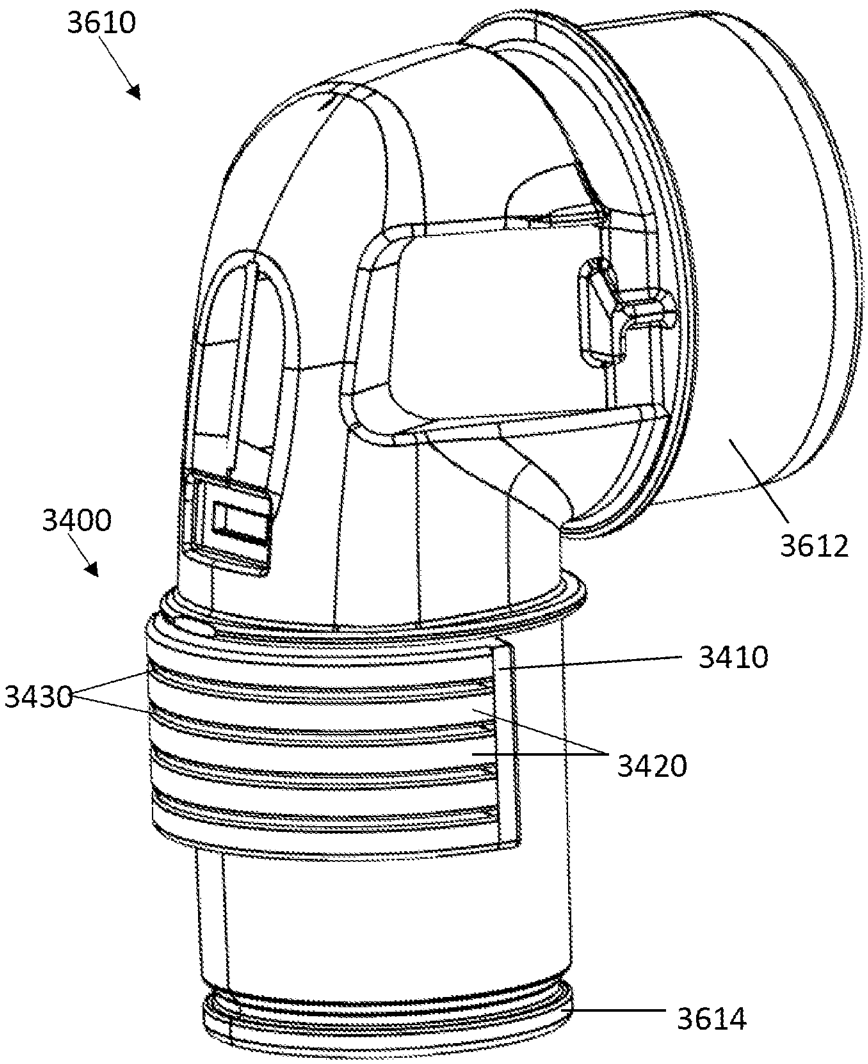

FIG. 5A shows an isometric view of an elbow 3610 in accordance with one form of the present technology. Elbow 3610 comprises the vent 3400 shown in FIGS. 4A-4D.

Figure 5B:
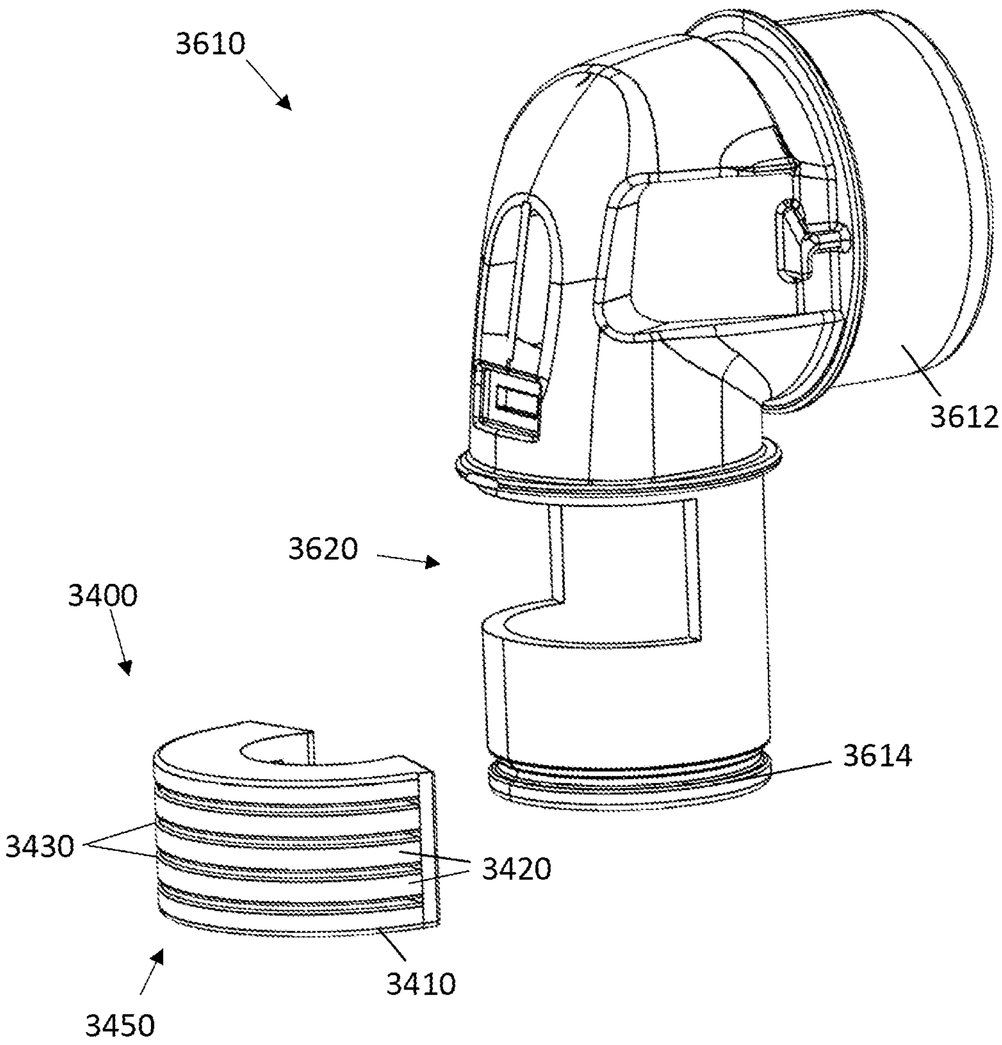

FIG. 5B shows an exploded view of the elbow 3610 shown in FIG. 5A.

Figure 5C:
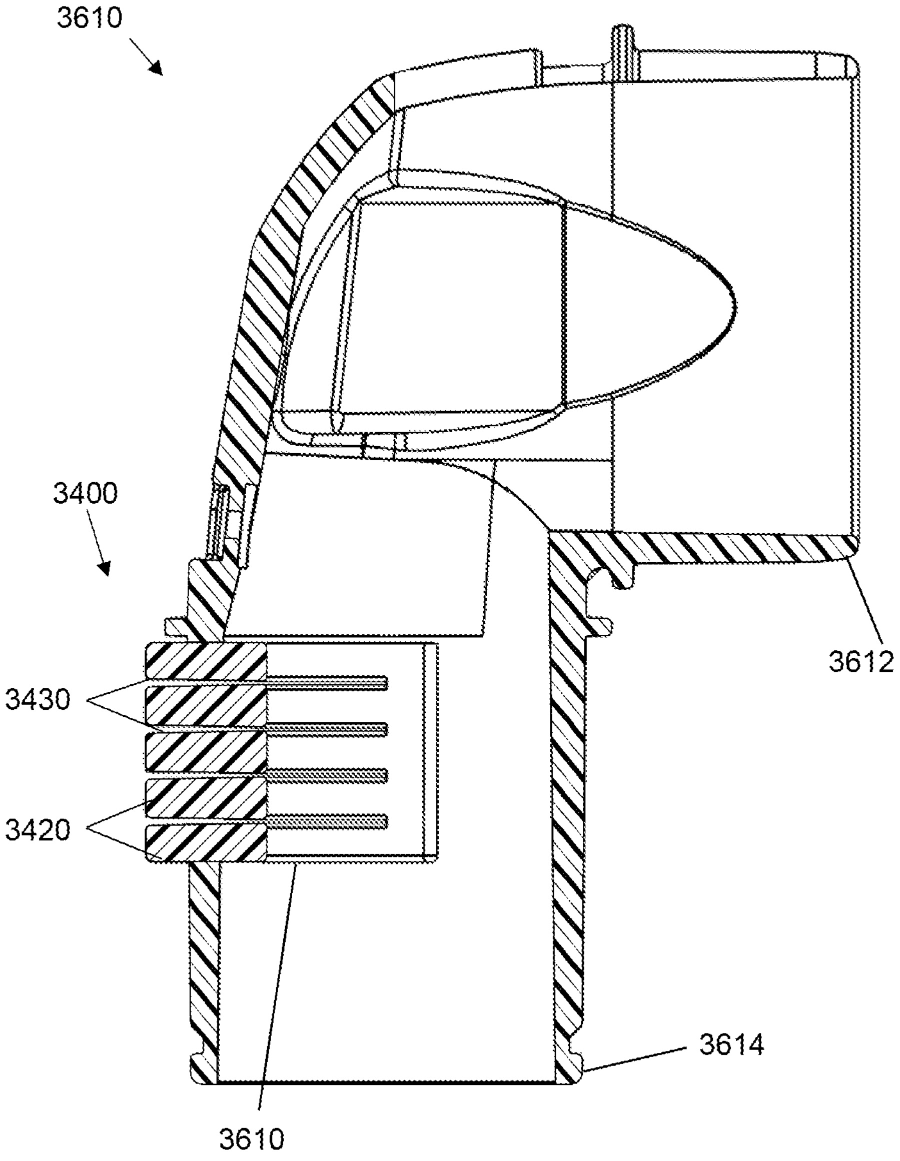

FIG. 5C shows a side cross-sectional view of the elbow 3610 shown in FIG. 5A.

Figure 6A:
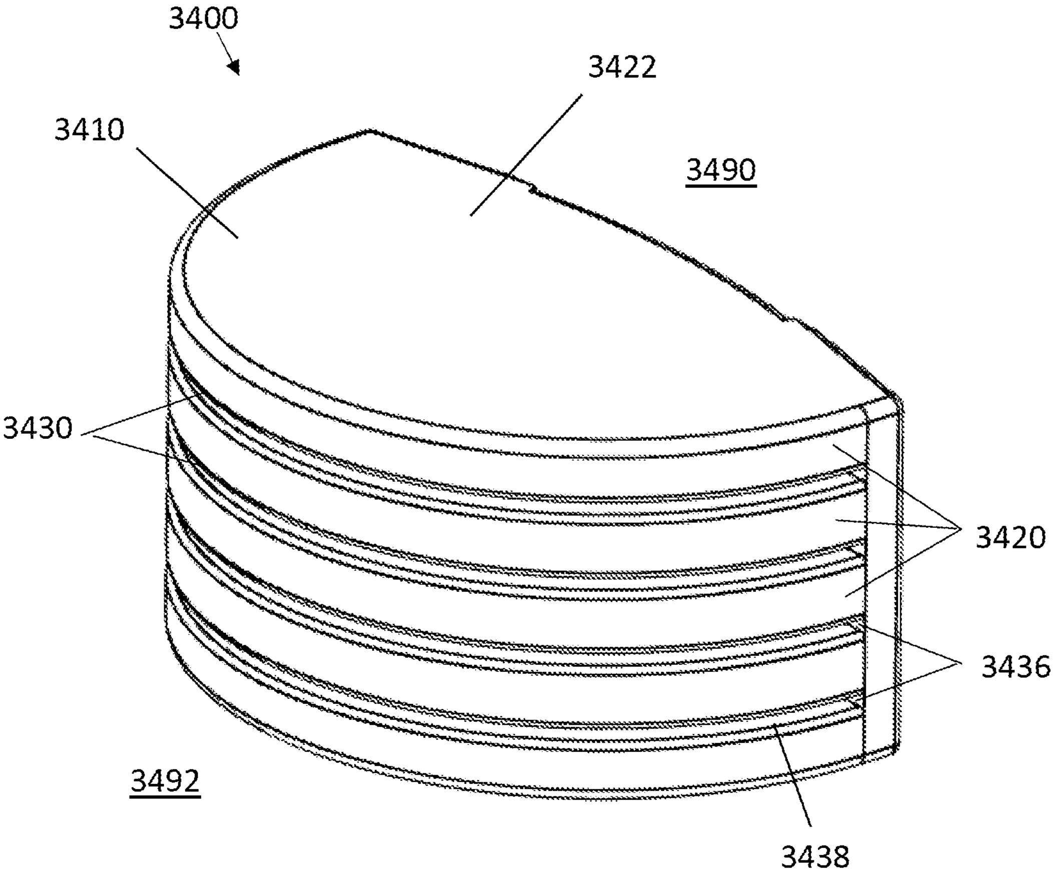

FIG. 6A shows an isometric view of a vent 3400 in accordance with one form of the present technology.

Figure 6B:
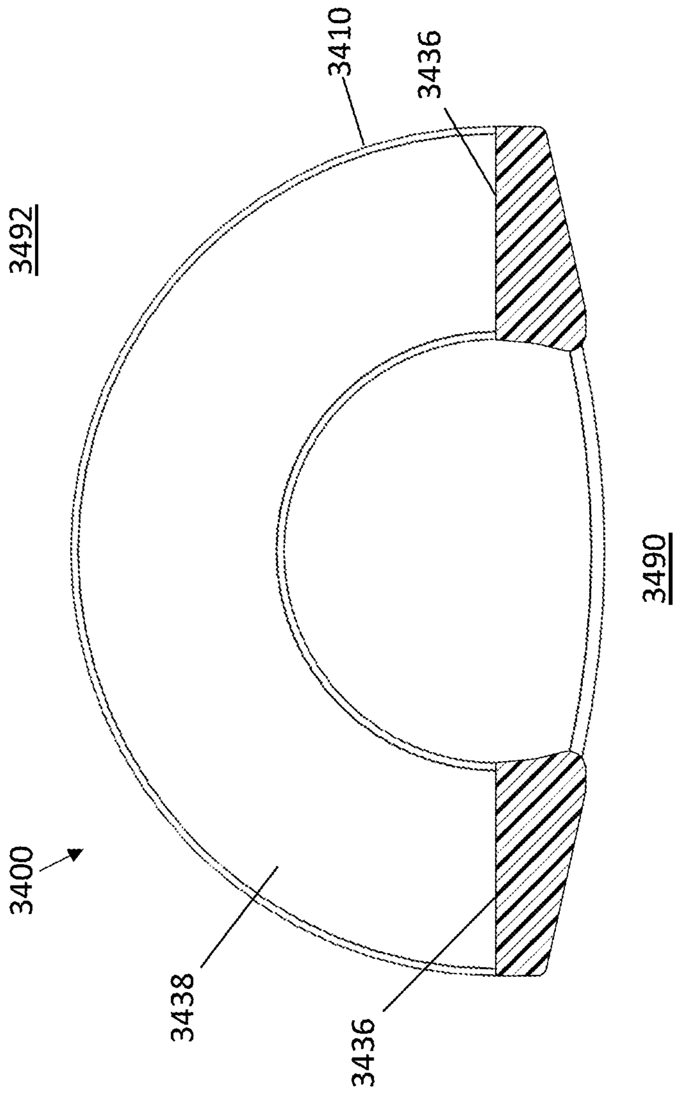

FIG. 6B shows a top cross-sectional view of the vent 3400 shown in FIG. 6A.

Figure 6C:
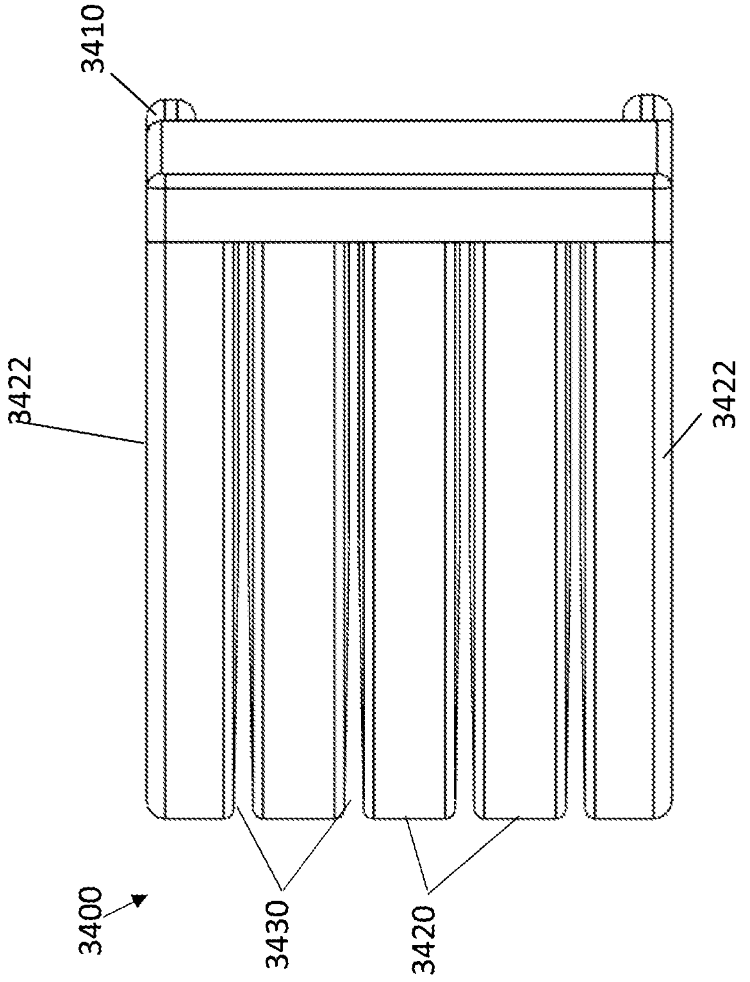

FIG. 6C shows a side view of the vent 3400 shown in FIG. 6A.

Figure 6D:
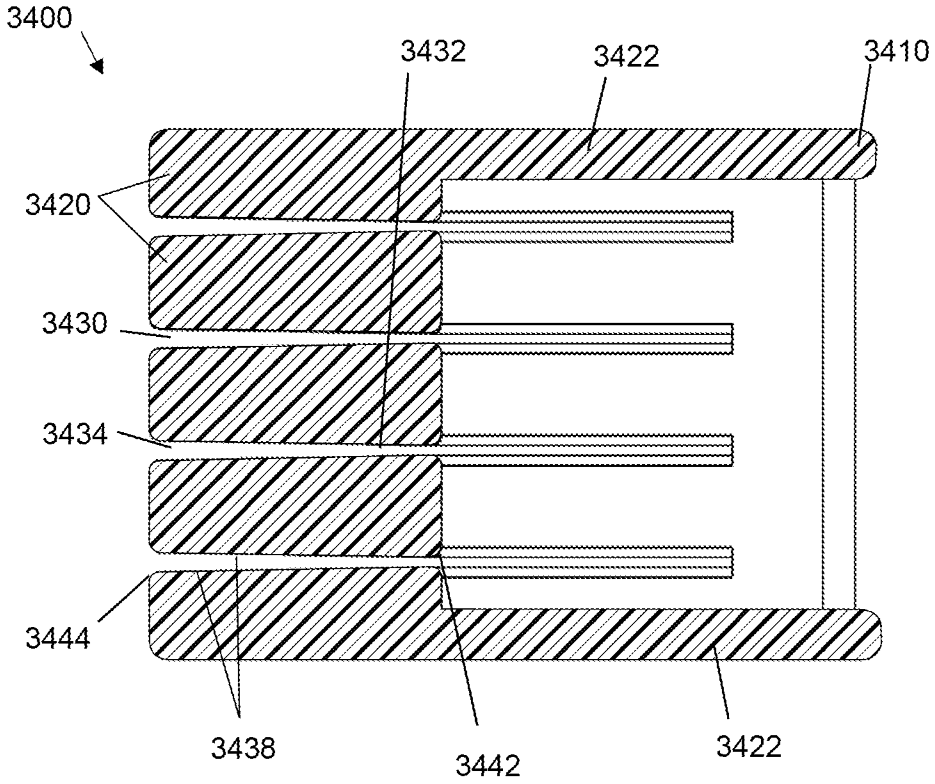

FIG. 6D shows a side cross-sectional view of the vent 3400 shown in FIG. 6A.

Figure 7A:
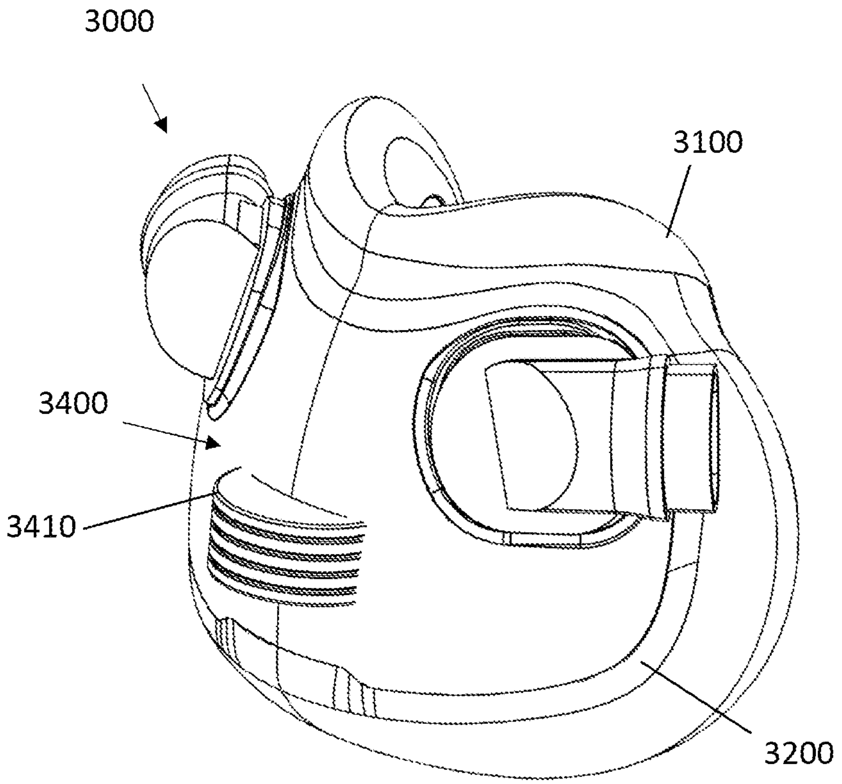

FIG. 7A shows an isometric view of a patient interface 3000 in accordance with one form of the present technology. Patient interface 3000 comprises the vent 3400 shown in FIGS. 6A-6D.

Figure 7B:
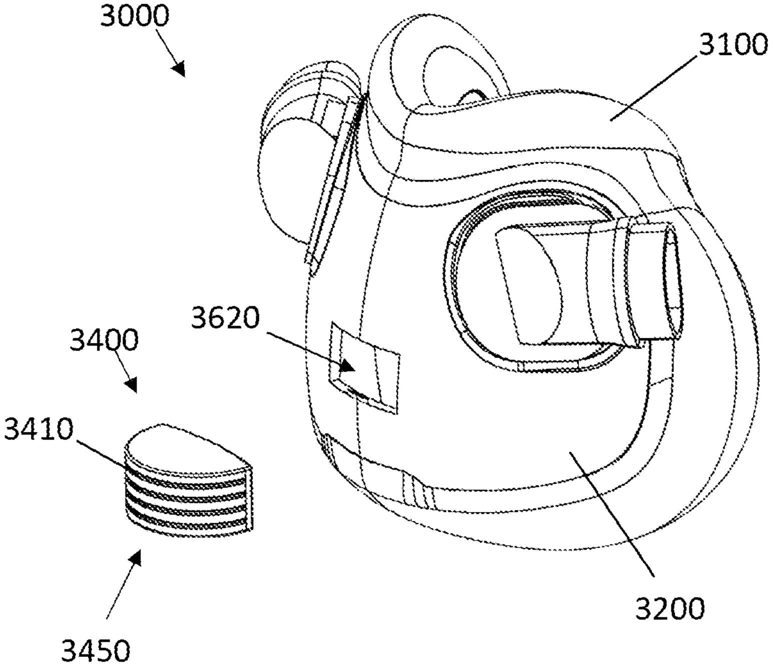

FIG. 7B shows an exploded view of the patient interface 3000 shown in FIG. 7A.

Figure 7C:
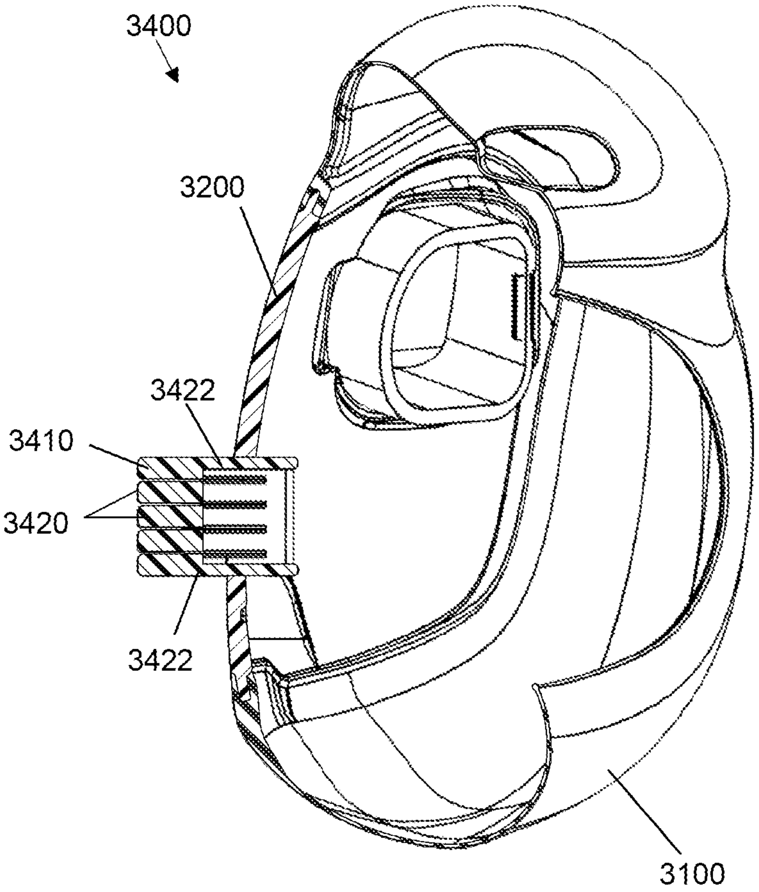

FIG. 7C shows a side cross-sectional view of the patient interface 3000 shown in FIG. 7A.

Figure 8A:
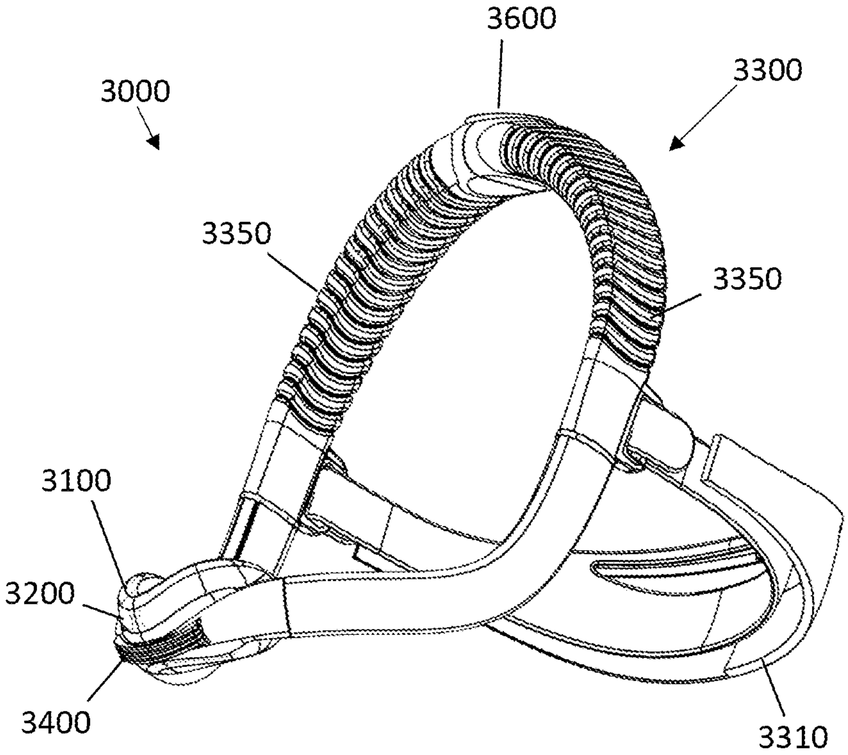

FIG. 8A shows an isometric view of a patient interface 3000 in accordance with one form of the present technology.

Figure 8B:
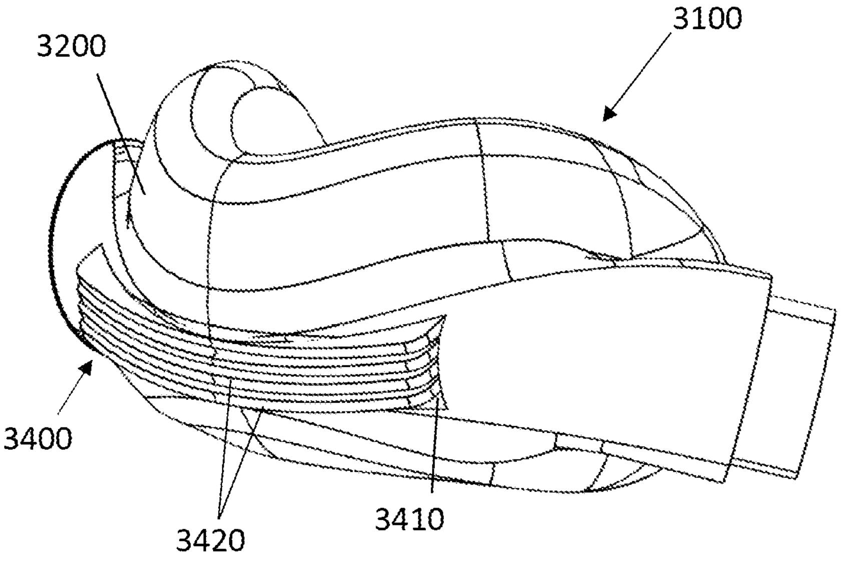

FIG. 8B shows an isometric view of part of the patient interface 3000 shown in FIG. 8A.

Figure 8C:
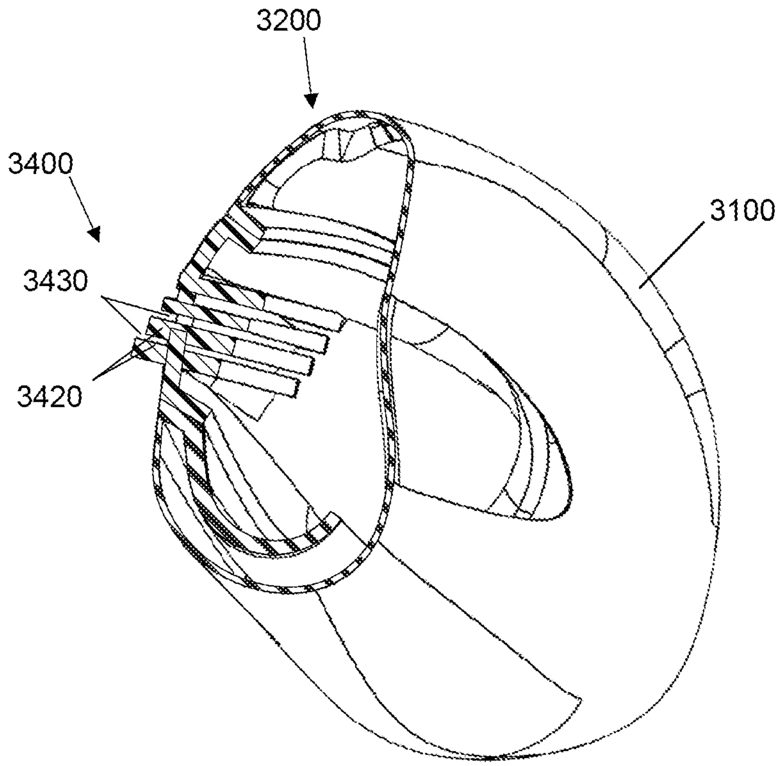

FIG. 8C shows a side cross-sectional view of the patient interface 3000 shown in FIG. 8A.

Figure 8D:
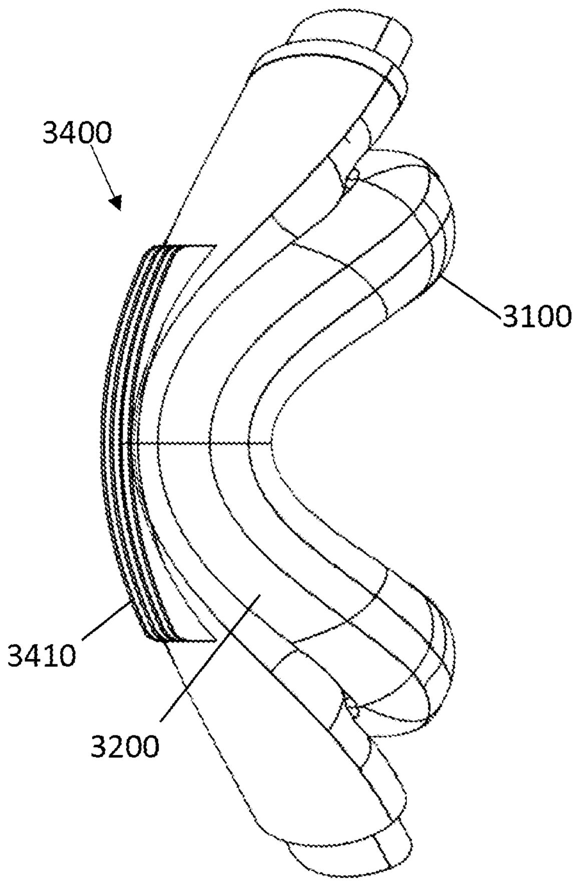

FIG. 8D shows a top view of the patient interface 3000 shown in FIG. 8A.

Figure 9A:
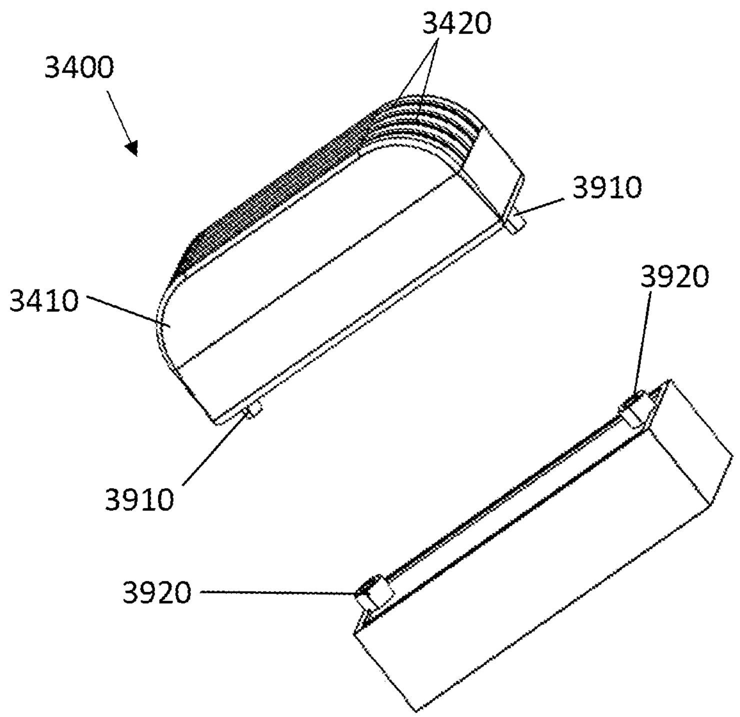

FIG. 9A shows an isometric view of a vent 3400 and heat and moisture exchanger (HME) 3900 in accordance with one form of the present technology.

Figure 9B:
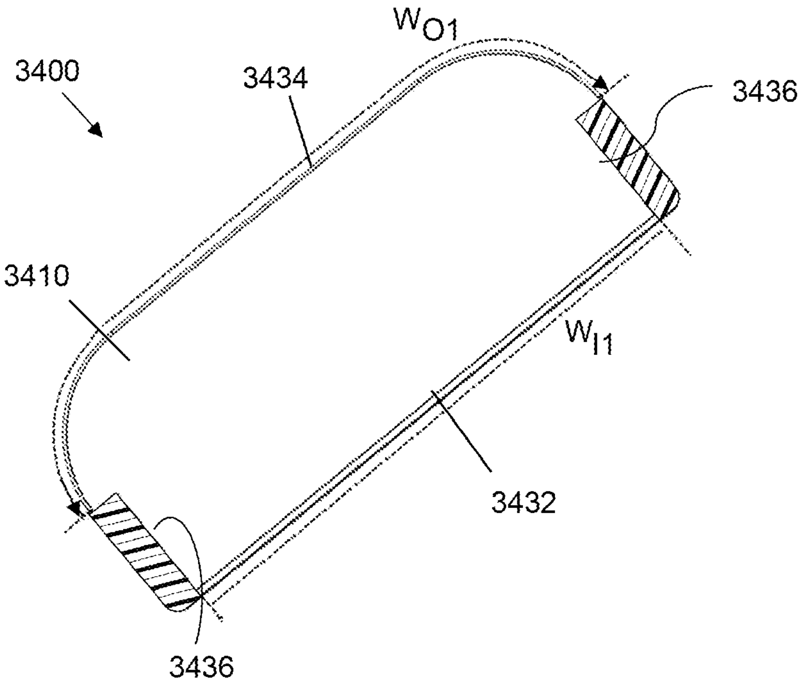

FIG. 9B shows a top cross-sectional view of the vent 3400 shown in FIG. 9A.

Figure 9C:
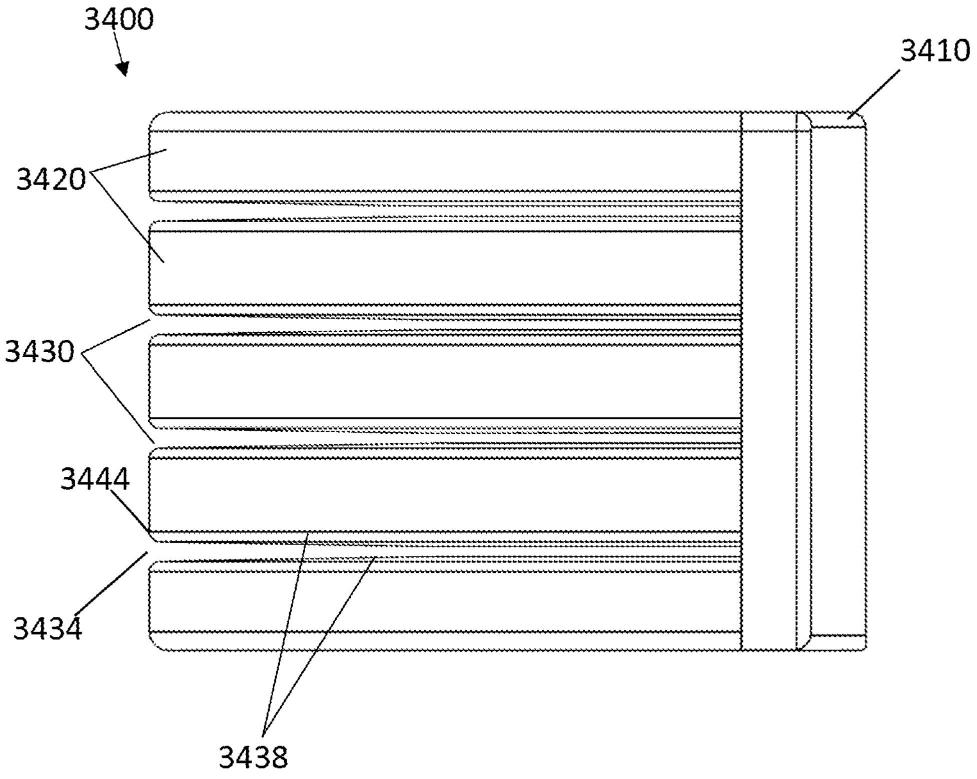

FIG. 9C shows a side view of the vent 3400 shown in FIG. 9A.

Figure 10A:
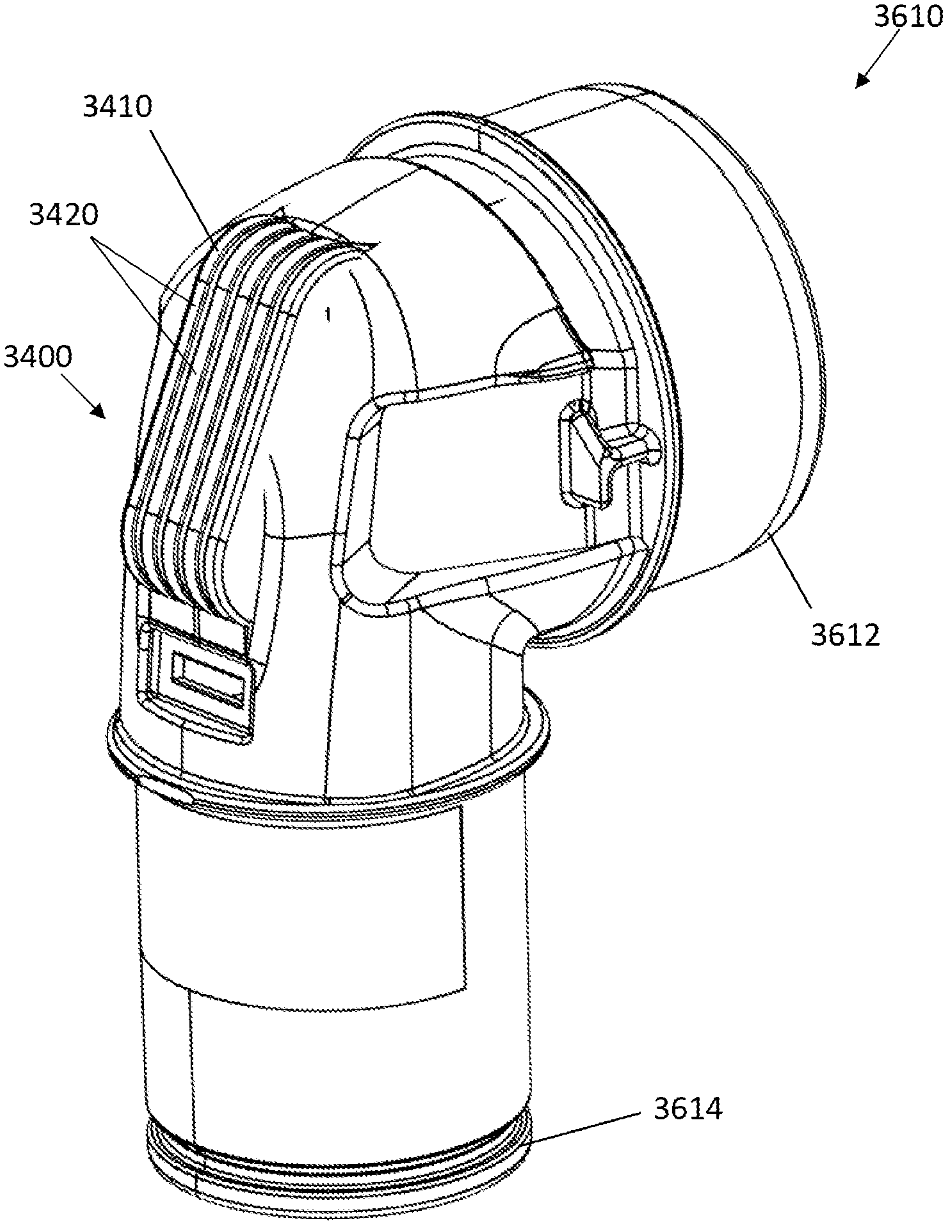

FIG. 10A shows an isometric view of an elbow 3610 in accordance with one form of the present technology. Elbow 3610 comprises the vent 3400 shown in FIGS. 9A-9C.

Figure 10B:
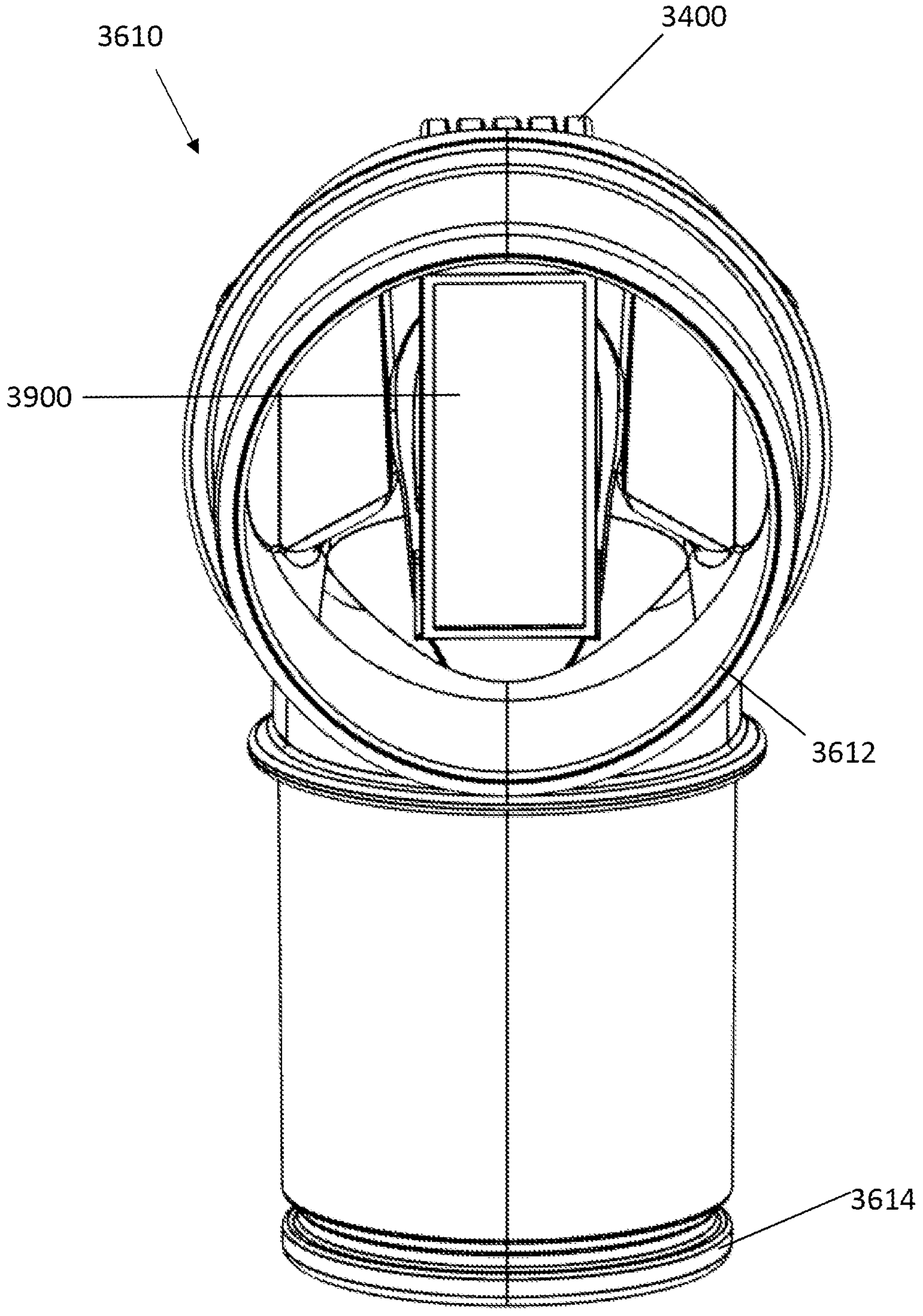

FIG. 10B shows a rear view of the elbow 3610 shown in FIG. 10A.

Figure 10C:
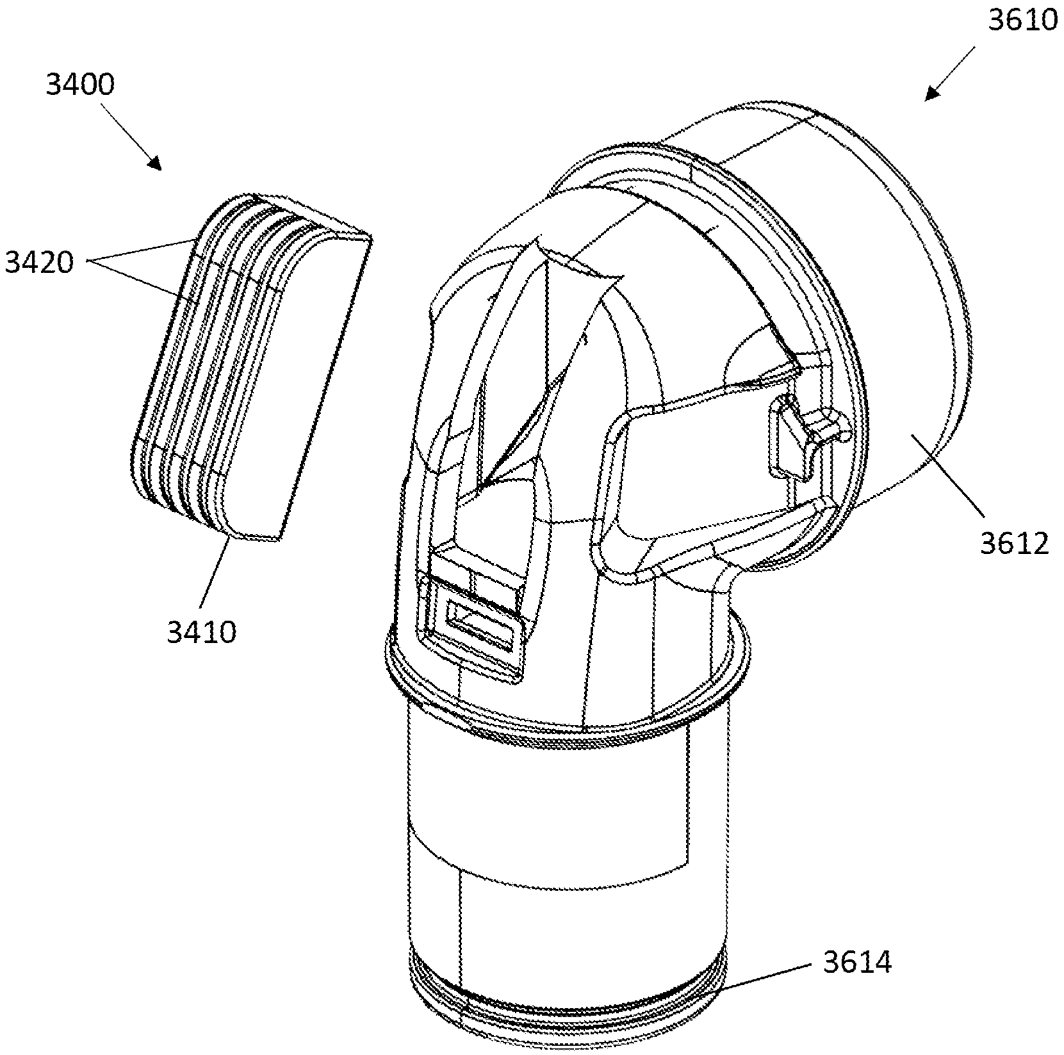

FIG. 10C shows an exploded view of the elbow 3610 shown in FIG. 10A.

Figure 10D:
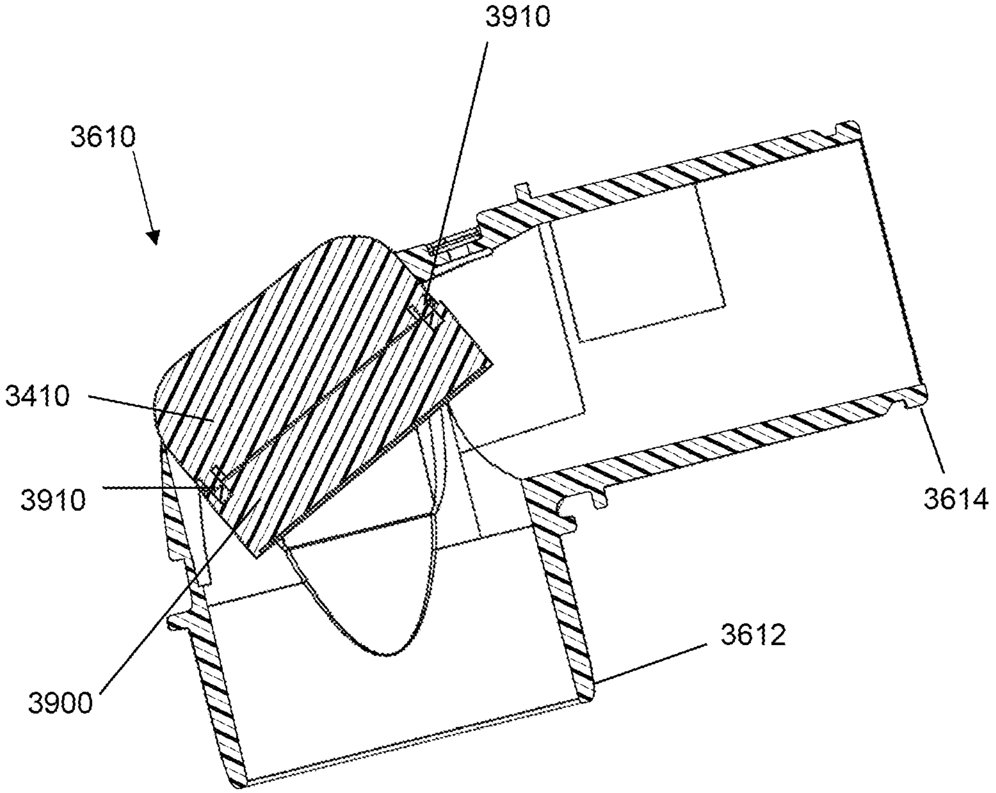

FIG. 10D shows a side cross-sectional view of the elbow 3610 shown in FIG. 10A.

Figure 11A:
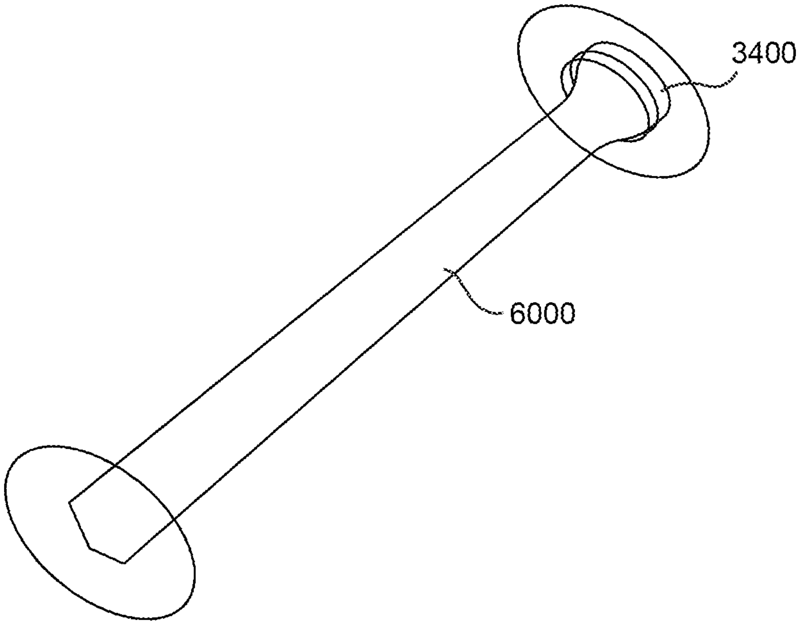

FIG. 11A shows modelled vent flow for a conventional vent having multiple circular vents.

Figure 11B:
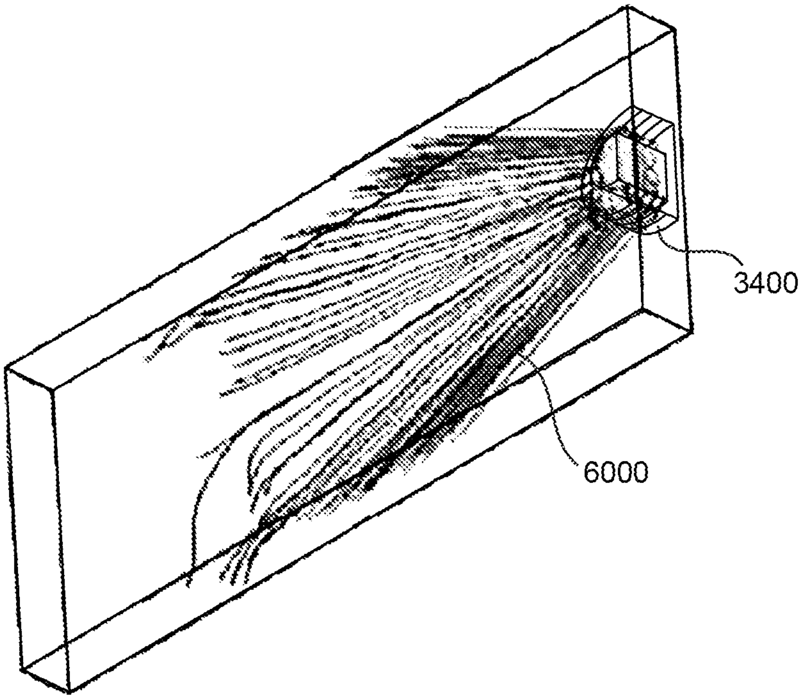

FIG. 11B shows modelled vent flow for the vent 3400 of FIGS. 4A-4D.

Figure 12:
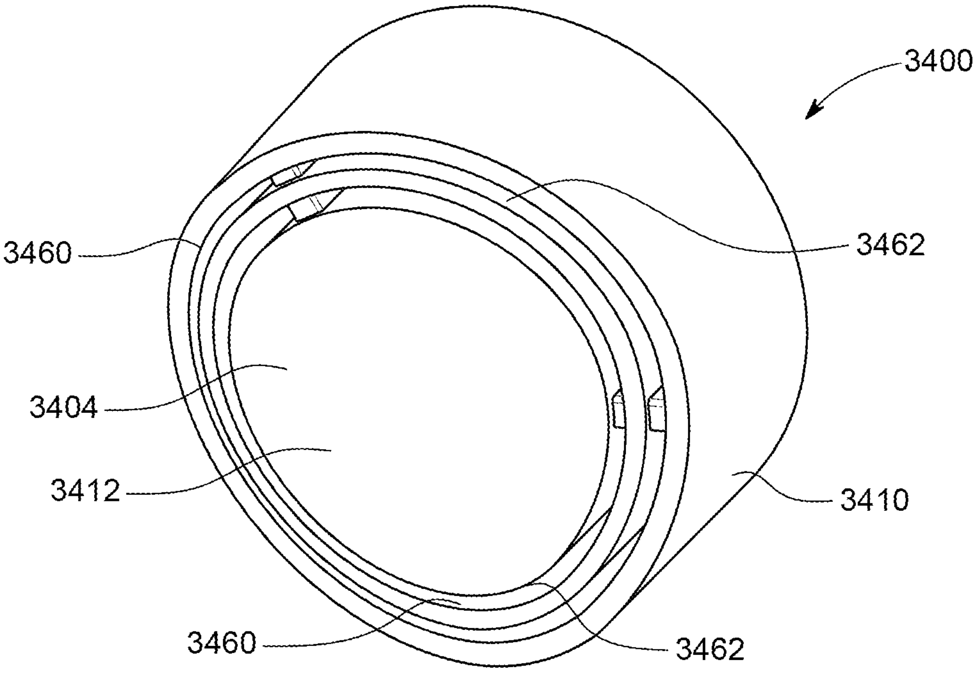

FIG. 12 is an isometric view of downstream side of a vent according to one form of the technology.

Figure 13:
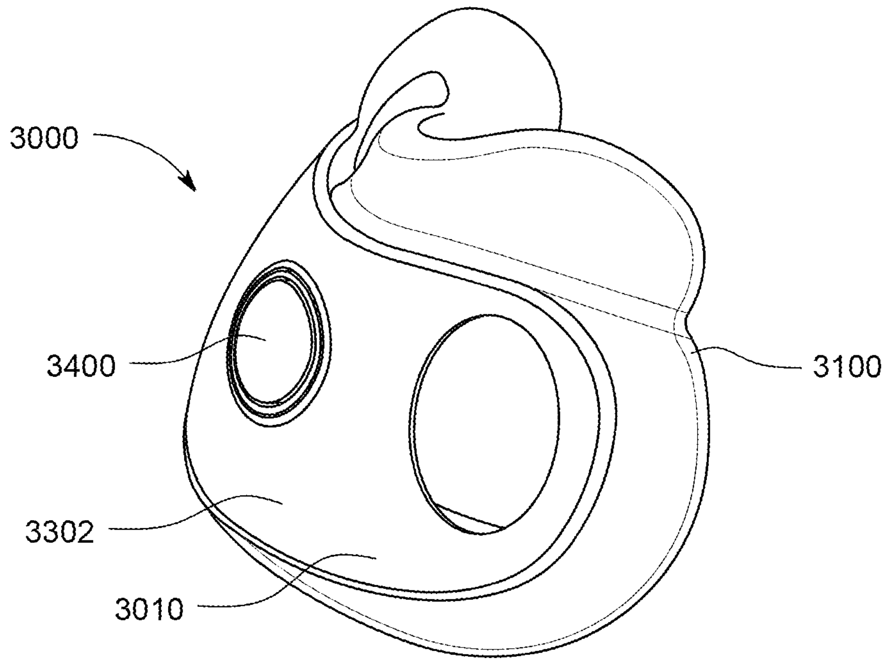

FIG. 13 is an isometric view of a non-patient facing side of a patient interface which is provided with the vent of FIG. 12.

Figure 14:
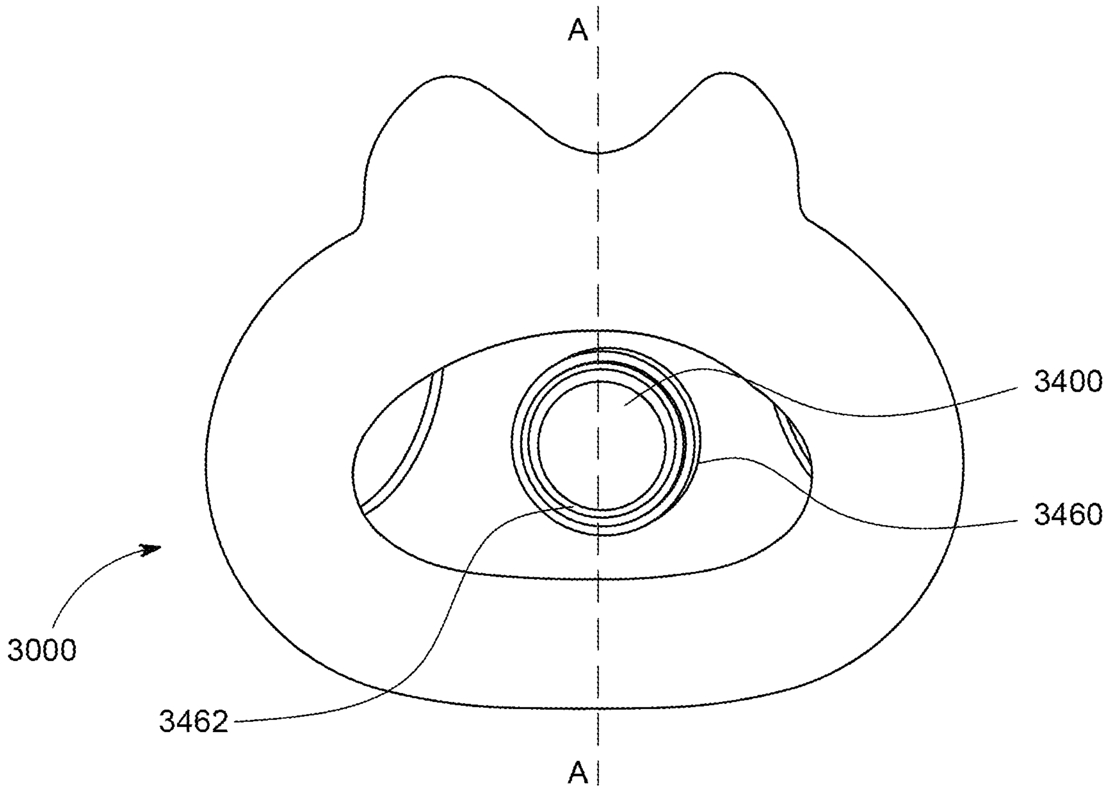

FIG. 14 is a view of the patient facing side of the patient interface of FIG. 13.

Figure 15:
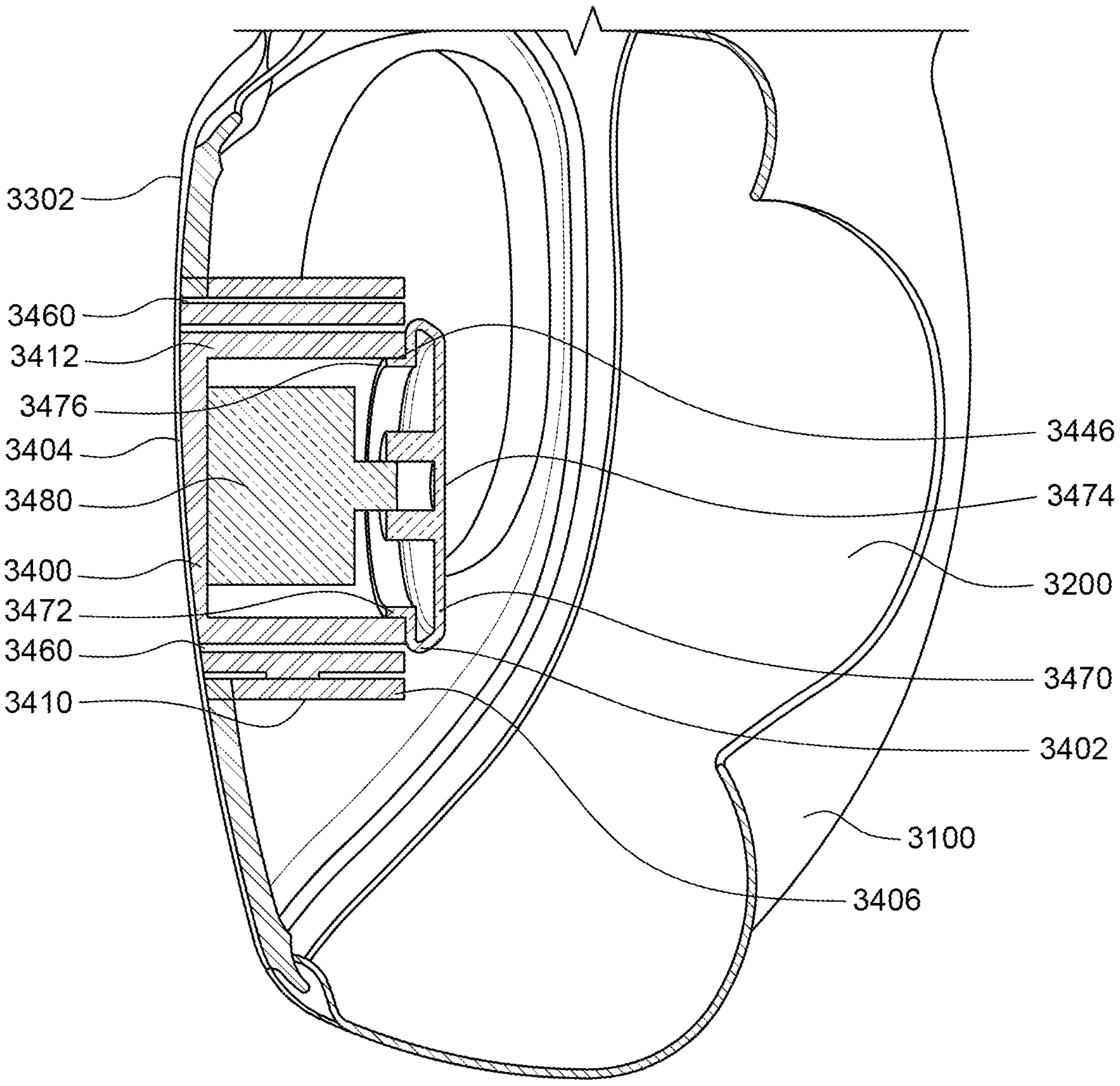

FIG. 15 is a partial cross-section view through plane A-A of FIG. 14.

Figure 16A:
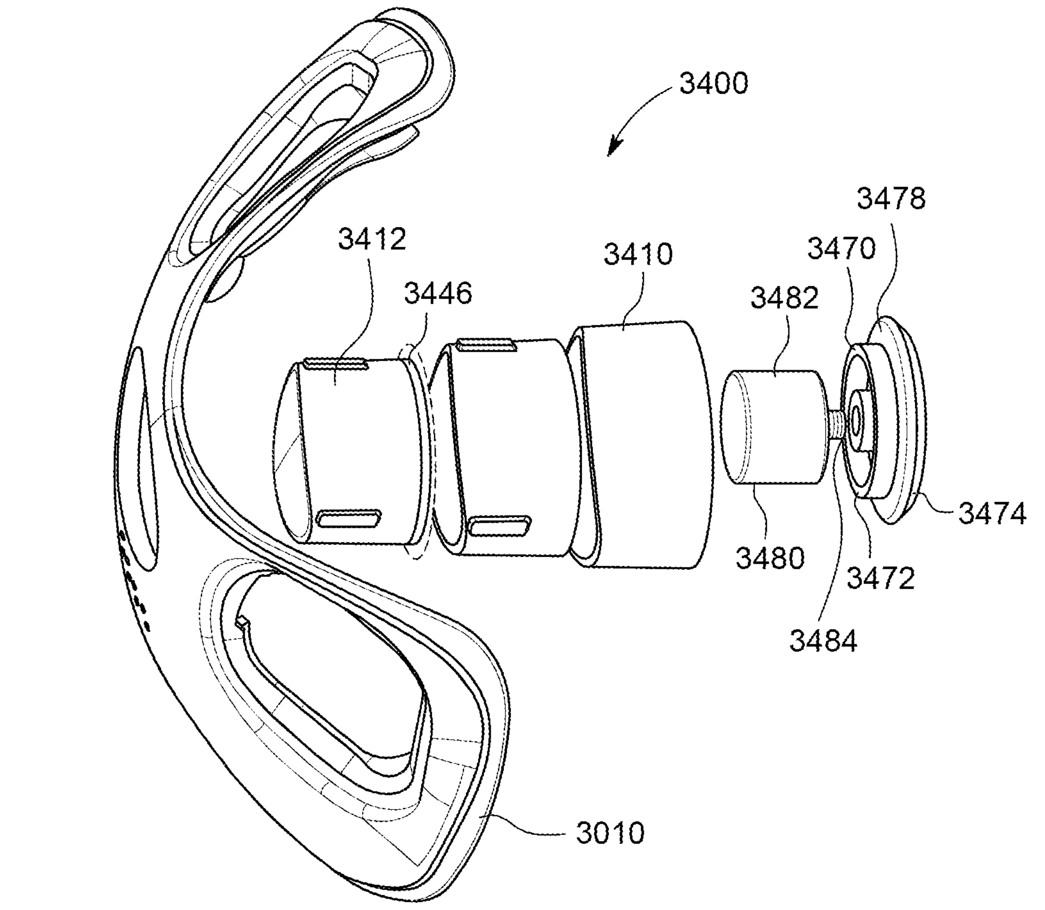

FIG. 16A is an exploded view of the frame and vent of the patient interface of FIG. 12.

Figure 16B:
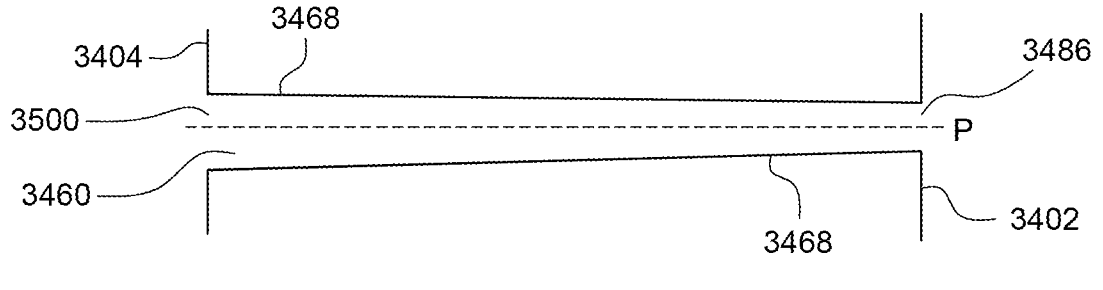

FIG. 16B is an enlarged cross section view of one flow path of the vent of FIG. 12.

Figure 17A:
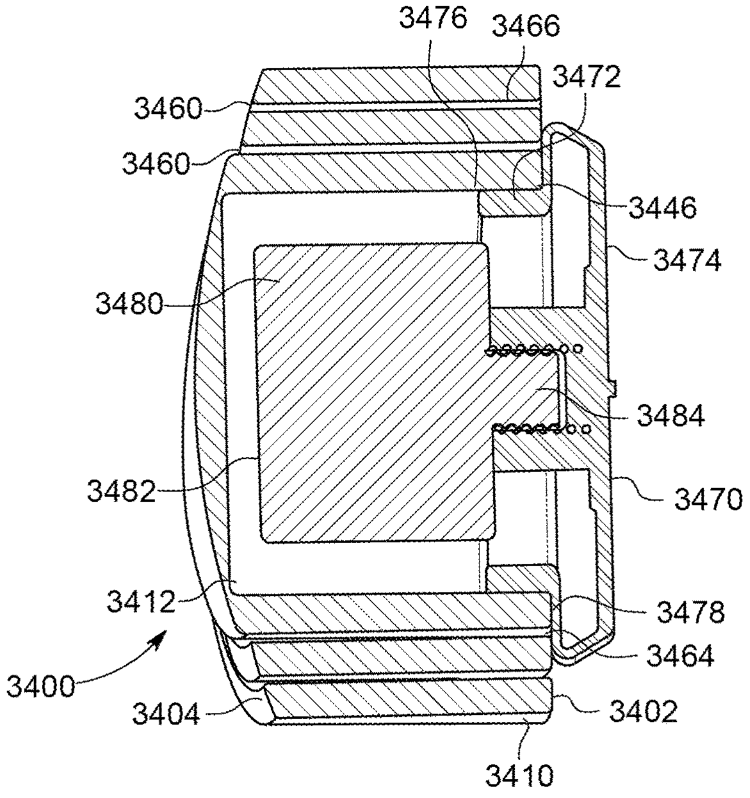
Figure 17B:
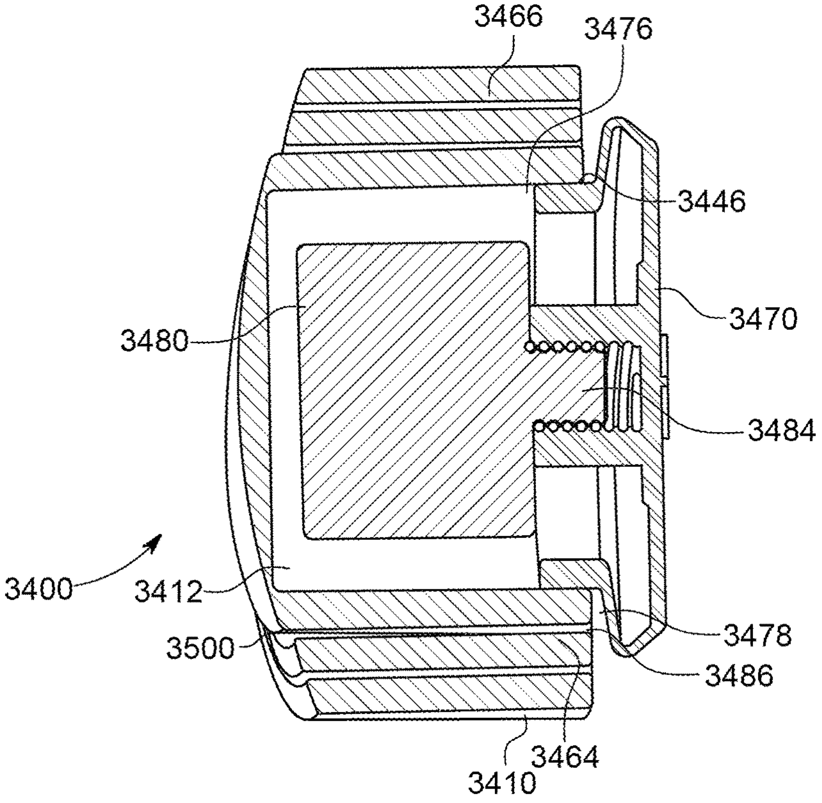

FIG. 17A is an enlarged cross section view of the vent of FIG. 12 with the vent cover in a first configuration.

17B is an enlarged cross section view of the vent of FIG. 12 with the vent cover in a second configuration.

Figure 18A:
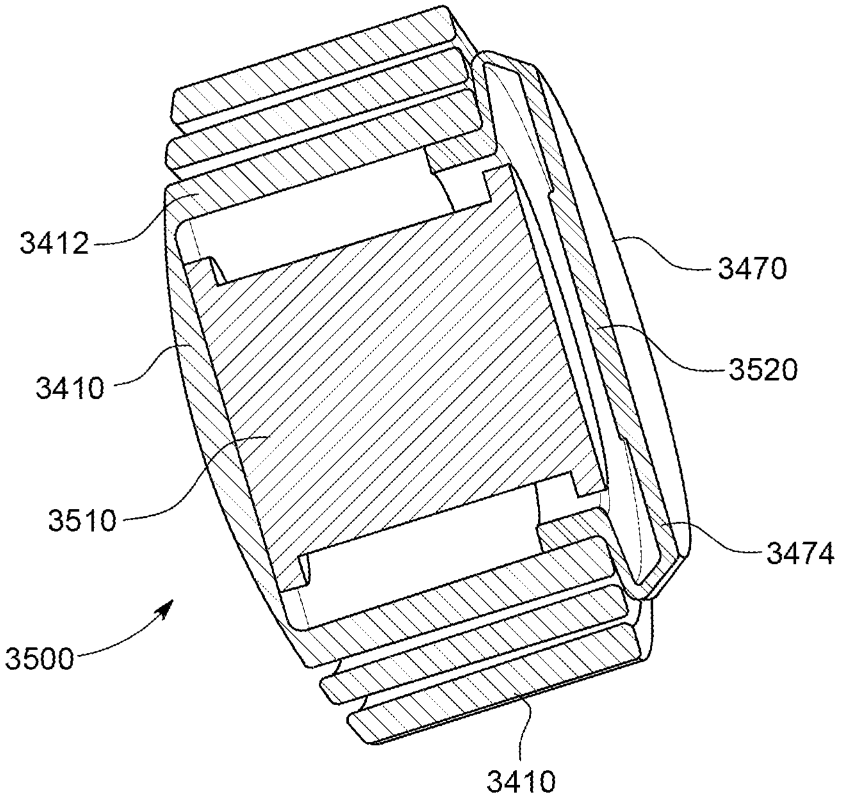

FIG. 18A is a cross-section view of a vent according to one form of the technology, with the vent cover in a first configuration.

Figure 18B:
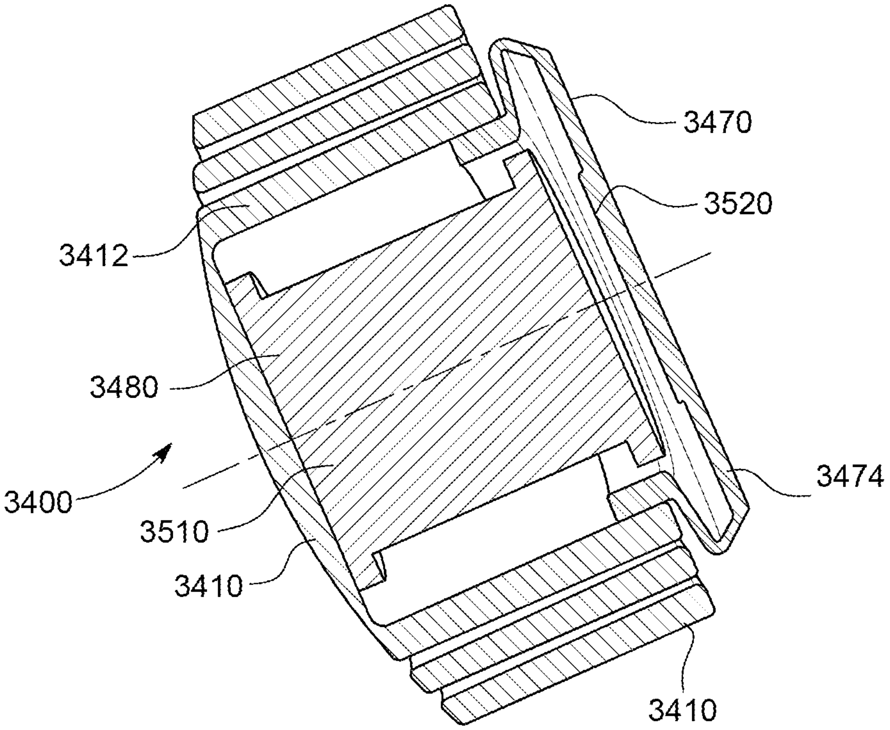

FIG. 18B is a cross-section view of the vent of FIG. 18A with the vent cover in a second configuration.

Figure 19:
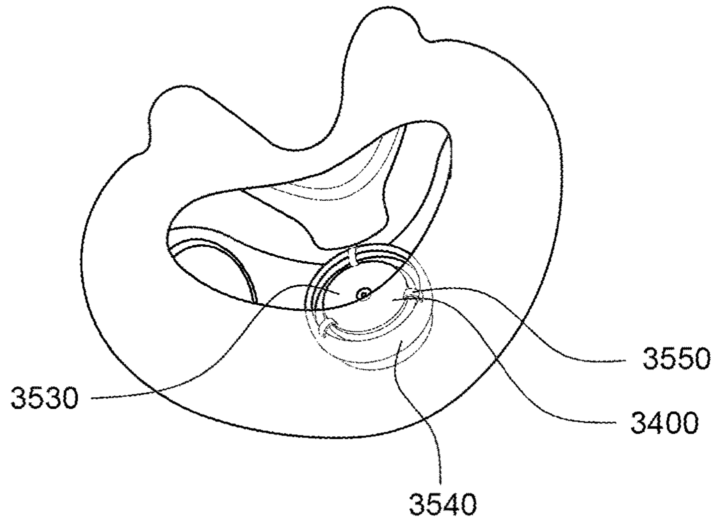

FIG. 19 is an isometric view of a patient facing side of a cushion module which is provided with a vent according to one form of the present technology.

Figure 20A:
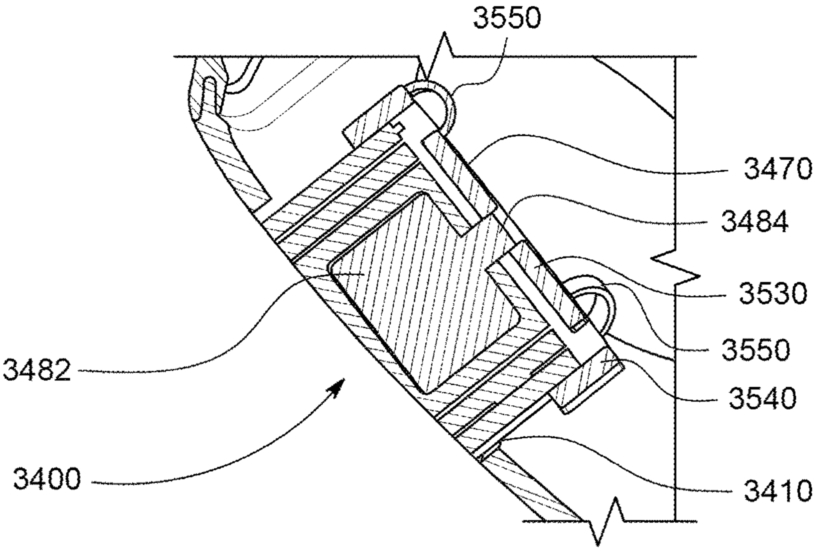

FIG. 20A is a cross-section view of the vent shown in FIG. 19 with the vent cover in a second position.

Figure 20B:
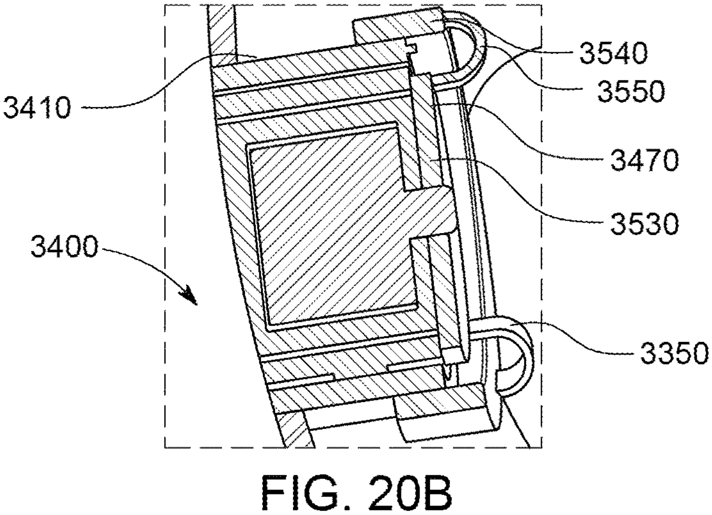

FIG. 20B is a cross-section view of the vent shown in FIG. 19 with the vent cover in a first position.

Figure 21:
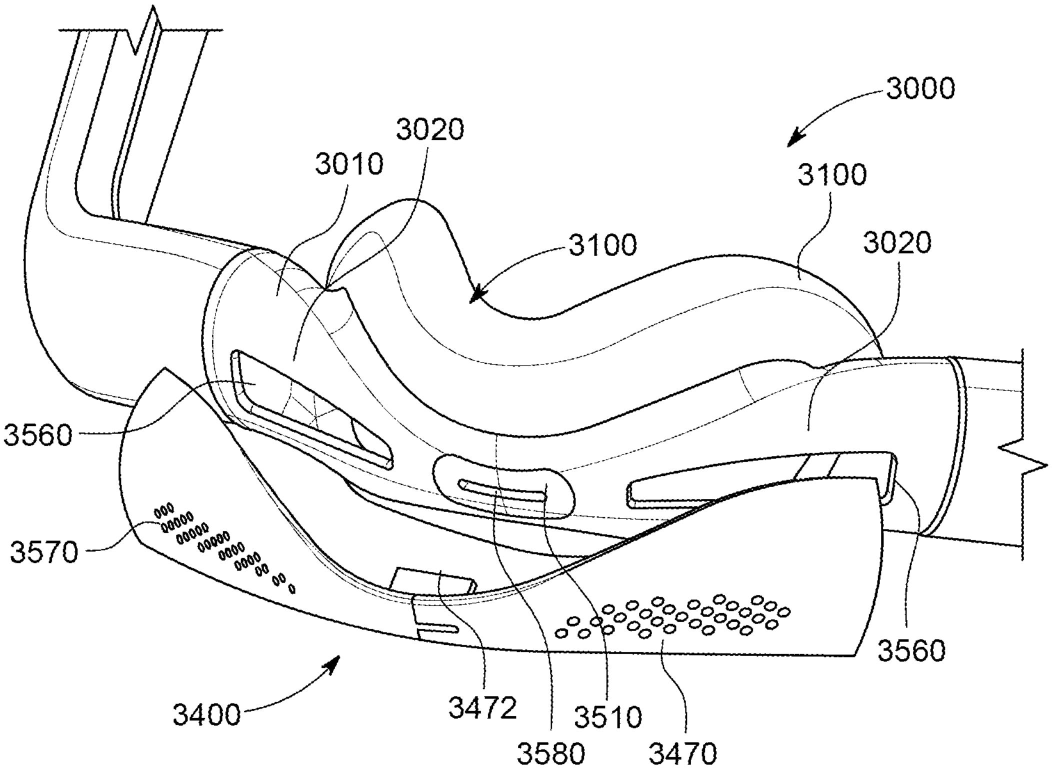

FIG. 21 is an exploded view of a patient interface according to one form of the present technology.

Figure 22:
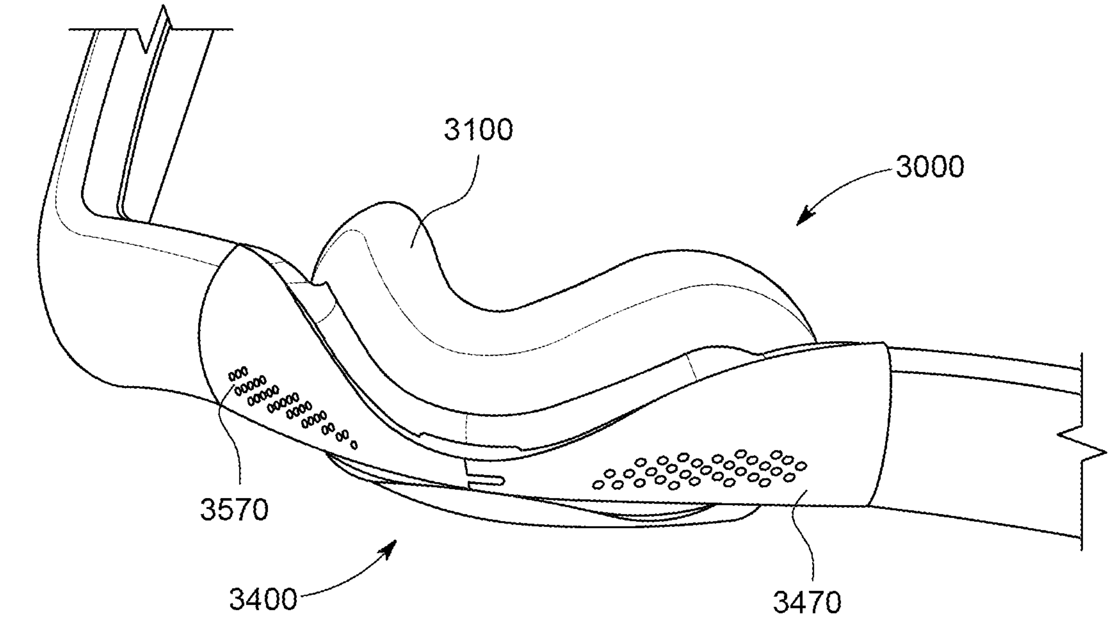

FIG. 22 is an isometric view of the non-patient facing side of the patient interface of FIG. 21 with the vent cover in a first position.

Figure 23:
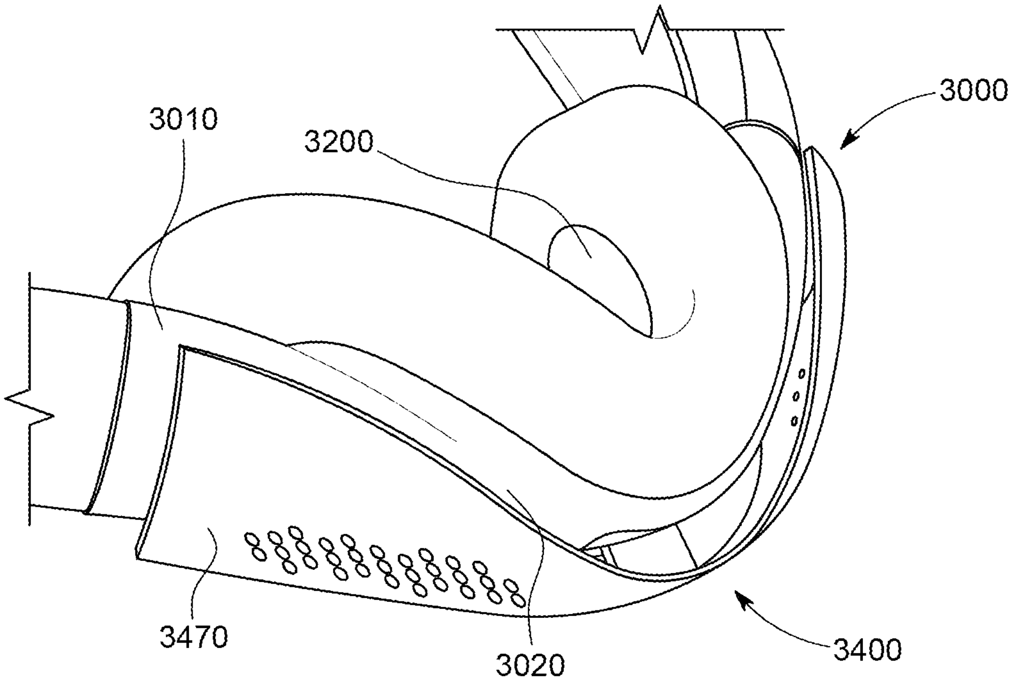

FIG. 23 is a different isometric view from the non-patient facing side and above of the patient interface of FIG. 21, with the vent cover in a second position

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Respiratory Therapy Systems

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000.

5.3 Patient Interface

Figure 2A:
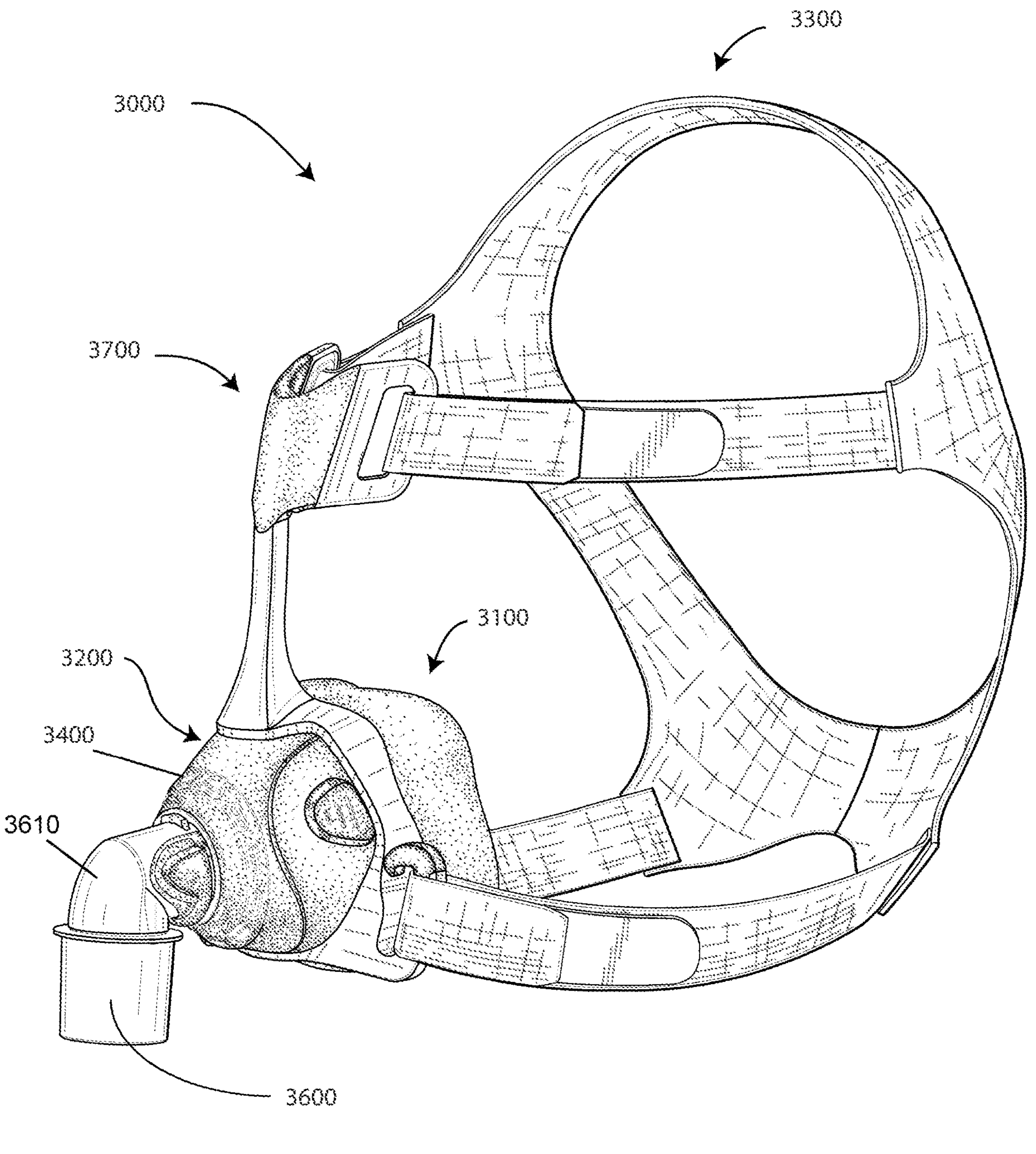

A non-invasive patient interface 3000, such as that shown in FIG. 2A, in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

Figure 1:
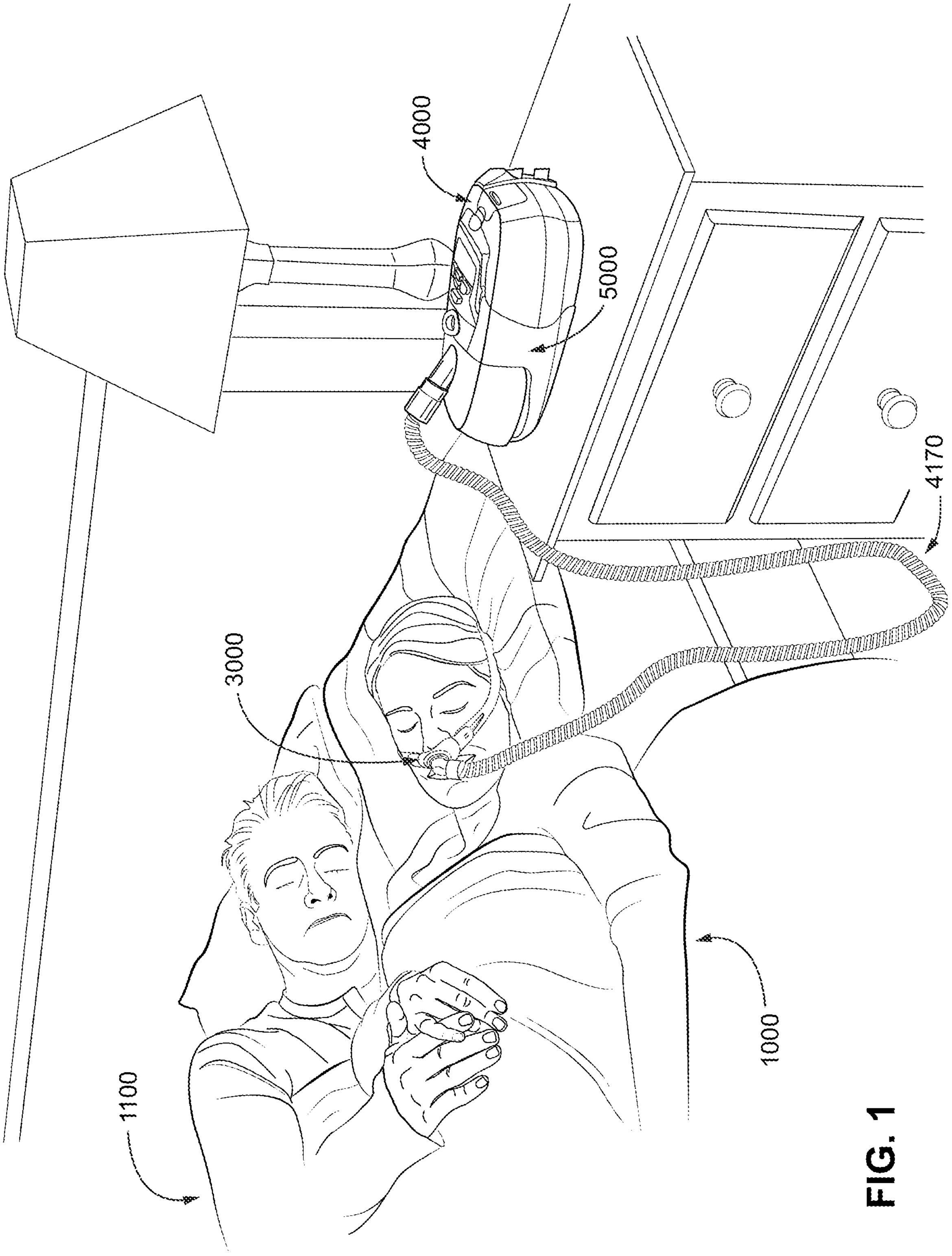
Figure 2B:
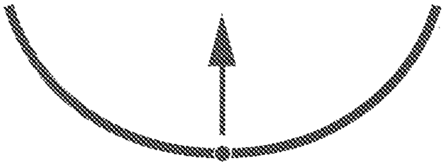
Figure 2C:
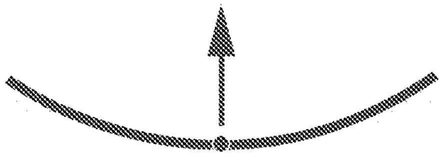
Figure 2D:
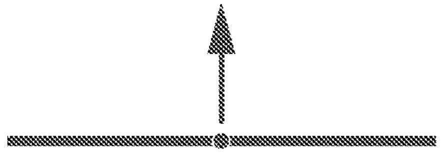
Figure 2E:
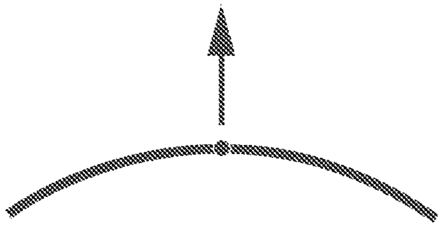
Figure 2F:
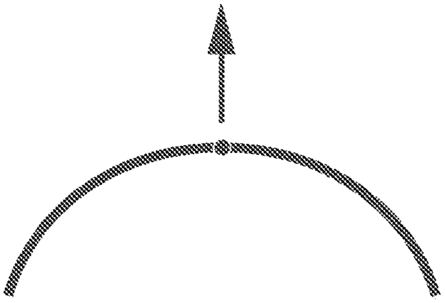
Figure 2G:
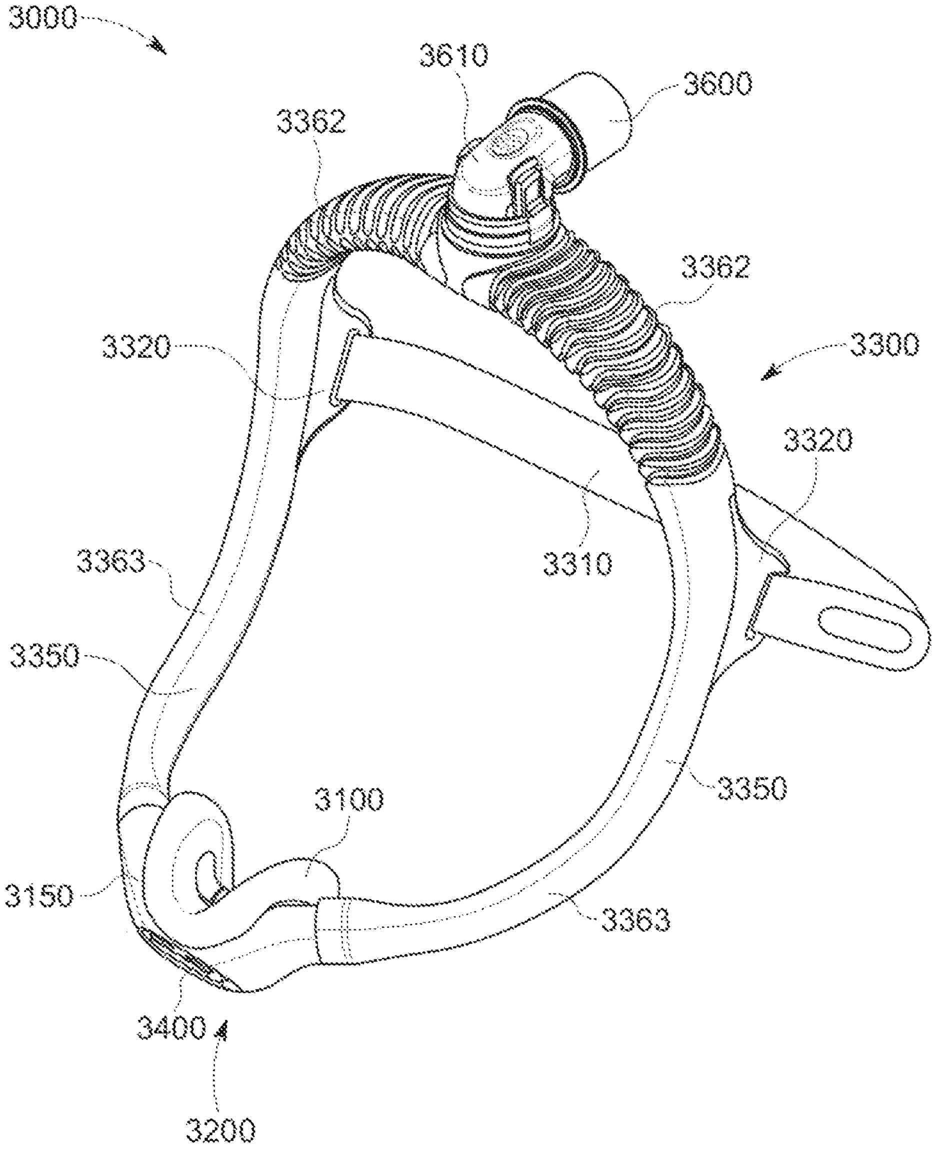

As shown in FIG. 2G, a non-invasive patient interface 3000 in accordance with another aspect of the present technology comprises the following functional aspects: a seal-forming structure 3000, a plenum chamber 3200, a positioning and stabilising structure 3300, a vent 3400 and one form of connection port 3600 for connection to an air circuit (such as the air circuit 4170 shown in FIG. 1). The plenum chamber 3200 may be formed of one or more modular components in the sense that it or they can be replaced with different components, for example components of a different size.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 $cmH_2O$ with respect to ambient.

The patient interface 3000 in accordance with one form of the present technology is constructed and arranged to be able to provide a supply of air at a positive pressure of at least 10 $cmH_2O$ with respect to ambient.

The patient interface 3000 in accordance with one form of the present technology is constructed and arranged to be able to provide a supply of air at a positive pressure of at least 20 $cmH_2O$ with respect to ambient.

In examples, the patient interface may contain sensors to measure parameters such pressure within the plenum chamber, flow rate, occurrence of apnea, humidity of gas supplied to the patent interface and/or temperature of gas supplied to the patient interface. In one example a microphone may be provided to the patient interface to detect snoring or other disordered breathing.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. The support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

5.3.1.7 Nasal Mask

In one form, the non-invasive patient interface 3000 comprises a seal-forming structure 3100 that forms a seal in use to an upper lip region (e.g. the lip superior), to the patient's nose bridge or at least a portion of the nose ridge above the pronasale, and to the patient's face on each lateral side of the patient's nose, for example proximate the patient's nasolabial sulci. The patient interface 3000 shown in FIG. 2A has this type of seal-forming structure 3100. This patient interface 3000 may deliver a supply of air or breathable gas to both nares of patient 1000 through a single orifice. This type of seal-forming structure 3100 may be referred to as a "nasal cushion" and a patient interface 3000 having such a seal-forming structure 3100 may be identified as a "nasal mask".

5.3.1.8 Full Face Mask

In one form the patient interface 3000 comprises a seal-forming structure 3100 that forms a seal in use on a patient's chin-region (which may include the patient's lip inferior and/or a region directly inferior to the lip inferior), to the patient's nose bridge or at least a portion of the nose ridge superior to the pronasale, and to cheek regions of the patient's face. This patient interface 3000 may deliver a supply of air or breathable gas to both nares and mouth of patient 1000 through a single orifice. This type of seal-forming structure 3100 may be referred to as a "full face cushion" and the patient interface 3000 may be identified as a "full-face mask".

5.3.1.9 Ultracompact Full-Face Mask

In one form the patient interface 3000 comprises a seal-forming structure 3100 that forms a seal in use on a patient's chin region (which may include the patient's lip inferior and/or a region directly inferior to the lip inferior), to an inferior and or anterior surface of the patient's pronasale and to the patient's face on each lateral side of the patient's nose, for example proximate the nasolabial sulci. The seal-forming structure 3100 may also form a seal against a patient's lip superior. A patient interface 3000 having this type of seal-forming structure may have a single opening configured to deliver a flow of air or breathable gas to both nares and mouth of a patient, may have an oral hole configured to provide air or breathable gas to the mouth and a nasal hole configured to provide air or breathable gas to the nares, or may have an oral hole for delivering air to the patient's mouth and two nasal holes for delivering air to respective nares. This type of patient interface 3000 may be known as an ultra-compact full face mask and may comprise an ultra-compact full face cushion.

5.3.1.10 Nasal Cradle Mask

In one form, for example as shown in FIG. 2G, the seal-forming structure 3100 is configured to form a seal in use with inferior surfaces of the nose around the nares. The seal-forming structure 3100 may be configured to seal around the patient's nares at an inferior periphery of the patient's nose including to an inferior and/or anterior surface of the patient's pronasale and to the patient's nasal alae. The seal-forming structure 3100 may seal to the patient's lip superior. This type of seal-forming structure 3100 may be referred to as a "cradle cushion", "nasal cradle cushion" or "under-the-nose cushion", for example.

The shape of the seal-forming structure 3100 may be configured to match or closely follow the underside of the patient's nose and may not contact a nasal bridge region of the patient's nose or any portion of the patient's nose superior to the pronasale. In one form of nasal cradle cushion, the seal-forming structure 3100 comprises a bridge portion dividing the opening into two orifices, each of which, in use, supplies air or breathable gas to a respective one of the patient's nares. The bridge portion may be configured to contact or seal against the patient's columella in use. Alternatively, the seal-forming structure 3100 may comprise a single opening to provide a flow or air or breathable gas to both of the patient's nares.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

The plenum chamber 3200 may comprise a plenum chamber inlet port configured to receive the flow of air from the air circuit 4170, either directly or indirectly via another component(s). In some forms of the technology, exhaled gas may also be vented out of the patient interface 3000 via the plenum chamber inlet port.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

In the example shown in FIG. 2G the plenum chamber 3200 is defined, at least in part, by a cushion module 3150.

5.3.3 Positioning and Stabilising Structure

The seal-forming structure 3100 of the patient interface 3000 of the present technology may be held in sealing position in use by the positioning and stabilising structure 3300. The positioning and stabilising structure 3300 may comprise and function as "headgear" since it engages the patient's head in order to hold the patient interface 3000 in a sealing position.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

5.3.3.1 Conduit Headgear 5.3.3.1.1 Conduit Headgear Tubes

In some forms of the present technology, the positioning and stabilising structure 3300 comprises one or more headgear tubes 3350 that deliver pressurised air received from a conduit forming part of the air circuit 4170 from the RPT device to the patient's airways, for example through the plenum chamber 3200 and seal-forming structure 3100. In the forms of the present technology illustrated in FIG. 2G and FIG. 8A, the positioning and stabilising structure 3300 comprises two tubes 3350 that deliver air to the plenum chamber 3200 from the air circuit 4170. The tubes 3350 are configured to position and stabilise the seal-forming structure 3100 of the patient interface 3000 at the appropriate part of the patient's face (for example, the nose and/or mouth). This allows the conduit of air circuit 4170 providing the flow of pressurised air to connect to a connection port 3600 of the patient interface in a position other than in front of the patient's face, for example on top of the patient's head.

Since air can be contained and passed through headgear tubing in order to deliver pressurised air from the air circuit 4170 to the patient's airways, the positioning and stabilising structure 3300 may be described as being inflatable. It will be understood that an inflatable positioning and stabilising structure 3300 does not require all components of the positioning and stabilising structure 3300 to be inflatable. For example, in the examples shown in FIG. 2G and FIG. 8A, the positioning and stabilising structure 3300 comprises the tubes 3350, which are inflatable, and the strap 3310, which is not inflatable.

In the forms of the present technology illustrated in FIG. 2G and FIG. 8A, the positioning and stabilising structure 3300 comprises two tubes 3350, each tube 3350 being positioned in use on a different side of the patient's head and extending across the respective cheek region, above the respective ear (superior to the otobasion superior on the patient's head) to the elbow 3610 on top of the head of the patient 1000. This form of technology may be advantageous because, if a patient sleeps with their head on its side and one of the tubes is compressed to block or partially block the flow of gas along the tube, the other tube remains open to supply pressurised gas to the patient. In other examples of the technology, the patient interface 3000 may comprise a different number of tubes, for example one tube, or three or more tubes. In one example in which the patient interface has one tube 3350, the single tube 3350 is positioned on one side of the patient's head in use (e.g. across one cheek region) and a strap forms part of the positioning and stabilising structure 3300 and is positioned on the other side of the patient's head in use (e.g. across the other region) to assist in securing the patient interface 3000 on the patient's head.

In the forms of the technology shown in FIG. 2G and FIG. 8A the two tubes 3350 are fluidly connected at superior ends to each other and to the connection port 3600. In some examples, the two tubes 3350 are integrally formed while in other examples the tubes 3350 are formed separately but are connected in use and may be disconnected, for example for cleaning or storage. Where separate tubes are used they may be indirectly connected together, for example each may be connected to a T-shaped connector having two arms/branches each fluidly connectable to a respective one of the tubes 3350 and a third arm or opening providing the connection port 3600 for fluid connection to the air circuit 4170 in use.

The tubes 3350 may be formed from a flexible material, such as an elastomer, e.g. silicone or TPE, or from one or more textile and/or foam materials. The tubes 3350 may have a preformed shape and may be able to be bent or moved into another shape upon application of a force but may return to the original preformed shape in the absence of said force. The tubes 3350 may be generally arcuate or curved in a shape approximating the contours of a patient's head between the top of the head and the nasal or oral region. The patient interface 3000 shown in FIG. 2G superior portions of the tube 3350 comprise extendable tube sections, each in the form of an extendable concertina structure 3362.

The cross-sectional shape of the non-extendable tube sections 3363 of the tubes 3350 may be circular, elliptical, oval, D-shaped or a rounded rectangle, for example as described in U.S. Pat. No. 6,044,844. A cross-sectional shape that presents a flattened surface of tube on the side that faces and contacts the patient's face or other part of the head may be more comfortable to wear than, for example a tube with a circular cross-section.

As described above, in some examples of the present technology the patient interface 3000 comprises a seal-forming structure 3100 in the form of a cradle cushion which lies generally under the nose and seals to an inferior periphery of the nose (e.g. an under-the-nose cushion). The positioning and stabilising structure 3300, including the tubes 3350 may be structured and arranged to pull the seal-forming structure 3100 into the patient's face under the nose with a sealing force vector in a posterior and superior direction (e.g. a posterosuperior direction). A sealing force vector with a posterosuperior direction may facilitate the seal-forming structure 3100 forming a good seal to both the inferior periphery of the patient's nose and the anterior-facing surfaces of the patient's face on either side of the patient's nose and the patient's lip superior.

5.3.3.1.2 Conduit Headgear Straps

In certain forms of the present technology, the positioning and stabilising structure 3300 comprises at least one headgear strap acting in addition to the tubes 3350 to position and stabilise the seal-forming structure 3100 at the entrance to the patient's airways. As shown in FIG. 2G and FIG. 8A, the patient interface 3000 comprises a strap 3310 forming part of the positioning and stabilising structure 3300. The strap 3310 may be known as a back strap or a rear headgear strap, for example. The strap may be connected to tabs 3320 provided to the tubes 3350. In other examples of the present technology, one or more further straps may be provided. For example, patient interfaces 3000 according to examples of the present technology having a full face cushion may have a second, lower, strap configured to lie against the patient's head proximate the patient's neck and/or against posterior surfaces of the patient's neck.

5.3.4 Vent

In one form, the patient interface 3000 includes a vent 3400 constructed and arranged to allow for a vent flow of gases exhaled by the patient 1000 from a volume interior to the respiratory therapy system, for example from the plenum chamber 3200, to ambient. The vent flow of exhaled gases may be referred to as the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent is capable of allowing a vent flow rate which is sufficient to reduce rebreathing of exhaled $CO_2$ by the patient while maintaining the therapeutic pressure in the plenum chamber in use.

An exemplary vent 3400 according to one form of the technology is illustrated in FIGS. 4A-4D. Other parts of the respiratory therapy system of which vent 3400 is part are not illustrated in these figures. Vent 3400 is configured to allow vent flow from a volume 3490 on one side of the vent 3400 to a region of ambient air 3492 (referred to as "ambient" 3492) on the other side. In use in a respiratory therapy system, the volume 3490 forms part of, or is fluidly connected to, the interior of the plenum chamber 3200.

Forms of vent 3400 provided in other forms of the technology are illustrated in FIGS. 6A-10D and 12-23. The various forms of vent 3400 illustrated in these figures will now be described by way of non-limiting examples.

5.3.4.1 Vent Body

In certain forms of the technology, vent 3400 comprises a vent body 3410.

Vent body 3410 may comprise a plurality of plates 3420 arranged such that the plates 3420 are oriented substantially in parallel to each other and the plates 3420 are spaced apart in a direction perpendicular to the faces of the plates. By arranging the plates 3420 in a spaced array in this way, a slot 3430 is formed between each pair of the plates and the vent body 3410 has formed therein a plurality of slots 3430. As will be described below, these slots 3430 act to allow the flow of gas through the vent 3400. The plates 3420 comprise side walls 3438 and the slots 3430 are formed between side walls of adjacent plates 3420.

In certain forms of the technology, such as shown in FIGS. 4A-7C and 9A-10D, the plates 3420 are equally sized and arranged such that their end walls are aligned. In other forms, such as shown in FIGS. 8A-8D, the plates 3420 are equally sized and arranged such that their end walls are offset from each other in a direction parallel to a plane of the faces of the plates. The amount of offset may be the same between each pair of adjacent plates, or the amount of offset may differ between pairs of adjacent plates. In still other forms, one or more of the plurality of plates may differ in size from any one or more other of the plurality of plates.

The vent body 3410 may further comprise one or more plate-holding member(s), for example a frame, to hold the plates 3420 in the described arrangement. An inner facing surface of the plate-holding member(s) may form an end wall 3436 of a slot 3430.

In some forms, such as illustrated in FIGS. 4A-4D, 6A-6D and 9A-9C, vent body 3410 may be formed in one piece as a single component, where that component comprises the plurality of plates 3420 and the plate-holding member(s) integrally formed together. In such forms, vent body 3410 may be formed through a moulding process, for example injection moulding. In the exemplary form shown in these figures, the vent body 3410 is moulded such that the slots 3430 do not extend to the edges of the vent body 3410. In this case, the plate-holding members may be considered to be the regions of material at the ends of the vent body 3410 that extend from the top to the bottom of the vent body 3410.

In other forms, the plurality of plates 3420 and the plate-holding member(s) may be separate components that are assembled together to form vent body 3410.

In certain forms of the technology, vent body 3410 is formed from a plastics material, for example polycarbonate. In other forms, vent body 3410 is formed from an elastomer, for example silicone. It is desirable for vent body 3410 to be formed from a material and in a shape that the vent body 3410 is sufficiently rigid to maintain the size and shape of the slots formed therein when subject to forces that would be usually encountered during normal use.

Vents 3400 according to certain forms of the technology may be formed from a vent body 3410 integrally formed as a single component. Consequently, the vents may be easily made using a moulding process, for example injection moulding.

5.3.4.1.1 Surface Finish of Vent Body in Slot

The surface finish of the parts of the vent body 3410 contacting gas travelling through the slots 3430 (i.e. the end walls 3436 and side walls 3438) affects the amount of turbulence created in the vent flow of gas through the vent 3400. It is generally desirable for the surface finish to be of a type that generates as little turbulence as possible.

In some forms of the technology, the surface of the end walls 3436 and/or the side walls 3438 are substantially smooth. For example, the surfaces may be polished during the manufacture process, or otherwise manufactured using a technique to provide as smooth a surface as possible for the material used to form vent body 3410.

In other forms of the technology, the surface of the end walls 3436 and/or the side walls 3438 comprise a texture that is configured to generate a relatively small amount of turbulence (i.e. to promote laminar flow) in gas flowing passed the surface when compared to more turbulence-inducing surface finishes. As discussed in more detail below, a vent flow that is more laminar in nature is advantageous as less noise is produced compared to vent flow that is more turbulent in nature. In one exemplary form of the technology, the surface of the end walls 3436 and/or the side walls 3438 is structured to comprise a 'shark-skin' finish. In such a form, a plurality of small denticles are provided on the surface of the vent body 3410. Such surface textures may reduce drag, and consequently turbulence, in fluid flow across a surface in some circumstances.

In certain forms of the technology, the vent body 3410 may be configured such that the surface of the end walls 3436 and/or the side walls 3438 are hydrophobic. For example, the parts of the vent body 3410 forming these walls may be formed from a material having hydrophobic properties. Alternatively, the parts of the vent body 3410 forming these walls may have a hydrophobic coating applied to them. The hydrophobic property helps to prevent water accumulating on the walls of the vent slots 3430 where the water (e.g. condensation) can block the vent flow of air through the slots. In other forms, the end walls 3436 and/or side walls 3438 of the vent body 3410 may be provided with a surface finish that causes the material to act in a hydrophobic manner. For example, a roughened finish may reduce the attraction of the surface to water particles and/or the surface tension of water on the surface, and consequently deter the accumulation of water. In some forms, such a finish may be achieved by using electrical discharge machining (EDM) as part of the process of moulding a plastics material such as polycarbonate or polytetrafluoroethylene (PTFE). It will be appreciated that the benefits of reduced water accumulation caused by a roughened surface need to be weighed against any tendency that such a finish may have to increasing turbulence in the vent flow of air.

5.3.4.2 Slots

Vent body 3410 may have formed therein a plurality of slots 3430 through which exhaled gases can pass in order to vent out of the respiratory therapy system. Slots 3430 are holes that pass through vent body 3410 from one surface of the vent body to another. Additionally, slots 3430 may be holes which have a shape in cross-section (i.e. when looking into the hole) that extend significantly further in one direction than in another direction, as will be described in more detail below.

It will be appreciated that slots 3430 are openings formed in vent body 3410. Therefore the form of slots 3430 is defined by virtue of the shape of vent body 3410. Even if not explicitly described herein, it will be understood that any described shape, feature or configuration of any one of the plurality of slots 3430 is effected by virtue of the vent body 3410 being formed in the appropriate way to create that shape, feature or configuration of the slot 3430.

Certain features of the slots 3430 according to certain forms of the technology are described with reference to FIG. 4C, which is a front view, and FIGS. 4B and 4D, which are cross-sectional view illustrations, of the vent 3400 shown in FIG. 4A. FIG. 4B shows a top cross-section taken along lines A-A shown in FIGS. 4C and 4D. It is noted that lines A-A pass through one of the slots 3430. FIG. 4D shows a side cross-section taken along lines B-B shown in FIGS. 4B and 4C.

Each slot 3430 has an inlet 3432 and an outlet 3434. The inlet 3432 allows gases, for example gases exhaled by a patient 1000, in volume 3490 to enter the respective slot 3430. The outlet 3434 allows gases to exit the slot 3430 to ambient 3492. Consequently, during normal use of vent 3400, the vent flow of gases is in the direction from the inlet 3432 to the outlet 3434. Arrows F in FIGS. 4B-4D show the general direction of the vent flow of exhaled gases through the vent 3400. These arrows are merely for illustration purposes and arrows are not shown through all slots 3430 nor in all directions that vent flow would occur.

5.3.4.2.1 Dimensions of Slots

Each slot 3430 has a length. In general terms, the length of a slot 3430 is a measure of the distance that a packet of gas travels through the slot from the inlet 3432 to the outlet 3434. In some forms, the length of a slot 3430 may be considered to be a perpendicular distance through the slot between the inlet 3432 and the outlet 3434. In other forms, the length of a slot may be considered to be a different measure of the longitudinal extent of the slot and/or the distance along which a packet of gas travels. In some forms, such as is the case with the vent 3400 shown in FIGS. 4A-4D and 6A-6D, the vent body 3410 is configured so that the length of a slot 3430 is substantially the same in all parts of the slot, for example across the entire width of the slot. For example, in FIG. 4B, the vent 3400 has lengths $L_1$, $L_2$ and $L_3$ where lengths $L_1$ and $L_3$ are the lengths of the slot 3430 in an end region proximate the ends of the slot (i.e. proximate end walls 3436) and length $L_2$ is a length of the slot 3430 in a middle region, where 'middle' in this context is considered in a direction along a width of the slot. In the example of FIG. 4B, the lengths $L_1$, $L_2$ and $L_3$ are substantially equal. In other forms, such as is the case with the vent 3400 shown in FIGS. 9A-9C, the length of a slot varies in different parts of the slot, for example, $L_1$, $L_2$ and $L_3$ may differ. Unless the context indicates otherwise, terms relating to length, such as "long" and "short", when used to describe a vent slot, will be understood to relate to the length of the slot as described above.

Each slot 3430 has a width. In general terms, the width of a slot 3430 is a measure of the distance the slot extends in one direction that is perpendicular to a length of the slot. In some cases the length of the slot 3430 may extend in different directions in different parts of the slot 3430. For example, in the case of the slots 3430 of the vent 3400 shown in FIG. 4B, the lengths $L_1$, $L_2$ and $L_3$ extend in three different directions. A width of the slot may be considered to be a distance that the slot extends in a direction perpendicular to all of these lengths which, in the case of the slots 3430 of the vent 3400 in FIG. 4B, is the distance $W_{I1}$ along the curved path of the inlet 3432 and/or the distance $W_{O1}$ along the curved path of the outlet 3434. Considered this way, the width of the slot is a distance that the slot extends from an end wall 3436 at one end of the slot to an end wall 3436 at another end of the slot. Alternatively, a width of the slot may be considered to be a distance that the slot extends in a direction perpendicular to the direction of one of these lengths, for example the length $L_2$ at the centre of the width of the slot. In the case of the slots 3430 of the vent 3400 in FIGS. 4B and 4C, the width may be the distance $W_{I2}$ that is the lateral extent of the inlet in a direction perpendicular to the direction of length $L_2$ and/or the distance $W_{O2}$ that is the lateral extent of the outlet in a direction perpendicular to the direction of length $L_2$. Forms of the technology provide vents 3400 in which the width of the slot 3430 differs between the inlet 3432 and the outlet 3430, and may also differ in between the inlet and the outlet. Unless the context indicates otherwise, terms relating to width, such as "wide" and "narrow", when used to describe a vent slot, will be understood to relate to the width of the slot as described above.

Each slot 3430 has a height. In general terms, the height of a slot 3430 is a measure of the distance the slot extends in one direction that is perpendicular to a length of the slot. The height also extends in a direction that is perpendicular to a width of the slot. The height of a slot 3430 may vary along a length of the slot and/or along the width of the slot. For example, in the case of the slots 3430 of the vent 3400 illustrated in FIG. 4D, the slots 3430 have a height $H_I$ at the slot inlet 3432 and a height $H_O$ at the slot outlet 3434. The height $H_I$ may differ from the height $H_O$. The slots 3430 may also have other heights in between the inlet and outlet. The height of a slot may be considered to be a distance that the slot spans from a side wall 3438 at the 'top' of the slot to a side wall 3438 at the 'bottom' of the slot. Unless the context indicates otherwise, terms relating to height, such as "tall" and "low", when used to describe a vent slot, will be understood to relate to the height of the slot as described above.

In the following sections there is described the relationship between certain dimensions of the slots 3430 for vents 3400 of certain forms of the technology. It will be appreciated that the specific dimensions of the slots 3430, and the relationships between them, may be varied in different forms of the technology.

It has also been explained that the vent body 3410 may be integrally formed by a moulding process. The configuration of the vent body 3410 means that set-up of the moulding apparatus can be easily changed to alter the diameter of the slots 3430, making it easy to fine tune the configuration of the vent body 3410 during the manufacture process if changes are required.

5.3.4.2.1.1 Width Compared to Height

In certain forms of the technology, such as those illustrated in FIGS. 6A-10D, the vent body 3410 is configured so that the slots 3430 are wide and low, i.e. slit-like. That is, the width of each slot is significantly greater than the height of each slot. In the case of slots in which there are multiple measures of the width of the slot and/or multiple measures of the height of the slot, it may be the case that any one width of the slot is significantly greater than any one height of the slot. In some forms of the technology it may additionally be the case that all widths of the slot are significantly greater than all heights of the slot. For example, in the case of the vent 3400 illustrated in FIGS. 4A-4D, all of the widths $W_{I1}$, $W_{O1}$, $W_{I2}$, and $W_{O2}$ are significantly greater than both of the heights $H_I$ and $H_O$. Consequently, each slot has a volume that may be approximately considered to be flat, or planar, in shape.

In some forms of the technology, a slot 3430 having a width that is significantly greater than the height may be considered to be a slot in which the ratio of a width to a height is at least approximately 15.

It will be appreciated that the absolute values of the height and width of the slots 3430 may vary according to a number of factors, including: the position of the vent 3400 within the respiratory therapy system; the number of slots 3430 in the vent 3400; and the desired vent flow of exhaled gases for a given pressure of gas inside the respiratory therapy system (for example, inside volume 3490).

By way of example, the widths of the vent 3400 may be in the range 10-50 mm and the heights of the vent 3400 may be in the range 0.2-0.8 mm. In the case of the vent 3400 illustrated in FIGS. 6A-6D, the marked widths and heights are approximately: $W_{I1}$=19 mm, $W_{O1}$=38 mm, $W_{I2}$=12 mm, $W_{O2}$=24 mm, $H_1$=0.2 mm and $H_O$=0.4 mm. In the case of the vent 3400 illustrated in FIGS. 8A-8D, which is wider than the vents shown in other figures, the widths may be approximately 30-50 mm, for example 40 mm.

Wide, low vent slots 3430 promote the vent flow of air through the slots to tend to be generally more laminar in nature, i.e. less turbulent, than is the case for narrower, taller slots. In some forms, the vent flow through such vent slots 3430 may have a greater amount of laminar flow compared to turbulent flow, or that laminar flow forms a greater contribution to the flow than with other, prior vent slots. Relatively more laminar (or less turbulent) flow is generally advantageous because the flow of air does not produce as much noise as more turbulent flow. Furthermore, relatively wide vents cause the vent flow to be diffused over a greater area compared to narrower slots, which reduces the intensity of flow in the path of the vent flow. FIGS. 11A and 11B illustrate vent flow 6000 for a conventional vent having multiple circular vents (specifically 24 circular vents each having a diameter of 0.85 mm) in comparison to the vent 3400 of FIGS. 4A-5C for a pressure of 10 $cmH_2O$ inside the plenum chamber 3200 and a flow rate of 321/min. It can be seen that the vent flow 6000 from the vent 3400 of FIGS. 4A-5C is spread across a wider area, which reduces how much it causes discomfort to anyone in the path of the vent flow 6000 and the amount of noise made when the vent flow 6000 impacts an object. In addition, the velocity of the flow 6000 leaving the vent is reduced.

If the height of the inlet of each slot 3430 is too large then this makes it easy for water droplets in exhaled gas to enter the slot and block the vent flow of air through the slot. This can adversely affect the performance of the slot, i.e. the vent flow rate of air through the slot and the washout of exhaled gases from the patient interface 3000. Consequently, the height of the inlet of each slot 3430 may be made sufficiently small to hinder water droplets entering the slot. In certain forms, an inlet height of 0.2-0.4 mm, for example 0.3 mm, has been found to achieve this.

A countervailing factor affecting the height of the inlet slot is the ability to manufacture slots 3430 with certain heights. The smaller the slot height, the lower the tolerances necessary to manufacture the slot adequately. To mitigate against this, in certain forms the vent body 3410 is manufactured as a single, integrally formed part.

In some forms the size, shape or arrangement of the component in which the vent 3400 is located may limit the width that the vent 3400 can be made. To accommodate this, one or more additional slots may be provided in order to achieve a similar flow rate as would be the case if the vent 3400 could be made the desired width.

5.3.4.2.1.2 Length Compared to Height

In certain forms of the technology, such as those illustrated in FIGS. 4A-10D, the vent body 3410 is configured so that the slots 3430 are long and low. That is, the length of each slot is significantly greater than the height of each slot. In the case of slots in which there are multiple measures of the length of the slot and/or multiple measures of the height of the slot, it may be the case that any one length of the slot is significantly greater than any one height of the slot. In some forms of the technology it may additionally be the case that all lengths of the slot are significantly greater than all heights of the slot. For example, in the case of the vent 3400 illustrated in FIGS. 4A-4D, all of the lengths $L_1$, $L_2$, and $L_3$ are significantly greater than both of the heights $H_I$ and $H_O$. In forms of the technology (such as those illustrated) in which the slots 3430 are also wide, this means the slots may be considered as generally long slits.

In some forms of the technology, a slot 3430 having a length that is significantly greater than the height may be considered to be a slot in which the ratio of a length to a height is at least approximately 10. Slots having a length: height ratio above this value have been found through computer modelling and through experiments to result in advantageous affects (as will next be described) in certain forms of the technology.

An advantage of a relatively long vent slot over a relatively short vent slot is that the gas flowing through the relatively long vent slot 3430 is subject to a greater amount of friction with the side walls 3438 as it passes through the vent 3400 compared to a shorter vent having shorter side walls. This means the magnitude of the velocity of the vent flow is more greatly reduced as it flows through the vent 3400 compared to a vent with shorter vent slots. In turn, this means that the magnitude of the velocity of gases expelled from the vent 3400 are lower. This is shown in the model results illustrated in FIGS. 11A and 11B, in which the maximum speed of vent flow 6000 on a vertical plane located 150 mm away from the vent 3400 of FIGS. 4A-5C is 0.22 m/s whereas for the conventional vent having multiple circular holes, this figure is 7.2 m/s. A higher speed of gases being expelled from the vent 3400 can cause at least two problems. One problem is that higher speed air travelling through a vent tends to generate more noise than slower air travelling through the same vent. Excessive noise is generally undesirable, as has already been explained. Another problem is that vented gas with a high velocity may blow onto the patient 1000 or the bed partner 1100, be felt by that person (more so than slower moving gas) and thus cause discomfort. This phenomenon is sometimes referred to as 'jetting'. High velocity air may also generate noise if it impacts against a surface such as pillows or other bedding. Of course, when one parameter of the vent (e.g. vent slot length) is varied, other parameters (e.g. total cross-sectional area) may also need to be varied in order to ensure that a required mass flow rate of gas is vented when the pressure inside the plenum chamber is at a required pressure.

However, a vent slot that is excessively long may be undesirable. In some prior vent designs with long vent slots, water vapour in the exhaled gases condenses inside the vent and condensation accumulates on the walls of the vent slot. In addition, particulates in the exhaled gases can be deposited on the walls of the vent slot with the condensation. Either or both of these effects can clog the vent slot, blocking the flow of gas through the vent slot, which affects the performance of the vent. Adverse effects may include the patient being caused to re-breathe more CO2 than would otherwise be the case, or the RPT device being required to increase the pressure to achieve the desired vent flow rate. Both these examples adversely affect patient comfort.

Consequently, it may be desirable for the length of the vent slot 3430 to not exceed a certain limit in certain forms of the technology. In some forms of the technology, slots 3430 of vent 3400 have a ratio of a length to a height that is at most approximately 50. Slots in certain forms of the technology having a length:height ratio below this value have been found through computer modelling and through experiments not to result in the adverse effects described previously. It should be appreciated that a variety of factors can cause the adverse effects described, including (but not limited to) the surface finish of the walls of the slots 3430, the relative angle of the side walls 3438 and the air pressure in the plenum chamber 3200. Therefore, in other forms of the technology, this maximum ratio at which the adverse effects are avoided may differ.

It will be appreciated that the absolute values of the length and width of the slots 3430 may vary according to a number of factors, including: the position of the vent within the respiratory therapy system; the configuration of components near the vent; the acceptable level of noise or jetting for the intended use of the respiratory therapy system; and the level of humidification to be applied to the respiratory therapy.

By way of example, the lengths of the vent 3400 may be in the range 5-10 mm and the heights of the vent 3400 may be in the range 0.2-0.8 mm. In the case of the vent 3400 illustrated in FIGS. 4A-4D, the marked lengths and heights are approximately: $L_1$=6 mm, $L_2$=6 mm, $L_3$=6 mm, $H_I$=0.2 mm and $H_O$=0.4 mm. The equivalent lengths and heights of the vents 3400 illustrated in FIGS. 6A-6D and 8A-8D are similar. In the case of the vent 3400 illustrated in FIGS. 9A-9C, the length of the slots 3430 are approximately 9 mm and the heights are similar to the other forms of the technology.

In the exemplary form of the technology shown in FIGS. 4A-4D, the length of the slot 3430 is substantially the same across the width of the slot 3430, i.e. lengths $L_1$, $L_2$ and $L_3$ are substantially equal. However, in such forms, the speed of gas moving through the vent 3400 in the middle region (i.e. middle in terms of the span of the slot in a direction along the width of the slot) may be larger than the speed of the gas moving through the end regions (i.e. regions proximate the ends of the slot, i.e. proximate the end walls 3436 at either end of the width of the slot) due to the decelerating effect of friction of the gas with the end walls 3436. This may make the jetting effect more noticeable to any persons or object located directly in front of the vent 3400. To mitigate this effect and to promote even diffusion of the vented gases, in other forms, the length of a slot varies in different parts of the slot. In particular, in some forms of the technology, a length of a middle region of the slot is greater than a length of the slot in the end regions. The greater length in the middle region increases the amount of friction that gas travelling through the middle region is subject to compared to a shorter length. The slot 3430 may be configured so that the length of the slot in the middle region is sufficiently greater than the length of the slot in the end regions that the amount of additional friction from the additional length in the middle region substantially equates to the amount of additional friction due to the end walls, and similarly for regions intermediate to the middle and end regions, so that the speed of vented gas across the width of the vent 3400 is approximately the same. In other forms, the profile of the variation of slot length across the width of the slot may vary in a different way in order to achieve any desired profile of speed of vented gas across the width of the slot.

In many prior vent designs, the length of the vent openings is often determined by the thickness of the wall of the component within which the vent is located. For example, if a vent is provided in an elbow of a patient interface, then the length of the vent openings may be equal to the thickness of the elbow walls. For components made from polycarbonate (a typical material used for elbows and plenum chambers), a typical wall thickness is no greater than approximately 1.5 mm.

In forms of the present technology, the length of the vent slots 3430 may be greater than the thickness of a wall of the component within which the vent 3400 is located. Consequently, the vent body 3410 may project inwardly, outwardly or both inwardly and outwardly from the wall(s) of the component within which the vent 3400 is located (where 'inward' in this context refers to a direction in towards the volume 3490 inside the respiratory therapy system from which gas is vented and 'outward' refers to a direction out towards ambient 3492). This enables the vent 3400 to comprise slots 3430 having the desired length without adding to the bulk of another component of the respiratory therapy system.

The vents 3400 illustrated in FIGS. 5A-5C, 7A-7C, 8A-8D,10A-10D and 13-15 demonstrate this feature. In the case of the vents 3400 illustrated in FIGS. 5A-5C and 10A-10D, for example, the vent body 3410 is mounted to a wall of an elbow 3610 of a respiratory therapy system. The vent body 3410 projects both inwardly and outwardly of the wall of the elbow 3610 to which the vent body 3410 is mounted. Also, the outlets 3434 of each vent slot 3430 are offset from an exterior surface of a wall of the elbow 3610 in a direction outward from the elbow, and the inlets 3432 of each vent slot 3430 are offset from an interior surface of a wall of the elbow 3610 in a direction inward to the elbow. In other forms, the vent body 3610 may project either inwardly only or outwardly only. In the case of the vents 3400 illustrated in FIGS. 7A-7C and 8A-8D, for example, vent body 3410 projects both inwardly and outwardly of the wall of the plenum chamber 3200 to which the vent body 3410 is mounted. However, in these forms of the technology, the vent body 3410 is configured so that both the inlets 3432 and the outlets 3434 of slots 3430 are offset from an exterior surface of a wall of the plenum chamber 3200 in a direction outward from the plenum chamber. This configuration results from the inlet 3432 being recessed from the inward facing side of vent body 3410 by a greater extent than the amount that the inner surface of the vent body 3410 projects inward to the volume 3490 inside the plenum chamber 3200. In other forms, the inlets 3432 may be level with, or offset inwardly of, the wall of the plenum chamber 3200. In the form of the technology illustrated in FIGS. 6A-6D and 7A-7C, the vent body 3410 comprises two cap plates 3422, one located at each of the top and bottom of the array of plates 3420, where the cap plates 3422 extend sufficiently far along the length of the vent body 3410 to seal a volume defined by the inner side of the vent body 3410 so that, even though the inlets 3432 are offset outwardly from an exterior surface of a wall of plenum chamber 3200, the volume immediately inward of the inlet 3432 is not fluidly connected to ambient 3492 other than through the slots 3430.

In the examples shown in FIGS. 13-15 and 19-20B, the vent 3400 projects inwardly into the plenum chamber 3200.

5.3.4.2.1.3 Outlet Area Greater than Inlet Area

It has already been described that each slot 3430 has an inlet 3432 and an outlet 3434. Since each of the inlet 3432 and the outlet 3434 have a width and a height, each of the inlet 3432 and the outlet 3434 has an area (i.e. an inlet area and an outlet area respectively), which may also be referred to as a cross-sectional area. For a rectangular-shaped inlet/outlet, the inlet/outlet area is the width multiplied by the height. Some forms of the technology may have non-rectangular-shaped inlets and outlets, for example oval, rectangular-with-rounded-corners, or some other elongate shape.

In certain forms of the technology, the vent body 3410 is configured so that, for each slot 3430, the outlet area is greater than the inlet area. More particularly, in some forms, the cross-sectional area of the slot 3430 increases gradually along the length of the slot between the inlet 3432 and the outlet 3434, for example there may be a continuous variation in cross-sectional area with increasing distance along the length of the slot 3430. As will be described further below, this may be achieved if the end walls 3436 are angled with respect to each other and/or if the side walls 3438 are angled with respect to each other. The effect of the outlet area being greater than the inlet area is that the speed of exhaled gas travelling through a vent slot 3430 reduces as the gas moves through the slot. This is because the flow rate of gas through a slot 3430 is equal to the cross-sectional area multiplied by the velocity of the gas. Therefore, for a constant flow rate of gas through the slot, as the cross-sectional area increases along the length of the slot, the speed of the gas decreases. As has been described previously, reducing the speed of vented gases is advantageous to reduce the noise produced by the vent 3400 and to reduce the level of discomfort caused by the feel of jetting gases from the vent. In addition, an outlet 3434 that has a greater area than the inlet 3432 of the same slot results in a greater angular dispersion of gases being vented from the vent 3400. Diffusing the vent flow across a wider range of angles helps to reduce the amount of vent flow that can be felt in certain directions, which again reduces the adverse impact of jetting on the patient 1000 and/or bed partner 1100. This effect is shown by the model results illustrated in FIGS. 11A and 11B.

In certain forms of the technology, the greater outlet area is provided by the outlet 3434 having a greater width than the inlet 3432. For example, in the form of vent 3400 illustrated in FIGS. 4B and 4C, the width $W_{O1}$ of the outlet 3434 is greater than the width $W_{I1}$ of the inlet 3432 and the width $W_{O2}$ of the outlet 3434 is greater than the width $W_{I2}$ of the inlet 3432. The same is true of the form of vent 3400 illustrated in FIGS. 6A-6D, although in these figures the widths are not specifically marked. The exemplary form of vent 3400 shown in FIGS. 9A-9C has an outlet 3434 having a width $W_{O1}$ that is greater than the width $W_{I1}$ of the inlet 3432. Again, it will be appreciated that the configuration of the vent body 3410, which forms the slots 3430, provides the described relative widths of the outlet and inlet.

In order to achieve the outlet area having a greater width than the inlet area, the vent body 3410 may be configured in a way that the end walls 3436 at either end of the width of each slot 3430 are oriented so that they fan out radially. That is, a projection of the first end wall 3436 inwardly towards volume 3490 would intersect with a projection of the second end wall 3436 inwardly towards volume 3490. For example, in the case of the exemplary vent 3400 shown in FIGS. 4A-4D and 6A-6D, the end walls 3436 are oriented to fan out at a relative angle of 180° (and inwards projections of the end walls 3436 into the volume 3490 would intersect at a midpoint between the inner ends of the end walls). In other forms of the technology, the end walls 3436 are oriented to fan out by relative angles of a different magnitude. The greater the magnitude of the fanning angle, the more angular dispersion of the vent flow and therefore the lesser the jetting effect where the vent flow is felt. In some forms of the technology, a fanning angle of at least 60° may be considered to provide sufficient benefits of vent flow angular dispersion in a direction parallel to the width of the slots 3430, although this angle may depend on a variety of factors and may differ in other forms of the technology. In many forms of the technology it may be desirable for the vent flow to always be projected outwardly from the respiratory therapy system, for example outwardly from an elbow or patient interface, in which case the fanning angle between the end walls is less than approximately 180° with the centre of the angular fanning range being generally directly away from the patient 1000. In the illustrated forms of vent 3400 the end walls 3436 are planar (i.e. they are straight when viewed from above, as in FIG. 4B). In other forms of the technology, the end walls 3436 may be curved or stepped.

In certain forms of the technology, the greater outlet area is provided by the outlet 3434 having a greater height than the inlet 3432. This may be in addition to, or as an alternative to, the outlet 3434 having a greater width than the inlet 3432. For example, in the form of vent 3400 illustrated in FIG. 4D, the height $H_O$ of the outlet 3434 is greater than the height $H_I$ of the inlet 3432. The same is true of the form of vent 3400 illustrated in FIGS. 6A-6D and 9A-9D, although in these figures the heights are not specifically marked. Again, it will be appreciated that the configuration of the vent body 3410, which forms the slots 3430, provides the described relative heights of the outlet and inlet.

In order to achieve the outlet area having a greater height than the inlet area, the vent body 3410 may be configured in a way that the side walls 3438 forming the top and bottom of each slot 3430 are oriented so that they fan out radially. That is, a projection of the first side wall 3438 inwardly towards volume 3490 would intersect with a projection of the second side wall 3438 inwardly towards volume 3490 or, put another way, for each slot, the side walls 3438 are oriented at a non-zero angle relative to each other such that the height of the inlet 3432 is less than the height of the outlet 3434. This relative orientation is labelled as θ in FIG. 4D and may be referred to as the draft angle of the slots 3430. In certain forms of the technology, the draft angle may be at least 1°, and may be in the range 2-7°.

The relative angle between the side walls 3438 of each vent slot 3430 contributes to the reduction in velocity of the vent flow through the slot due to the increase in cross-sectional area in the direction of vent flow, as has previously been described. Furthermore, the relative angle between the side walls 3438 has been found to result in any condensation deposited on the side walls 3438 being more easily pushed out of the slot 3430 compared to slots in which the side walls are parallel, therefore reducing the clogging effects of condensation inside the slots. Where the vent body 3410 is formed using a moulding process, for example injection moulding, the draft angle of the slots 3430 may make it easier to remove the vent body 3410 from a mould.

In the forms of the technology illustrated in FIGS. 4A-10D, the side walls 3438 are substantially planar. In other forms of the technology the side walls 3438 may be shaped differently, for example they may be curved or stepped.

In certain forms of the technology, for each of the slots 3430 of vent 3400, the inlet 3432 is concave across the width of the slot 3430. That is, a middle region of the slot 3430 projects further outwardly from the volume 3490 inside the respiratory therapy system than end regions of the slot 3430. A vent 3400 having an inlet 3432 that is concave across the width of the slot 3430 may alternatively be described as vent body 3410 having an inwardly, or positively (see FIGS. 2B and 2C, for example) curved surface across the width of the slot on the surface of the vent body 3410 in which the inlets are situated (i.e. the posterior surface of the vent body 3410 during use). The inner surface consequently comprises an arc along the width of the vent body 3410.

Additionally, or alternatively, the outlet 3434 is convex across the width of the slot 3430. That is, a middle region of the slot 3430 projects further outwardly into ambient 3492 than end regions of the slot 3430. A vent 3400 having an outlet 3434 that is convex across the width of the slot 3430 may alternatively be described as vent body 3410 having an outwardly, or negatively (see FIGS. 2E and 2F, for example) curved surface across the width of the slot on the surface of the vent body 3410 in which the outlets are situated (i.e. the anterior surface of the vent body 3410 during use). The outer surface consequently comprises an arc along the width of the vent body 3410.

Examples of vents 3400 in which the vent body 3410 is configured so that the inlets 3432 of the slots 3430 are concave and the outlets 3434 of the slots 3430 are convex are shown in FIGS. 4A-4D, 6A-6D and 8A-8D. In the example of FIGS. 4A-4D, the vent body 3410 is generally C-shaped when viewed in a direction parallel to the height of a slot 3430. In the example of FIGS. 6A-6D, the vent body 3410 is generally D-shaped when viewed in a direction parallel to the height of a slot 3430. An example of a vent 3400 in which the vent body 3410 is configured so that the outlets 3434 of the slots 3430 are concave but the inlets 3432 of the slots are straight (i.e. not concave) is shown in FIGS. 9A-9C.

Vents having a concave inlet and/or a convex outlet across the width of the slot may be beneficial in promoting greater angular dispersion of vented gases in a direction parallel to the width of the slot (i.e. in the direction in which the concavity/convexity is present). It will be appreciated that, for each slot, the greater the arc length of the surface defining the outlet compared to the surface defining the inlet, the greater the amount of angular dispersion.

In some forms of the technology, for each slot 3430, the degree of concavity of the inlet 3432 (or the amount of positive curvature of the vent body 3410 on the inlet side) is less than the degree of convexity of the outlet 3434 (or the amount of negative curvature of the vent body 3410 on the outlet side). Such a configuration may result in a width of the outlet 3434 being greater than a width of the inlet 3432.

5.3.4.2.2 Parallel Arrangement of Slots

In certain forms of the technology, such as those illustrated in FIGS. 4A-10D, the slots 3430 of vent 3400 are arranged so that the slots 3430 are generally parallel to each other. More particularly, the direction in which the widths of each slot 3430 extends is parallel to the direction in which the widths of the other slots of the plurality of slots extend so that the widths of the plurality of slots extend in mutually parallel directions. Where a width is not considered to extend along a straight line, for example widths $W_{I1}$ and $W_{O1}$ of the slot 3430 shown in FIG. 4B, a width of one slot may be considered parallel to a width of another slot if the widths lie on planes that are mutually parallel. Alternatively, the widths of this form of vent that do extend in a straight line, i.e. widths $W_{I2}$ and $W_{O2}$, may be parallel to the equivalent widths of one of the other slots 3430 of the plurality of slots.

In addition, one or more of the lengths of each of the plurality of slots 3430 may extend in mutually parallel directions. For example, the slots 3430 of the vent 3400 shown in FIGS. 4A-4D has a length $L_2$ in a middle region of the slot 3430. This length extends in a direction that is parallel to the direction in which the equivalent length of other slots in the vent 3400 of this form of the technology extends.

Earlier it was described that each slot 3430 is slit-like and consequently has a volume that is generally flat, or planar, in shape (i.e. a volume that is relatively long in two mutually perpendicular dimensions—width and length—but short in a third mutually perpendicular dimension—height). The parallel arrangement of the slots that has been described may be considered as the slots 3430 being arranged such that their generally planar volumes are arranged in parallel.

In certain forms of the technology, such as those shown in FIGS. 4A-10D, the plurality of slots 3430 are arranged in this generally mutually parallel arrangement such that the slots 3430 are arranged in a spaced array. That is, the slots are separated from each other in a direction parallel to a direction of the heights of the slots 3430. The amount of separation may be the same between each pair of adjacent slots, or the amount of separation may differ between pairs of adjacent slots. As has already been explained, it will be appreciated that, in some forms of the technology, it is the positioning and arrangement of the plates 3420, between which the slots 3430 are formed, that achieves this arrangement of the slots 3430.

In some forms of the technology the slots 3430 may be curved, rather than substantially flat, when viewed along the length dimension. For example, the annular flow paths 3462 shown in FIGS. 12-17 may be considered to be curved slots which are arranged to form concentric circles. The slots of such vents have a constant spacing between them (e.g. in the radial direction) and so can be considered to be arranged in parallel. In such examples the "width" of each slot may be taken to be the distance in the circumferential direction and the "height" the distance in the radial direction. In other examples, the slots 3430 may be configured into other curved forms, e.g. parallel arcs. Some such forms of the technology may provide some or all of the advantages of vents having parallel, substantially straight slots, as described herein with reference to FIGS. 4A-10D.

In certain forms of the technology, such as shown in FIGS. 4A-4D, the slots 3430 are equally sized and arranged such that their inlets, outlets and/or their end walls are aligned. In other forms, the slots 3430 are equally sized and arranged such that their inlets, outlets and/or end walls are offset from each other in a direction parallel to a direction in the plane of the slots 3430, for example in FIGS. 8A-8D where the slots 3430 are offset in a direction parallel to the direction in which the length of each slot extends in a middle region of the slot. The amount of offset may be the same between each pair of adjacent slots, or the amount of offset may differ between pairs of adjacent slots. In still other forms, one or more of the plurality of slots may differ in size from any one or more other of the plurality of slots.

The generally parallel arrangement of the slots 3430 enables the vent 3400 to be compact in form with quiet operation. When compared to a vent in which there is only a single opening or slot, an arrangement of multiple parallel slots means that a reduced cross-sectional area for each individual slot is required to achieve the same overall vent area. The overall vent area is generally dictated by the amount of gas needing to be vented at a given pressure within the respiratory therapy system, for example to vent 32 L/min when the pressure is 10 $cmH_2O$ it is generally considered that a vent area of approximately 10-15 $mm^2$ is necessary, for example approximately 13 $mm^2$. This vent area can be achieved through a single vent opening or multiple vent openings. The forms of the technology shown in the figures and described herein achieve approximately this vent area through multiple slot-like openings, for example three to eight openings, for example four openings. As has already been explained, such wide, low vent slots 3430 promote the vent flow of air through the slots to tend to be generally more laminar, or less turbulent, in nature than conventional vent slots. This reduces the noise produced by the vent when compared to a vent having a single opening, which may need to be higher and narrower to fit into the same region of a component of the respiratory therapy system while providing the same vent area.

The generally parallel arrangement of the slots 3430 may also enable the vent 3400 to be provided in modular form, as explained further below.

In the forms of the technology illustrated in FIGS. 5A-5C, 7A-7C and 8A-8D, the slots 3430 are oriented so that, when in use, they extend width-wise in a lateral direction relative to the patient's body. For example, the plates 3420 (between which are formed slots 3430) may lie generally parallel to the patient's transverse plane in use. In the form of the technology illustrated in FIGS. 9A-9C, the slots 3430 are oriented so that, when in use, they extend width-wise in the sagittal plane of the patient's body, or in a plane parallel to the sagittal plane. For example, the plates 3420 (between which are formed slots 3430) may lie generally in or parallel to the patient's sagittal plane in use. In other forms of the technology the slots 3430 may be oriented in a different direction.

The plane of the slots 3430 may be oriented at right angles to the walls of the vent body 3410, such as is the case in the form of vents 3400 shown in FIGS. 4A-4D and 6A-6D. Alternatively, the plane of the slots 3430 may be oriented at a non-perpendicular angle to the walls of the vent body 3410, as is the case in the form of vent 3400 shown in FIGS. 8A-8D, where the slots 3430 are angled slightly downwards compared to the perpendicular direction from the outer wall of vent body 3410. For any particular vent 3400, the angle of the slots 3430 may be selected to direct the vent flow of exhaled gases generally away from areas which might cause discomfort.

5.3.4.2.3 Radius at Outlet/Inlet

In certain forms of the technology, the vent body 3410 may comprise curved edges 3442 at the inlet 3432 of each slot 3430 and/or curved edges 3444 at the outlet 3434 of each slot 3430. That is, when the vent body 3410 is viewed along a cross-section taken along a length of a slot 3430 (for example, as shown in FIGS. 4D and 6D), the corners of the vent body 3410 at the inlet 3432 and/or the outlet 3434 are curved with a radius. These curved corners help to avoid turbulence being generated in the vent flow of gas entering and/or exiting the slots 3430. It has been found that variation to the radius of the curved corners can have an impact on the amount of turbulence produced and consequently the noise generated by the vent 3400. In certain forms of the technology a radius in the range of approximately 0.1-0.3 mm has been found to be beneficial. For example, in the forms of the technology shown in FIGS. 4A-4D and 6A-6D, the radius of the curved edges 3442 at the inlet 3432 and the curved edges 3444 at the outlet 3434 of the slot 3430 is approximately 0.2 mm. In the form of the technology shown in FIGS. 9A-9C, the radius of the curved edges 3442 at the inlet 3432 is approximately 0.2 mm and the radius of the curved edges 3444 at the outlet 3434 of the slot 3430 is approximately 0.1 mm. In some forms, the larger the radius of the curved edges 3442 and 3444, the less noise is produced by the vent 3400.

5.3.4.2.4 Flow-Blocking Members

In some forms of the technology, the slots 3430 may be segmented in some fashion along their width in order to limit or prevent flow in a length-wise direction along part of the width of the slots 3430. For example, the vent 3400 may comprise one or more flow-blocking members positioned in one or more of the slots 3430 in order to block the venting of gases through a part of the slot. The flow-blocking members may be comprised as part of the vent body 3410 (for example, integrally formed as part of the vent body 3410) or may be provided to the vent body, for example attached to one or more of the side walls 3438 of the slot in which the member is positioned.

The flow-blocking members may take the form of solid bodies having a height equal to the height of the slot 3430 in which each is positioned and a length that is equal to or less than the slot 3430. The width of the flow-blocking member corresponds to the extent to which vent flow is prevented across a part of the width of the slot.

The width of the flow-blocking members, the number of flow-blocking members and the position of the flow-blocking members in each slot 3430 is dependent on how the vent flow is desired to be impeded along in slot. In one exemplary form, it is determined that vent flow directly forwards from the patient interface 3000 is undesirable, for example because in this direction the vent flow is most likely to impact a bed partner 1100. Therefore flow-blocking members are positioned in the middle region of each of the vent slots 3430 and the flow-blocking members have a width corresponding to the direction in which vent flow is desired to be blocked.

It will be appreciated that the use of flow-blocking members effectively reduces the cross-sectional area of the slots 3430. Consequently, in forms of the technology in which flow-blocking members are provided, in may be necessary for the design of the vent body 3410 to compensate for their presence in some way in order to maintain the desired vent flow rate and/or velocity, for example by widening one or more slots, heightening one or more slots and/or increasing the number of slots compared to forms of the technology in which flow-blocking members are not used.

5.3.4.3 Location of Vent

The vent 3400 may be located in different parts of the respiratory therapy system according to different forms of the technology. The different possible locations for vent 3400 include different locations on the patient interface 3000, as illustrated in the figures and as will now be described.

5.3.4.3.1 Elbow

In the form of the technology shown in FIGS. 5A-5C there is illustrated a tube portion that is comprised as part of a patient interface 3000. In the form shown the tube portion comprises a bend and is consequently in the form of an elbow 3610. In other forms the tube portion may be straight, or substantially straight.

The elbow 3610 comprises a first end 3612 that is configured to directly or indirectly fluidly connect to the plenum chamber inlet port in plenum chamber 3200 and a second end 3614 configured to directly or indirectly fluidly connect to air circuit 4170. In use, the elbow 3610 therefore channels the flow of air received from air circuit 4170 to the plenum chamber 3200.

In the form of the technology illustrated in these figures, the vent 3400 is provided to the elbow 3610. More particularly, the vent 3400 is provided to a surface of the elbow 3610 that, in use, faces generally away from the patient 1000, i.e. an anterior surface of the elbow 3610. This location helps to ensure that the vent flow of gas is away from the patient.

In the illustrated form, the vent 3400 is located on a relatively straight section of the elbow 3610 proximate to the end of the elbow that, in use, connects to the air circuit 4170.

In the form of vent 3400 illustrated in FIGS. 9A-9C, the vent 3400 is located proximate the apex of the bend in the tube portion. In this form the vent body 3610 is oriented such that the slots 3430 direct the vent flow of gas in an anterior-superior direction in use. This orientation may be beneficial in avoiding the vent flow of gas jetting into the patient's bed partner 1100.

The vent body 3410 may be integrally formed as part of the elbow 3610 or may be a separate component that is mounted to the elbow 3610.

Locating the vent 3400 in the elbow 3610, particularly near the apex of the bend in the elbow, may position the vent 3400 substantially directly in the path of exhaled gases from the patient's airways. This results in a greater proportion of the gas exhaled by the patient being vented to ambient compared to a patient interface in which the vent is located away from the direct path of exhaled gases. This may reduce the amount of CO2 retained in the plenum chamber 3200 compared to such other patient interfaces.

5.3.4.3.2 Plenum Chamber

In the form of the technology illustrated in FIGS. 7A-7C, 8A-8D, 13-15 and 19-20B, the vent 3400 is provided to the plenum chamber 3200 of the patient interface 3000. More particularly, the vent 3400 is located in a wall of the plenum chamber, for example an anterior-facing wall. The vent body 3410 may be integrally formed as part of the plenum chamber 3200 or may be a separate component that is mounted to the plenum chamber 3200.

The forms of patient interface 3000 illustrated in FIGS. 7A-7C and 8A-8D both comprise conduit headgear (although the headgear tubes are not illustrated in FIGS. 7A-7C). This type of mask may be particularly suited to a vent 3400 of the type described herein being provided to the plenum chamber 3200 because, without the air circuit being connected to the front of the patient interface, there may be sufficient space for the plenum chamber 3200 to accommodate a vent comprising an array of wide vent slots. However, forms of the technology are not limited to vents 3400 being provided to the plenum chamber 3200 only for patient interfaces comprising conduit headgear. Other forms of the technology relate to vents of the type described herein applied to other types of patient interface, including all of the other types described herein.

Locating the vent in the plenum chamber 3200, particularly in the case of a patient interface 3000 comprising conduit headgear, may also enable the vent 3400 to be positioned substantially directly in the path of exhaled gases from the patient's airways. The advantages of this have been previously described.

5.3.4.3.3 Conduit Headgear

In other forms of the technology, a vent 3400 according to a form of the technology is provided to a part of conduit headgear that forms part of the patient interface 3000. That is, the vent 3400 is provided to a headgear tube 3350 that delivers pressurised air received from a conduit forming part of the air circuit 4170 to the plenum chamber 3200. In some forms, the patient interface 3000 comprises two headgear tubes 3350 and a vent 3400 is provided to each headgear tube.

5.3.4.4 Vent Module

In certain forms of the technology, the vent 3400 is provided as a vent module. A vent module is a component or an assembly that comprises a vent 3400 that is formed separately from the other components of the patient interface 3000 and added to these other components during assembly of the patient interface 3000. The vent module may, in some forms, be able to be separated from the rest of the patient interface 3000 after assembly, for example for cleaning, replacement and/or repair. The removability of the vent 3400 for cleaning makes it easy for a patient to clean the vent, for example by holding the vent under a tap and optionally using a brush.

The vent module may be configured in a way that means it is able to be selectively used in a number of different types of patient interface 3000. The vent module may also be configured so that it can be selectively positioned in a number of different locations on different types of patient interface 3000. Alternatively, the vent module may be configured in a way that means it is able to be selectively positioned in a number of different locations on a single type of patient interface 3000. In order to achieve this, the patient interface(s) 3000 are also configured in a manner that allows them to receive a vent module at one or more different locations.

Furthermore, a plurality of patient interfaces 3000, which may include a plurality of different types of patient interface, may be configured so that a particular configuration of vent module is able to be interchangeably assembled with each of the types of patient interface.

In the forms of the technology illustrated in FIGS. 5B and 10C, the elbow 3610 is formed with an opening 3620 in one of its walls that has a size and shape that makes the opening suitable to accommodate a vent module 3450. In the form of the technology illustrated in FIG. 7B, the plenum chamber 3200 comprises an opening 3620 in an anterior wall that has a size and shape that makes the opening suitable to accommodate a vent module 3450. In FIG. 16A a similar opening is shown.

During assembly, or re-assembly, of the patient interface 3000, the vent module 3450 provided to the opening 3620 in the elbow 3610 or plenum chamber 3200, for example by being inserted into the opening or mounted in front of the opening. Subsequently, the vent module 3450 may be removed and then re-positioned (e.g. after cleaning) or replaced with another, similar vent module 3450, or another vent module having a different configuration but also able to assemble by being provided to the opening 3620.

Different forms of the technology may use different mechanisms to assemble vent module 3450 with the patient interface 3000. In one form, the vent module 3450 friction fits into the opening 3620. In another form, a snap-fit mechanism is used to connect the vent module 3450 to the elbow 3610 or plenum chamber 3200 in a way that positioned the vent module 3450 over the opening 3620. Other mechanisms may be used in other forms of the technology.

5.3.4.5 Variable Flow Vents

In some forms of the technology the vent 3400 is configured to have a variable impedance to flow. In examples, the vent 3400 may have a first configuration in which the pressure inside the volume 3490 (e.g. inside the plenum chamber 3200) is maintained at a therapy pressure, and a second configuration in which the flow through the vent 3400 is increased such that the pressure inside the volume 3490 is lower than therapy pressure. In examples, the vent 3400 may be maintained in the second configuration while the patient falls asleep, and may be moved to the first configuration after the patient has fallen asleep to deliver therapy pressure.

FIGS. 12-17 show a vent 3400 according to one form of the technology. The valve 3400 is shown mounted to other components in FIGS. 13-16.

The vent 3400 comprises a body 3410 which defines a housing 3412. The housing 3412 has an opening 3446 at one end. In embodiments, the housing 3412 has only one aperture or opening 3446.

The body 3410 defines at least one flow path 3460 from an upstream side 3402 (also called an inlet) of the vent 3400 to a downstream side 3404 (also called an outlet) of the vent 3400. In the example shown in FIGS. 12-17, the at least one flow path 3460 is provided in the form of a plurality of annular flow paths 3462. In examples the flow paths 3460 are concentric.

In some forms of the technology the vent 3400 further comprises a cover 3470. In the example shown in FIGS. 12-17, the cover 3470 is substantially mushroom or umbrella shaped, having a base portion 3472 and a broader head portion 3474. However, in other examples only a portion of the head 3474 extends laterally beyond the base portion 3472. The base portion 3472 is engaged with the body 3410 so as to seal the opening 3446 in the housing 3412. The head portion 3474 is configured to move between a first configuration (shown in FIG. 17A), in which the head portion 3474 at least partially occludes at least one of the flow paths 3460, and a second configuration (shown in FIG. 17B) in which the degree of occlusion is reduced (e.g. such that there is substantially no occlusion).

In the example shown in FIGS. 12-17, the cover 3470 is made from a flexible material (for example silicone), such that the head portion 3474 can move between the first and second configurations while the base portion 3472 remains engaged with the housing 3412. In examples the end 3476 of the base portion 3472 distal the head portion 3474 does not move relative to the housing 3412.

In examples, the head portion 3474 is moved between its first and second configurations by an actuator 3480. The actuator 3480 is provided within the housing 3412. In the example shown in FIGS. 12 to 17, the actuator 3480 comprises a stepper motor 3482 which changes the position of the head portion 3474 relative to the vent body 3410 by means of a leadscrew mechanism 3484. However, alternative actuation methods are possible, for example as described further below.

As can be seen in FIG. 17A, when in the first configuration, a lower or inner surface 3478 of the head portion 3474 covers an innermost one 3464 of the annular flow paths 3462, thereby substantially preventing flow through that flow path 3460. When in the second configuration, shown in FIG. 17B, the lower or inner surface 3478 of the head portion 3474 is moved away from the inlet 3486 to the innermost annular flow path 3464, decreasing the degree of occlusion of the flow path 3464 and thereby allowing at least some flow through that flow path. In the example shown in FIGS. 12-17, at least one flow path 3460 (e.g. the outermost annular flow path 3466) is always free of occlusion by the cover 3470. In alternative examples, additional flow paths 3460 may be provided which are not occluded by the cover 3470 when in the first position and/or additional flow paths 3460 may be provided which are at least partially occluded by the cover 3470 when in the first position.

In examples of the technology, the cross-sectional area of each flow path 3460 increases from the inlet 3486 of the flow path 3460 to the outlet 3500. As can be seen in FIGS. 15 to 17, and in particular FIG. 16B, at least pairs of the side walls of the flow paths 3460 may be non-parallel (e.g. divergent). In the example shown, the cross-sectional area of each flow path 3460 increases linearly and continuously from the inlet 3486 to the outlet 3500. In examples, the height of the inlet 3486 to each flow path 3460 is small compared to the length of each flow path. In examples the ratio of the height to the length is 1:30 or less, e.g. around 1:40. This geometry may assist in reducing the noise generated by flow through the vent 3400 by reducing or eliminating turbulence.

In examples of the technology, the vent 3400 is configured to allow formation by injection moulding without the presence of any undercut. In examples, the flow paths 3460 are formed such that the interior walls 3468 of each flow path 3460 are substantially parallel to, or divergent from (when moving from the upstream end to the downstream end), any axis P which is parallel to the centreline of the vent 3400 and which falls within the inlet 3486 of the respective flow path 3460. As is described in more detail above with reference to draft angle, this may simplify the moulding process.

Referring next to FIGS. 18A and 18B, a vent 3400 is shown which has a body 3410 which is the same shape and configuration as the body 3410 of the vent 3400 shown in FIGS. 12-17. The cover 3470 is also a similar shape. However, in this example the cover 3470 is actuated by an electromagnet 3510 which acts on a ferromagnetic element (e.g. a steel disc) 3520, or a magnetic element, which is connected to the head portion 3474 of the cover 3470. By varying the magnetic field created by the electromagnet 3510, the head portion 3474 can be moved between its first and second configurations. In another embodiment a solenoid type linear actuator may be used to move the head portion 3474 between the first and second configurations. In examples the solenoid may comprise a spring which biases the solenoid to a configuration corresponding to the second position/configuration of the cover 3470.

In examples, the head portion 3474 adopts the second configuration in the absence of any external force (e.g. from the actuator 3480) and is deformed to the first configuration by the action of the actuator. In this way the head portion 3474 is biased to move to the second configuration (in which occlusion of the flow paths is reduced) if power to the electromagnet 3510 fails. Additionally, or alternatively, the head portion 3474 may be connected to an "over centre" mechanism which biases the head portion 3474 to remain in a current position or configuration until the actuator 3480 overcomes the biasing force. In this way the actuator 3480 may only need to be powered when a change of position/configuration of the cover 3470 is required, rather than continuously powering the actuator 3480, as may be otherwise necessary (e.g. for actuators based on electromagnets).

If current is supplied to the electromagnet 3510 in an uncontrolled or "step change" manner, the head portion 3474 may move from the second configuration to the first configuration very rapidly. This may cause a noise and/or a vibration through the patient interface 3000 which may be sufficient to rouse the patient. Accordingly, in examples, the increase in current to the electromagnet 3510 may be controlled such that the change in configuration of the head portion 3474 from the second configuration to the first configuration is less abrupt and the noise and/or vibration is reduced or substantially eliminated.

Examples which use a leadscrew type actuator 3480 may also be controlled in a similar way, but in some examples the rotational speed of the stepper motor 3482 (combined with the pitch of the screw) may be selected such that changes from the second configuration to the first configuration do not cause unacceptable levels of noise and/or vibration, even with the stepper motor 3482 acting at full speed. In such examples it may not be necessary to provide additional control of the speed of the stepper motor 3482 to reduce noise and vibration.

As can be seen in FIGS. 13-17, in examples the head portion 3474 moves in a posterior direction when moving from the first position to the second position. In examples the cover 3470 is provided on the patient facing side 3406 of the vent 3400 and may be located on a patient facing side of the frame or shell of the patient interface 3000 (e.g. within the plenum chamber 3200). In this way, movement of the head portion 3474 is less likely to be obstructed when the patient interface is in use, for example by the patient's pillow. Leadscrew type actuators may be particularly suitable for examples of the invention with the cover 3470 provided on the patient facing side 3406 of the vent 3400, since the movement of the cover 3470 may be controlled or restrained over the entire distance from the second configuration or position to the second configuration or position. By contrast, covers which are moved by an electromagnet or solenoid may accelerate more than intended under the influence of air pressure differential.

In some examples, the body 3410 of the vent 3400 does not protrude from the anterior surface 3302 of the patient interface.

Examples of the technology such as those shown in FIGS. 12-18 may allow the vent 3400 (and patient interface 3000) to be washed without exposing the actuator 3480 to water, since the actuator 3480 is contained within the housing 3412 and the housing 3412 is sealed by the cover 3470. In some examples a battery for the actuator may also be provided within the housing 3412, along with wireless (e.g. inductive) battery recharging means. In examples, control signals may be sent wirelessly to the actuator 3480, for example by Bluetooth or similar. A controller may be provided within the housing 3412 to receive the wireless signal and control the actuator 3480. In examples, the controller may be configured to move the cover 3470 to the second position/configuration if the battery drops below a threshold minimum charge.

Referring next to FIGS. 19 and 20, another example of the technology is shown. In this example the vent body 3410 is substantially as described above with reference to FIGS. 12-18. However, the cover 3470 comprises a central portion 3530 connected to a mounting portion 3540 by a plurality of support portions 3550. The support portions 3550 may be radially spaced around the central portion 3530. In examples, the support portions 3550 are flexible.

In the example shown the mounting portion 3540 is substantially annular in shape and the central portion 3530 is provided within the circumference of the annular mounting portion 3540. In the example shown the mounting portion 3540 is configured to engage an outer wall of the housing 3412.

The central portion 3530 is moveable between a first position, in which the cover 3470 at least partially occludes at least one of the flow paths 3460, and a second position in which the degree of occlusion is reduced. In the example show, the central portion 3530 is biased toward the second position by the resilience of the support portions 3550.

In the example shown in FIGS. 19 and 20 the central portion 3530 is actuated by a stepper motor 3482 and leadscrew arrangement 3484. However, in alternative examples the actuator 3480 may comprise an electromagnet 3510 and ferromagnet or magnet arrangement such as that shown in FIG. 18. In another embodiment a solenoid type linear actuator may be used to move the central portion 3530 between the first and second positions. In examples which use electromagnetic actuation of the central portion 3530, the movement of the central portion 3530 may be controlled to reduce noise and/or vibration, as described above with reference to FIGS. 12 to 18.

Referring next to FIGS. 21 to 23, a patient interface 3000 with a vent 3400 according to another form of the technology as shown. In this embodiment the patient interface 3000 is configured as a nasal cradle mask. The mask comprises a frame 3010 which forms at least part of the plenum chamber 3200. A plurality of vent apertures 3560 are provided through the frame 3010.

A cover 3470 is provided which is movable from a first position in which the cover 3470 partially occludes at least one, or each, vent aperture 3570 and a second position in which the degree of occlusion is reduced. The vent cover 3470 is itself provided with a plurality of apertures 3570 which allow some flow through the cover 3470 when in the first position. The plurality of apertures 3570 provide a required impedance to flow and also diffuse the flow through the vent apertures 3560 when the cover 3470 is in the first position.

When in the first position, the cover 3470 may engage the anterior surface 3020 of the frame 3010 surrounding the vent apertures 3560, such that substantially all of the flow through the vent apertures 3560 flows through the apertures 3570 in the cover, e.g. with the cover 3470 in the first position, flow around the outer perimeter of the cover 3470 may be minimised and/or eliminated.

In the example shown in FIGS. 21-23, the vent cover 3470 comprises a base portion 3472 which comprises a ferromagnetic or magnetic element. An electromagnet 3510 is provided to the frame 3010. The electromagnet 3510 is configured to define an opening or channel 3580 which can receive the base portion 3472 of the cover 3470. By varying the magnetic field created by the electromagnet 3510 the cover 3470 can be moved between its first and second positions. In another embodiment a solenoid type linear actuator may be used to move the cover 3470 between the first and second positions.

In examples of the invention, power for the actuator 3480 may be provided by wires which are provided to an air circuit 4170 which is connected to the patient interface 3000 in use.

In examples, the cover 3470 may be moved to the second position or configuration while the patient is going to sleep, in order to ensure that the pressure in the patient interface 3000 is low, while providing a sufficient flow rate to ensure adequate washout (e.g. to ambient) through the vent(s). The cover 3470 may be moved to the first position or configuration when the RPT (or other sensing device) determines that the patient is asleep, or when a predetermined time has passed. When in the first position the pressure in the patient interface 3000 may increase to the therapy pressure.

In some forms of the technology, examples similar to those shown in any of FIGS. 4A-10D may be modified for use as a variable flow vent by provision of a suitable actuator and cover, for example a suitable one of those described above with reference to FIGS. 12-23. In such examples the overall size of the vent or vent module may need to be increased, e.g. to allow for the presence of the actuator.

5.3.5 Heat and Moisture Exchanger (HME)

Heat and moisture exchangers (HMEs or HMXs) may comprise materials that have water retaining properties. Respiratory pressure therapy can result in drying of the airways causing breathing discomfort in patients. To prevent this, a humidifier 5000 may be used in conjunction with a RPT device 4000 to deliver humidified air to the patient 1000. This added humidifier may increase the size and power requirements of RPT devices.

It is known that a patient generates a level of humidified air upon exhalation, which comes from the mucosa of the airways. HMEs are used to recycle this exhaled moisture by capturing humidity from humidified air upon exhalation then redelivering this to the patient. One challenge in the use of HMEs is their efficacy (i.e., being able to capture enough heat and moisture) and their impact on therapy (i.e., the HME may be placed in the flow circuit and therefore cause flow impedance).

To improve efficacy, it is desirable to reduce any losses of heat and moisture that is captured by the HME. To achieve this, the HME may be placed closer to the patient 1000 than the vent 3400, e.g. proximal to the patient's airways (i.e., the source of humidity). This configuration may ensure that expired humidified gases flow through the HME such that moisture is captured by the HME prior to exiting through the vent.

In certain forms of the technology, the patient interface 3000 comprises an HME 3900. HME 3900 is positioned such that exhaled gases from the patient 1000 pass through the HME 3900. HME 3900 may be positioned to cover the inlet to vent 3400. For example, in the form of the technology illustrated in FIGS. 10A-10D, the patient interface 3000 comprises an HME 3900 that is located inside elbow 3610 and is mounted to the surface of vent body 3410 facing inwardly towards volume 3490. HME 3900 has a size and shape such that it covers the area of inlets 3432, meaning that any gas venting out through vent 3400 must pass through the HME 3900. This allows the HME 3900 to recover as much humidification from the exhaled gases as possible.

HME 3900 may be mounted to vent body 3410 in any suitable manner. In the form shown in FIG. 9A, the vent body 3410 comprises one or more protrusions 3910 on a side of the vent body that faces the HME 3900, and the HME 3900 comprises a corresponding number of recesses 3920 on a side of the HME that faces the vent body 3410. The protrusions 3910 are configured to friction fit into the recesses 3920 in order to securely hold the HME 3900 against the vent body 3410. In other forms of the technology, other connection mechanisms may be used, including snap-fits, adhesives, integral moulding, and the like.

5.3.6 Decoupling Structure(s)

In one form the patient interface 3000 includes at least one decoupling structure, for example, a swivel or a ball and socket.

5.3.7 Connection Port

Connection port 3600 allows for connection to the air circuit 4170.

In certain forms of the technology, the connection port 3600 is comprised as part of a tube portion that is itself comprised as part of patient interface 3000 and is configured to channel the flow of air from the air circuit 4170 to the plenum chamber 3200. The tube portion may comprise a bend and take the form of an elbow 3610. In such forms, the end of the tube portion distal from the plenum chamber 3200 comprises the connection port 3600.

In other forms, the connection port 3600 may be comprised as part of another part of the patient interface 3000, for example as part of a positioning and stabilising structure 3300 taking the form of conduit headgear.

5.3.8 Forehead Support

In one form, the patient interface 3000 includes a forehead support 3700.

5.3.9 Anti-Asphyxia Valve

In one form, the patient interface 3000 includes an anti-asphyxia valve.

5.3.10 Ports

In one form of the present technology, a patient interface 3000 includes one or more ports that allow access to the volume within the plenum chamber 3200. In one form this allows a clinician to supply supplementary oxygen. In one form, this allows for the direct measurement of a property of gases within the plenum chamber 3200, such as the pressure.

5.4 RPT Device

An RPT device 4000 in accordance with one aspect of the present technology comprises mechanical, pneumatic, and/or electrical components and is configured to execute one or more algorithms. The RPT device 4000 may be configured to generate a flow of air for delivery to a patient's airways, such as to treat one or more of the respiratory conditions described elsewhere in the present document.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.6 Humidifier

Figure 3A:
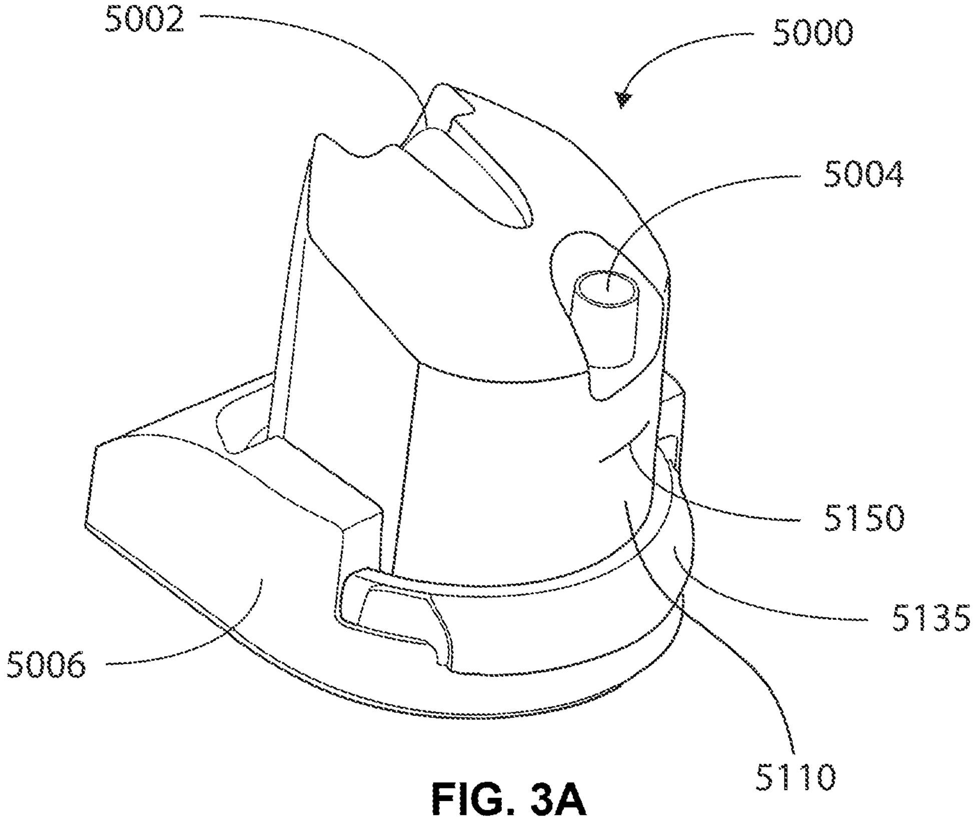
FIG. 3A shows an isometric view of a humidifier in accordance with one form of the present technology.

In one form of the present technology there is provided a humidifier 5000 (e.g. as shown in FIG. 3A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

Figure 3B:
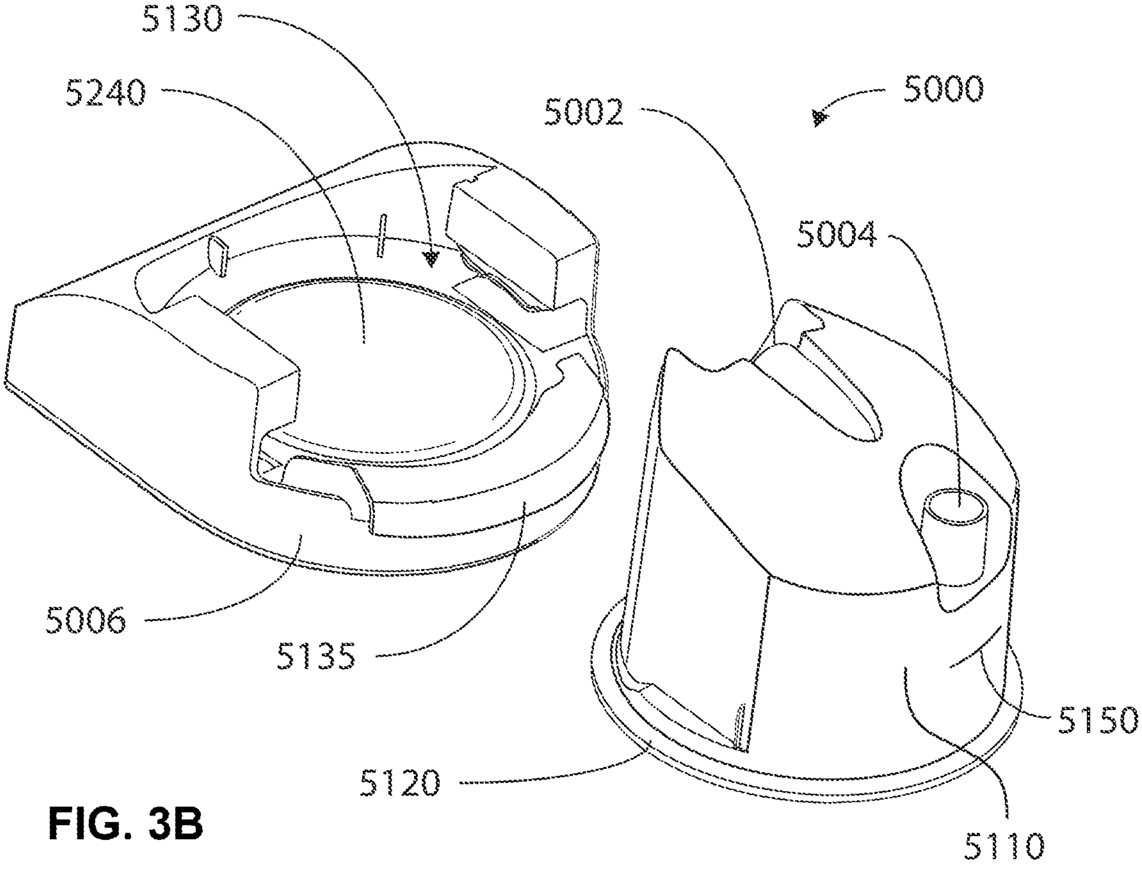
FIG. 3B shows an isometric view of a humidifier in accordance with one form of the present technology, showing a humidifier reservoir 5110 removed from the humidifier reservoir dock 5130.

The humidifier 5000 may comprise a humidifier reservoir 5110, a humidifier inlet 5002 to receive a flow of air, and a humidifier outlet 5004 to deliver a humidified flow of air. In some forms, as shown in FIG. 3A and FIG. 3B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240. The humidifier base 5006 may be provided with a locking lever 5135. The reservoir 5110 may be provided with a conductive portion 5120 and a water level indicator 5150.

5.7 Glossary

For the purposes of the present technology disclosure, in certain forms of the present technology, one or more of the following definitions may apply. In other forms of the present technology, alternative definitions may apply.

5.7.1 General

Air: In certain forms of the present technology, air may be taken to mean atmospheric air, and in other forms of the present technology air may be taken to mean some other combination of breathable gases, e.g. oxygen enriched air.

Ambient: In certain forms of the present technology, the term ambient will be taken to mean (i) external of the treatment system or patient, and (ii) immediately surrounding the treatment system or patient.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Pressure: Force per unit area. Pressure may be expressed in a range of units, including $cmH_2O$, g-f/$cm^2$ and hectopascal. 1 $cmH_2O$ is equal to 1 g-f/$cm^2$ and is approximately 0.98 hectopascal (1 hectopascal=100 Pa=100 N/$m^2$=1 millibar 0.001 atm). In this specification, unless otherwise stated, pressure is given in units of $cmH_2O$.

Respiratory Pressure Therapy: The application of a supply of air to an entrance to the airways at a treatment pressure that is typically positive with respect to atmosphere.

Ventilator: A mechanical device that provides pressure support to a patient to perform some or all of the work of breathing.

5.7.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.7.2 Patient Interface

Anti-asphyxia valve (AAV): The component or sub-assembly of a mask system that, by opening to atmosphere in a failsafe manner, reduces the risk of excessive CO2 rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.8 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.9 Reference Signs List

1000 Patient
1100 Bed partner
3000 Patient interface
3010 Frame
3020 Anterior surface of frame
3100 Seal forming structure
3150 Cushion module
3200 Plenum chamber
3210 Chord
3220 Superior point
3230 Inferior point
3300 Stabilising structure
3302 Anterior surface of vent
3310 Strap
3320 Tab
3350 Headgear tube
3362 Concertina structure
3363 Non-extendible section
3400 Vent
3402 Upstream side of vent
3404 Downstream side of vent
3406 Patient facing side
3410 Vent body
3412 Housing
3420 Plate
3422 Cap plates
3430 Slot
3432 Inlet
3434 Outlet
3436 End wall
3438 Side wall
3442 Curved edge
3444 Curved edge
3446 Opening
3450 Vent module
3460 Flow path
3462 Annular flow path
3464 Innermost annular flow path
3466 Outermost flow path
3468 Inner wall of flow path
3470 Cover

3472 Base portion
3474 Head portion
3476 Distal end
3478 Lower surface
3480 Actuator
3482 Stepper motor
3484 Leadscrew
3486 Inlet
3490 Volume
3492 Ambient
3500 Outlet
3510 Electromagnet
3520 Ferromagnetic element
3530 Central portion
3540 Mounting portion
3550 Support portion
3560 Vent aperture
3570 Vent cover aperture
3580 Channel
3600 Connection port
3610 Elbow
3612 First end
3614 Second end
3620 Opening
3700 Forehead support Heat and moisture exchanger
3900 (HME)
3910 Protrusion
3920 Recess
4000 RPT device
5000 Humidifier
5002 Humidifier inlet
5004 Humidifier outlet
5006 Humidifier base
5110 Humidifier reservoir
5120 Conductive portion
5130 Reservoir dock
5135 Locking lever
5150 Water level indicator
5240 Heating element
6000 Vent flow

The invention claimed is:

1. A vent for a respiratory therapy system, the vent allowing for a vent flow of gases exhaled by a patient receiving a flow of breathable gas from a volume interior to the respiratory therapy system to ambient, the vent comprising:

a vent body having formed therein a plurality of slots, the plurality of slots together allowing the vent flow of exhaled gases from the volume to ambient, wherein each of the plurality of slots has an inlet and an outlet, a length extending perpendicularly between the inlet and the outlet, a width and a height, each of the width and the height extending in a direction perpendicular to the length, wherein the vent body is configured such that, for each of the plurality of slots, a ratio of the length to the height is at least 10 and a ratio of the width to the height is at least 15, and wherein the vent body is configured such that the plurality of slots are arranged such that the widths of the plurality of slots extend in mutually parallel directions.

2. A vent as claimed in claim 1, wherein, for each of the plurality of slots, the ratio of the length to the height is at most 40.

3. A vent as claimed in claim 1, wherein, for each of the plurality of slots, the inlet has an inlet area and the outlet has an outlet area, and the outlet area is greater than the inlet area.

4. A vent as claimed in claim 3, wherein, for each of the plurality of slots, a width of the slot at the outlet is greater than a width of the slot at the inlet.

5. A vent as claimed in claim 3, wherein, for each of the plurality of slots, a height of the slot at the outlet is greater than a height of the slot at the inlet.

6. A vent as claimed in claim 1, wherein the vent body is configured such that, for each of the plurality of slots, the slot is formed between a first side wall and a second side wall, each of the first side wall and the second side wall being surfaces of the vent body, the first side wall and the second side wall being separated in a direction parallel to the height of the slot, and wherein the vent body is configured such that the first side wall and the second side wall are substantially planar.

7. A vent as claimed in claim 1, wherein, in a direction along the width of the slot, the slot has a middle region proximate the middle of the slot and end regions proximate the ends of the slot, and wherein a length of the slot in the middle region is greater than a length of the slot in the end regions.

8. A vent as claimed in claim 1, wherein the length of the slot is substantially the same across the width of the slot.

9. A patient interface comprising:

a plenum chamber pressurisable to a therapeutic pressure of at least 6 $cmH_2O$ above ambient air pressure, said plenum chamber including a plenum chamber inlet port sized and structured to receive a flow of air at the therapeutic pressure for breathing by a patient, a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use; and a vent as claimed in claim 1, wherein the vent allows a continuous flow of gases exhaled by the patient from an interior of the plenum chamber to ambient, said vent being configured to maintain the therapeutic pressure in the plenum chamber in use, wherein the patient interface is configured to allow the patient to breath from ambient through their mouth in the absence of a flow of pressurised air through the plenum chamber inlet port, or the patient interface is configured to leave the patient's mouth uncovered.

10. A vent for a respiratory therapy system, the vent allowing for a vent flow of gases exhaled by a patient receiving a flow of breathable gas from a volume interior to the respiratory therapy system to ambient, the vent comprising:

a vent body having formed therein a plurality of slots, the plurality of slots together allowing the vent flow of exhaled gases from the volume to ambient, wherein each of the plurality of slots has an inlet having an inlet area and an outlet having an outlet area, a length extending perpendicularly between the inlet and the outlet, a width and a height, each of the width and the height extending in a direction perpendicular to the length, wherein the vent body is configured such that, for each of the plurality of slots, a ratio of the width to the height is at least 15, and the outlet area is greater than the inlet area, and wherein the vent body is configured such that the plurality of slots are arranged such that the widths of the plurality of slots extend in mutually parallel directions.

11. A vent as claimed in claim 10, wherein, for each of the plurality of slots, a width of the slot at the outlet is greater than a width of the slot at the inlet.

12. A vent as claimed in claim 11, wherein the vent body is configured such that, for each of the plurality of slots, the slot is formed between a first end wall and a second end wall, each of the first end wall and the second end wall being surfaces of the vent body, the first end wall and the second end wall being separated in a direction parallel to the width of the slot, and wherein a projection of the first end wall inwardly towards the volume would intersect with a projection of the second end wall inwardly towards the volume.

13. A vent as claimed in claim 12, wherein the angle at which the first end wall is oriented to the second end wall is at least 60°.

14. A vent as claimed in claim 10, wherein, for each of the plurality of slots, a height of the slot at the outlet is greater than a height of the slot at the inlet.

15. A vent as claimed in claim 10, wherein the vent body is configured such that, for each of the plurality of slots, the slot is formed between a first side wall and a second side wall, each of the first side wall and the second side wall being surfaces of the vent body, the first side wall and the second side wall being separated in a direction parallel to the height of the slot, and wherein the vent body is configured such that the first side wall and the second side wall are substantially planar.

16. A vent as claimed in claim 15, wherein, for each of the plurality of slots, the first side wall is oriented at an angle of at least 1° relative to the second side wall.

17. A vent as claimed in claim 10, wherein the vent body is configured such that, for each of the plurality of slots, the inlet is concave across the width of the slot.

18. A vent as claimed in claim 10, wherein the vent body is configured such that, for each of the plurality of slots, the outlet is convex across the width of the slot.

* * * * *